(12) United States Patent  
Messersmith et al.

(10) Patent No.: US 8,673,286 B2
(45) Date of Patent: Mar. 18, 2014

(54) DOPA-FUNCTIONALIZED, BRANCHED, POLY(AKLYLENE OXIDE) ADHESIVES

(75) Inventors: Phillip B. Messersmith, Clarendon Hills, IL (US); Jeffrey L. Dalsin, Madison, WI (US); Bruce P. Lee, Madison, WI (US); Sean A. Burke, Westchester, IL (US)

(73) Assignee: Northwestern University, Evanston, IL (US)

( * ) Notice: Subject to any disclaimer, the term of this patent is extended or adjusted under 35 U.S.C. 154(b) by 1295 days.

(21) Appl. No.: 12/099,254

(22) Filed: Apr. 8, 2008

(65) Prior Publication Data

US 2008/0247984 A1 Oct. 9, 2008

Related U.S. Application Data

(60) Provisional application No. 60/910,683, filed on Apr. 9, 2007.

(51) Int. Cl.
*A61Q 5/12* (2006.01)
(52) U.S. Cl.
USPC .................. 424/78.27; 424/78.02; 528/403
(58) Field of Classification Search
None
See application file for complete search history.

(56) References Cited

U.S. PATENT DOCUMENTS

| | | |
|---|---|---|
| 4,339,561 A | 7/1982 | Jacquet et al. |
| 4,496,397 A | 1/1985 | Waite |
| 4,585,585 A | 4/1986 | Waite |
| 4,615,697 A | 10/1986 | Robinson |
| 4,687,740 A | 8/1987 | Waite |
| 4,795,436 A | 1/1989 | Robinson |
| 4,808,702 A | 2/1989 | Waite |
| 4,908,404 A | 3/1990 | Benedict et al. |
| 4,978,336 A | 12/1990 | Capozzi et al. |
| 4,983,392 A | 1/1991 | Robinson |
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |
| 5,242,808 A | 9/1993 | Maugh et al. |
| 5,260,194 A | 11/1993 | Olson |
| 5,374,431 A | 12/1994 | Pang et al. |
| 5,410,023 A | 4/1995 | Burzio |
| 5,428,014 A | 6/1995 | Labroo et al. |
| 5,487,739 A | 1/1996 | Aebischer et al. |
| 5,490,980 A | 2/1996 | Richardson et al. |
| 5,520,727 A | 5/1996 | Vreeland et al. |
| 5,525,336 A | 6/1996 | Green et al. |
| 5,549,904 A | 8/1996 | Juergensen et al. |
| 5,563,047 A | 10/1996 | Petersen |
| 5,574,134 A | 11/1996 | Waite |
| 5,580,697 A | 12/1996 | Keana et al. |
| 5,582,955 A | 12/1996 | Keana et al. |
| 5,605,938 A | 2/1997 | Roufa et al. |
| 5,618,551 A | 4/1997 | Tardy et al. |
| 5,628,793 A | 5/1997 | Zirm |
| 5,705,177 A | 1/1998 | Roufa et al. |
| 5,705,178 A | 1/1998 | Roufa et al. |
| 5,736,132 A | 4/1998 | Juergensen et al. |
| 5,776,747 A | 7/1998 | Schinstine et al. |
| 5,800,828 A | 9/1998 | Dionne et al. |
| 5,817,470 A | 10/1998 | Burzio et al. |
| 5,830,539 A | 11/1998 | Yan et al. |
| 5,834,232 A | 11/1998 | Bishop et al. |
| 5,858,747 A | 1/1999 | Schinstine et al. |
| 5,935,849 A | 8/1999 | Schinstine et al. |
| 5,939,385 A | 8/1999 | Labroo et al. |
| 5,955,096 A | 9/1999 | Santos et al. |
| 5,968,568 A | 10/1999 | Kuraishi et al. |
| 5,985,312 A | 11/1999 | Jacob et al. |
| 5,994,325 A | 11/1999 | Roufa et al. |
| 6,010,871 A | 1/2000 | Takahara et al. |
| 6,020,326 A | 2/2000 | Roufa et al. |
| 6,022,597 A | 2/2000 | Yan et al. |
| 6,083,930 A | 7/2000 | Roufa et al. |
| 6,093,686 A | 7/2000 | Nakada et al. |
| 6,129,761 A | 10/2000 | Hubbell |
| 6,150,461 A | 11/2000 | Takei et al. |
| 6,156,348 A | 12/2000 | Santos et al. |
| 6,162,903 A | 12/2000 | Trowern et al. |

(Continued)

FOREIGN PATENT DOCUMENTS

DE 196 43 007 A1 4/1998
WO WO 88/03953 6/1988

(Continued)

OTHER PUBLICATIONS

Yu et al. Macromolecules 1998, 4739-4745.*
Podsiadlo et al. Adv. Mater. 2007, 19, 949-955.*
Statz et al. JACS 2005, 127,7972-7973.*
Dalsin et al., Bioinspired Antifouling Polymers. Materials Today 2005, 8, 9 (38-46).
Gristina, Biomaterial-Centered Infection—Microbial Adhesion Versus Tissue Integration. Science 1987, 237, (4822), 1588-1595.
Evans et al., Iron Chelator, Exopolysaccharide and Protease Production in *Staphylococcus epidermidis*—a Comparative-Study of the Effects of Specific Growth-Rate in Biofilm and Planktonic Culture. Microbiology-Uk 1994, 140, 153-157.
Yu et al., Adhesion of Coagulase-Negative Staphylococci and Adsorption of Plasma-Proteins to Heparinized Polymer Surfaces. Biomaterials 1994, 15, (10), 805-814.

(Continued)

*Primary Examiner* — Michael G Hartley
*Assistant Examiner* — Sean R Donohue
(74) *Attorney, Agent, or Firm* — Quarles & Brady LLP

(57) ABSTRACT

The invention describes DOPA functionalized, branched, polyalkylene oxide materials that are useful as adhesives.

29 Claims, 22 Drawing Sheets

(56) References Cited

U.S. PATENT DOCUMENTS

| | | | |
|---|---|---|---|
| 6,235,313 | B1 | 5/2001 | Mathiowitz et al. |
| 6,267,957 | B1 | 7/2001 | Green et al. |
| 6,284,267 | B1 | 9/2001 | Aneja |
| 6,294,187 | B1 | 9/2001 | Boyce et al. |
| 6,306,993 | B1 | 10/2001 | Rothbard et al. |
| 6,309,669 | B1 | 10/2001 | Setterstrom et al. |
| 6,322,996 | B1 | 11/2001 | Sato et al. |
| 6,325,951 | B1 | 12/2001 | Soper et al. |
| 6,331,422 | B1 | 12/2001 | Hubbell et al. |
| 6,335,430 | B1 | 1/2002 | Qvist |
| 6,365,187 | B2 | 4/2002 | Mathiowitz et al. |
| 6,368,586 | B1 | 4/2002 | Jacob et al. |
| 6,417,173 | B1 | 7/2002 | Roufa et al. |
| 6,486,213 | B1 | 11/2002 | Chen et al. |
| 6,491,903 | B1 | 12/2002 | Forster et al. |
| 6,497,729 | B1 | 12/2002 | Moussy et al. |
| 6,506,577 | B1 | 1/2003 | Deming et al. |
| 6,555,103 | B2 | 4/2003 | Leukel et al. |
| 6,565,960 | B2 | 5/2003 | Koob et al. |
| 6,566,074 | B1 | 5/2003 | Goetinck |
| 6,566,406 | B1 | 5/2003 | Pathak et al. |
| 6,635,274 | B1 | 10/2003 | Masiz et al. |
| 6,663,883 | B1 | 12/2003 | Akiyama et al. |
| 6,821,530 | B2 | 11/2004 | Koob et al. |
| 6,887,845 | B2 | 5/2005 | Barron et al. |
| 7,009,034 | B2 | 3/2006 | Pathak et al. |
| 7,208,171 | B2 | 4/2007 | Messersmith et al. |
| 7,300,991 | B2 | 11/2007 | Nishimura et al. |
| 2001/0043940 | A1 | 11/2001 | Boyce et al. |
| 2001/0049400 | A1 | 12/2001 | Alli et al. |
| 2002/0022013 | A1 | 2/2002 | Leukel et al. |
| 2002/0049290 | A1 | 4/2002 | Vanderbilt |
| 2002/0182633 | A1 | 12/2002 | Chen et al. |
| 2003/0009235 | A1 | 1/2003 | Manrique et al. |
| 2003/0012734 | A1 | 1/2003 | Pathak et al. |
| 2003/0039676 | A1 | 2/2003 | Boyce et al. |
| 2003/0065060 | A1 | 4/2003 | Qvist et al. |
| 2003/0069205 | A1 | 4/2003 | Roufa et al. |
| 2003/0087338 | A1 | 5/2003 | Messersmith et al. |
| 2003/0099682 | A1 | 5/2003 | Moussy et al. |
| 2003/0109587 | A1 | 6/2003 | Mori |
| 2003/0208888 | A1 | 11/2003 | Fearing et al. |
| 2004/0005421 | A1 | 1/2004 | Gervase et al. |
| 2004/0028646 | A1 | 2/2004 | Gross et al. |
| 2005/0032929 | A1 | 2/2005 | Greener |
| 2005/0288398 | A1 | 12/2005 | Messersmith et al. |
| 2006/0009550 | A1 | 1/2006 | Messersmith et al. |
| 2007/0031498 | A1* | 2/2007 | Zong et al. ............... 424/486 |

FOREIGN PATENT DOCUMENTS

| | | |
|---|---|---|
| WO | WO 92/10567 | 6/1992 |
| WO | WO 94/28937 | 12/1994 |
| WO | WO 97/34016 | 9/1997 |
| WO | WO 98/07076 | 2/1998 |
| WO | WO 01/44401 A1 | 6/2001 |
| WO | WO 02/34764 A1 | 5/2002 |
| WO | WO 03/008376 A2 | 1/2003 |
| WO | WO 03/080137 A1 | 10/2003 |
| WO | WO 2004/042068 A2 | 5/2004 |

OTHER PUBLICATIONS

Jose et al., Vancomycin covalently bonded to titanium beads kills *Staphylococcus aureus*. Chemistry & Biology 2005, 12, (9), 1041-1048.

Desai et al., Surface-Immobilized Polyethylene Oxide for Bacterial Repellence. Biomaterials 1992, 13, (7), 417-420.

Burdinski et al., Universal Ink for Microcontact Printing. Angwandte Chemie 2006, 45, 1-5.

Floriolli et al., Marine surfaces and the expression of specific byssal adhesive protein variants in *Mytilus*. Mar Biotechnol 2000, 2, 352-363.

Bain et al., Molecular-level Control over Surface Order in Self-Assembled Monolayer Films of Thiols on Gold. Science 1988, 240, (4848), 62-63.

Waite, Reverse engineering of bioadhesion in marine mussels. Bioartificial Organs ii: Technology, Medicine, and Materials 1999, 875, 301-309.

Pasche et al., Poly(l-lysine)-graft-poly(ethylene glycol) assembled monolayers on niobium oxide surfaces: A quantitative study of the influence of polymer interfacial architecture on resistance to protein adsorption by ToF-SIMS and in situ OWLS. Langmuir 2003,19, (22), 9216-9225.

Zhang et al., Reactive coupling of poly(ethylene glycol) on electroactive polyaniline films for reduction in protein adsorption and platelet adhesion. Biomaterials 2002, 23, (3), 787-795.

Holl et al., Solid-State NMR Analysis of Cross-Linking in Mussel Protein Glue. Archives of Biochemistry and Biophysics 1993, 302, (1),255-258.

International Search Report, PCT/US2008/050721.

Fuller et al., Biopolymers, 1978. DOPA-Containing Polypeptides. Improved synthesis of high-molecular-weight poly(L-DOPA) and water-soluble copolypeptides. 17(12):p. 2939-43.

Fuller et al., Biopolymers, 1976. A Procedure for the Facile Synthesis of Amino-Acid N-Carboxyanhydride. 15:p. 1869-1871.

Lee et al., Macromolecules, 2006. Rapid Gel Formation and Adhesion in Photocurable and Biodegradable Block Copolymers with High DOPA Content 39:p. 1740-1748.

Advincula, "Surface Initiated Polymerization from Nanoparticle Surfaces," *J. Dispersion Sci. Technol.*, vol. 24, Nos. 3 & 4 (2003), pp. 343-361.

Ahmed, et al., "Synthesis and Application of Fluorescein-Labeled Pluronic Block Copolymers to the Study of Polymer-Surface Interactions," *Langmuir*, vol. 17, No. 2 (2001), pp. 537-546.

Alexandridis, P.; Nivaggioli, T.; Hatton, T. A., "Temperature Effects on Structural Properties of Pluronic P104 and F108 PEO-PPO-PEO Block Copolymer Solutions," *Langmuir*, vol. 11, No. 5 (1995), pp. 1468-1476.

Alexandridis, P., "Poly(ethylene oxide)-Poly(propylene oxide) Block Copolymer Surfactants," *Curr. Opin. Colloid Interface Sci.*, vol. 2, No. 5 (1997), pp. 478-489.

Alivisatos, P., "The use of nanocrystals in biological detection," *Nature Biotechnology*, vol. 22, No. 1 (2004), pp. 47-52.

Alleyne, Jr., et al., "Efficacy and biocompatibility of a photopolymerized, synthetic, absorbable hydrogel as a dural sealant in a canine craniotomy model," *J. Neurosurg.*, vol. 88 (1998), pp. 308-313.

Andreopoulos, et al., "Light-induced tailoring of PEG-hydrogel properties," *Biomaterials*, vol. 19 (1998), pp. 1343-1352.

Andrzejewska, et al., "The role of oxygen in camphorquinone-initiated photopolymerization," *Macromol. Chem. Phys.*, vol. 199 (1998), pp. 441-449.

Araujo, et al., "Interaction of Catechol and Gallic Acid with Titanium Dioxide in Aqueous Suspensions. 1. Equilibrium Studies," *Langmuir*, vol. 21 (2005), pp. 3470-3474.

Armstrong et al., "Scanning Microcalorimetric Investigations of Phase Transitions in Dilute Aqueous Solutions of Poly(oxypropylene)," *J. Phys. Chem.*, vol. 99 (1995), pp. 4590-4598.

Arnow, "Colorimetric Determination of the Component of 3, 4-Dihydroxyphemylalanine-Tyrosine Mixtures," *J. Biol. Chem.*, vol. 118 (1937), pp. 531-538.

Arzt et al., "From micro to nano contacts in biological attachment devices," *Proc. Nat. Acad. Sci. USA*, vol. 100 (2003), pp. 10603-10606.

Arzt, "Biological and artificial attachment devices: Lessons for materials scientists from flies and geckos," *Mater. Sci. Eng. C*, vol. 26 (2006), pp. 1245-1250.

Autumn et al., "Adhesive force of a single gecko foot-hair," *Nature*, vol. 405 (2000), pp. 681-685.

Autumn et al., "Evidence for van der Weals adhesion in gecko setae," *Proc. Nat. Acad. Sci. USA*, vol. 99 (2002), pp. 12252-12256.

Baird, et al. (2007), "Reduction of Incisional Cerebrospinal Fluid Leak Following Posterior Foss Surgery with the use of Duraseal," American Association of Neurosurgeons. Abstract retrieved Jul. 23, 2008, from AANS Abstract Center database. Available from: http://www.aans.org/library/article.aspx?ArticleId=42392.

(56) References Cited

OTHER PUBLICATIONS

Balsa-Canto, et al., "Reduced-Order Models for Nonlinear Distributed Process Systems and Their Application in Dynamic Optimization," *Ind. Eng. Chem. Res.*, vol. 43 (2004), pp. 3353-3363.

Banerjee, et al., "Derivatives of 3, 4-Dihydroxyphenylalanine for Peptide Synthesis," *J. Org. Chem.*, vol. 41, No. 18 (1976), pp. 3056-3058.

Barbakadze, et al., "Poly[3-(3, 4-dihydroxyphenyl)glyceric Acid], A New Biologically Active Polymer from *Symphytum asperum Lepech.* and *S. caucasicum Bieb.* (Boraginaceae)," *Molecules*, vol. 10 (2005), pp. 1135-1144.

Barichello et al., "Absorption of insulin from Pluronic F-127 gels following subcutaneous administration in rats," *Int. J. Pharm.*, vol. 184 (1999), pp. 189-198.

Benedek, "End Uses of Pressure-Sensitive Products" in *Developments in Pressure-Sensitive Products*, Benedek (ed.), CRC Press: Boca Raton, FL (2006). pp. 539-596.

Bharathi, et al., "Direct synthesis of gold nanodispersions in sol-gel derived silicate sols, gels and films," *Chem. Commun.* (1997), pp. 2303-2304.

Bontempo, et al., "Atom Transfer Radical Polymerization as a Tool for Surface Functionalization," *Adv. Mater.*, vol. 14, No. 17 (2002), pp. 1239-1241.

Boogaarts, et al., "Use of a novel absorbable hydrogel for augmentation of dural repair: results of a preliminary clinical study," *Neurosurg.*, vol. 57 (2005), pp. 146-151.

Bromberg, "Novel Family of Thermogelling Materials via C—C Bonding between Poly(acrylic acid) and Poly(ethylene oxide)-*b*-poly(propylene oxide)-*b*-poly(ethylene oxide)," *J. Phys. Chem. B*, vol. 102 (1998), pp. 1956-1963.

Bromberg, "Self-Assembly in Aqueous Solutions of Polyether-Modified Poly(acrylic acid)," *Langmuir*, vol. 14 (1998), pp. 5806-5812.

Bromberg, "Temperature-responsive gels and thermogelling polymer matrices for protein and peptide delivery," *Advanced Drug Reviews*, vol. 31 (1998), pp. 197-221.

Brown, et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Shear Measurements," *J. Phys. Chem.*, vol. 95 (1991), pp. 1850-1858.

Bruinsma, et al., "Bacterial adhesion to surface hydrophilic and hydrophobic contact lenses," *Biomaterials*, vol. 22 (2001), pp. 3217-3224.

Bryant, et al., "Cytocompatibility of UV and visible light photoinitiating systems on cultured NIH/3T3 fobroblasts in vitro," *J. Biomater. Sci. Polymer Edn*, vol. 11, No. 5 (2000), pp. 439-457.

Burdick, et al., "Synthesis and Characterization of Tetrafunctional Lactic Acid Oligomers: A potential In Situ Forming Degradable Orthopaedic Biomaterial," *J. Polym. Sci., Part A: Polym. Chem.*, vol. 39 (2001), pp. 683-692.

Burzio, et al., "Cross-Linking in Adhesive Quinoproteins: Studies with Model Decapeptides," *Biochemistry*, vol. 39 (2000), pp. 11147-11153.

Cabana, et al., "Study of the Gelation Process of Polyethylene Oxide$_a$—Polypropylene Oxide$_b$—Polyethylene Oxide$_a$ Copolymer (Poloxamer 407) Aqueous Solutions," *J. Colloid Interface Sci.*, vol. 190 (1997), pp. 307-312.

Campbell, et al., "Evaluation of Absorbable Surgical Sealants: In vitro Testing," Confluent Surgical, Inc. (2005) 'White Paper. Available from: http://www.confluentsurgical.com/pdf/ds/6070_DuraSeal_Invitro_WP13-25.pdf.

Carmichael, et al., "Selective Electroless Metal Deposition Using Microcontact Printing of Phosphine—Phosphonic Acid Inks," *Langmuir*, vol. 20 (2004), pp. 5593-5598.

Chalykh, et al., "Pressure-Sensitive Adhestion in the Blends of Poly(N-vinyl pyrrolidone) and Poly(ethylene glycol) of Disparate Chain Lengths," *J. of Adhes.*, vol. 78 (2002), pp. 667-694.

Chehimi, et al., "XPS investigations of acid-base interactions in adhesion. Part 3. Evidence for orientation of carbonyl groups from poly(methylmethacrylate) (PMMA) at the PMMA—glass and PMMA—SiO$_2$ interfaces," *J. Electron. Spectrosc. Relat. Phenom.*, vol. 63 (1993), pp. 393-407.

Chen, et al., "Temperature-Induced Gelation Pluronic-g-Poly(acrylic acid) Graft Copolymers for Prolonged Drug Delivery to the Eye," in Harris, et al. (eds.) *Poly(ethylene glycol): Chemistry and Biological Applications*. New York, NY: Oxford University Press USA, 1997. pp. 441-451.

Chen, et al., "Enzymatic Methods for in Situ Cell Entrapment and Cell Release," *Biomacromolecules*, vol. 4 (2003), pp. 1558-1563.

Collier, et al., "Enzymatic Modification of Self-Assembled Peptide Structures with Tissue Transglutaminase," *Bioconjugate Chem.*, vol. 14 (2003), pp. 748-755.

Collier, et al., "Self-Assembling Polymer-Peptide Conjugates: Nanostructural Tailoring," *Adv. Mater.*, vol. 16, No. 11 (2004), pp. 907-910.

Collins, et al., "Use of collagen film as a dural substitute: Preliminary animal studies," *J. Biomed. Mater. Res.*, vol. 25 (1991), pp. 267-276.

Connor, et al., "New Sol—Gel Attenuated Total Reflection Infrared Spectroscopic Method for Analysis of Adsorption at Metal Oxide Surfaces in Aqueous Solutions. Chelation of $TiO_2$, $ZrO_2$, and $Al_2O_3$ Surfaces by Catechol, 8-Quinolinol, and Acetylacetone," *Langmuir*, vol. 11 (1995), pp. 4193-4195.

Cosgrove, et al., "Safety and efficacy of a novel polyethylene glycol hydrogel sealant for watertight dural repair," *J. Neurosurg.*, vol. 106 (2007), pp. 52-58.

Cosgrove, "Safety and Efficacy of a Novel PEG Hydrogel Sealant (DuraSeal®) for Watertight Closure after Dural Repair," Presented at the Congress of Neurological Surgeons 55th Annual Meeting, Boston, MA, Oct. 2005. Available from: http://www.confluentsurgical.com/pdf/ds/CosgroveAbstractCNS2005.pdf.

Crescenzi, et al., "New Gelatin-Based Hydrogels via Enzymatic Networking," *Biomacromolecules*, vol. 3 (2002), pp. 1384-1391.

Creton, "Pressure-Sensitive Adhesives: An Introductory Course," *MRS Bulletin*, vol. 26, No. 6 (2003), pp. 434-439.

Crosby, et al., "Rheological properties and adhesive failure of thin viscoelastic layers," *J. Rheol.*, vol. 46, No. 1 (2002), pp. 273-294.

Crosby, et al., "Controlling Polymer Adhesion with "Pancakes"," *Langmuir*, vol. 21 (2005), pp. 11738-11743.

Cruise, et al., "A Sensitivity Study of the Key Parameters in the Interfacial Photopolymerization of Poly(etheylene glycol) Dlacrylate upon Porcine Islets," *Biotechnol. Bioeng.*, vol. 57, Issue 6 (1998), pp. 655-665.

Dai, et al., "Novel pH-Responsive Amphiphilic Diblock Copolymers with Reversible Micellization Properties," *Langmuir* 19 (2003). pp. 5175-5177.

Dalsin, et al., "Surface Modification for Protein Resistance Using a Biomimetic Approach," *Mat. Res. Soc. Symp. Proc.*, vol. 774 (2002), pp. 75-80.

Dalsin, et al., "Mussel Adhesive Protein Mimetic Polymers for the Preparation of Nonfouling Surfaces," *J. Am. Chem. Soc.* 125 (2003). pp. 4253-4258.

Dalsin, et al., "Antifouling Performance of Poly(ethylene glycol) Anchored onto Surfaces by Mussel Adhesive Protein Mimetic Peptides," *Polymeric Materials Science and Engineering* 90 (2004). pp. 247-248.

Dalsin, et al., "Protein Resistance of Titanium Oxide Surfaces Modified by Biologically Inspired mPEG—DOPA," *Langmuir* 21 (2005). pp. 640-646.

Davis, et al., "Polymeric microspheres as drug carriers," *Biomaterials* 9 (1), 1988. pp. 111-115.

Deible, et al., "Creating molecular barriers to acute platelet deposition on damaged arteries with reactive polyethylene glycol," *J. Biomed. Maters. Res.* 41 (1998). pp. 251-256.

Deming, "Mussel byssus and biomolecular materials," *Current Opinion in Chemical Biology*, 3 (1), 1999. pp. 100-105.

Deming, et al., "Mechanistic Studies of Adhesion and Crosslinking in Marine Adhesive Protein Analogs," *Polym. Mater. Sci. Eng.*, 80 (1999). pp. 471-472.

Deruelle, et al., "Adhesion at the Solid—Elastomer Interface: Influence of the Interfacial Chains," *Macromolecules*, vol. 28 (1995), pp. 7419-7428.

(56) References Cited

OTHER PUBLICATIONS

Desai, et al., "In Vitro Evaluation of Pluronic F127-Based Controlled-Release Ocular Delivery Systems for Polocarpine," *J. Phar. Sci.*, 87 (2), 1998. pp. 226-230.
Dillow, et al., "Adhesion of $\alpha_5\beta_1$ receptors to biomimetic substrates constructed from peptide amphiphiles," *Biomaterials*, vol. 22 (2001), pp. 1493-1505.
Donkerwolcke, et al., "Tissue and bone adhesives—historical aspects," *Biomaterials* 19 (1998). pp. 1461-1466.
Dossot, et al., "Role of Phenolic Derivatives in Photopolymerization of an Acrylate Coating," *J. Appl. Polymer. Sci.*, 78 (2000). pp. 2061-2074.
Drumheller, et al., "Polymer Networks with Grafted Cell Adhesion Peptides for Highly Biospecific Cell Adhesive Substrates," *Anal. Biochem.*, vol. 222 (1994), pp. 380-388.
Elbert, et al., "Reduction of fibrous adhesion formation by a copolymer possessing an affinity for anionic surfaces," *J. Biomed. Mater. Res.*, vol. 42, Issue 1 (1998), pp. 55-65.
Elisseeff, et al., "Photoencapsulation of chondrocytes in poly(ethylene oxide)-based semi-interpenetrating networks," *J. Biomed. Mater. Res.*, vol. 51, Issue 2 (2000), pp. 164-171.
Erli, et al., "Surface pretreatments for medical application of adhesion," *BioMed. Eng. Online*, 2 (15), 2003. Available from: http://www.biomedical-engineering-online.com/content/2/2/15.
Fan et al., "Surface-Initiated Polymerization from $TiO_2$ Nanoparticle Surfaces through a Biomimetic Initiator: A New Route toward Polymer-Matrix Composites," *Comp. Sci. Tech.*, 66 (9), 2006. pp. 1195-1201.
Fang, et al., "Effect of Molecular Structure on the Adsorption of Protein on Surfaces with Grafted Polymers," *Langmuir*, vol. 18 (2002), pp. 5497-5510.
Faulkner, et al., "A New Stable Pluronic F68 Gel Carrier for Antibiotics in Contaminated Wound Treatment," *Am. J. Emerg. Med.*, 15 (1), 1997. pp. 20-24.
Feldstein, et al., "Molecular Design of Hydrophilic Pressure-Sensitive Adhesives for Medical Applications," in *Developments in Pressure-Sensitive Products*, I. Benedek (ed.). 2006, CRC Press: Boca Raton, FL. pp. 473-503.
Filpula, et al., "Structural and Functional Repetition in a Marine Mussel Adhesive Protein," *Biotechnol. Prog.* 6 (1990). pp. 171-177.
Fischer, et al., "In vitro cytotoxicity testing of polycations: influence of polymer structure on cell viability and hemolysis," *Biomaterials* 24 (2003). pp. 1121-1131.
Flanigan, et al., "Adhesive and Elastic Properties of Thin Gel Layers," *Langmuir*, vol. 15 (1999), pp. 4966-4974.
Flanigan, et al., "Structural Development and Adhesion of Acrylic ABA Triblock Copolymer Gels," *Macromolecules*, vol. 32 (1999), pp. 7251-7262.
Flood, et al., "Efficient Asymmetric Epoxidation of $\alpha,\beta$-Unstarudated Ketones Using a Soluble Triblock Polyethylene Glycol-Polyamino Acid Catalyst," *Org. Lett.*, vol. 3, No. 5 (2001), pp. 683-686.
Floudas, et al., "Hierarchical Self-Assembly of Poly($\gamma$-benzyl-L-glutamate)—Poly(ethylene glycol)—Poly($\gamma$-benzyl-L-glutamate) Rod—Coil—Rod Triblock Copolymers," *Macromolecules*, vol. 36 (2003), pp. 3673-3683.
Flory, et al., "Effect of Volume Exclusion on the Dimensions of Polymer Chains," *J. Chem. Phys.*, vol. 44, No. 6 (1966), pp. 2243-2248.
Floyd-Smith, et al., "Interferon Action: RNA Cleavage Pattern of a (2'-5')Oligoadenylate-Dependent Endonuclease," *Science*, vol. 212, No. 4498 (May 29, 1981), pp. 1030-1032.
Frank, et al., "Adhesion of *Mytilus edulis* Foot Protein 1 on Silica: Ionic Effects on Biofouling," *Biotechnol. Prog.* 18 (2002). pp. 580-586.
Fuchsbauer, et al., "Influence of gelatin matrices cross-linked with transglutaminase on the properties of an enclosed bioactive material using $\beta$-galactosidase as model system," *Biomaterials* 17 (1996). pp. 1481-1488.
Fujisawa, et al., "Kinetic Evaluations of the Reactivity of Flavonoids as Radical Scavengers," *SAR QSAR Environ. Res.*, Vo. 13, No. 6 (2002), pp. 617-627.
Geim, et al., "Microfabricated adhesive mimicking gecko foot-hair," *Nat. Materials* 2 (2003). pp. 461-463.
Ghosh, et al., "N,N'-Disuccinimidyl Carbonate: A Useful Reagent for Alkoxycarbonylation of Amines," *Tetra. Lett.* 33 (20), 1992. pp. 2781-2784.
Gidanian, et al., "Redox behavior of melanins: direct electrochemistry of dihydroxyindole-melanin and its Cu and Zn adducts," *J. Inorg. Biochem.* 89 (2002). pp. 54-60.
Green, et al., "A surface plasmon resonance study of albumin adssoption to PEO-PPO-PEO triblock copolymers," *J. Biomed. Res.* 42 (1998). pp. 165-171.
Gross, et al., "Amine Bindindg Sites in Acyl Intermediates of Transglutaminases," *J. Biol. Chem.* 242 (11) (1977). pp. 3752-3759.
Grotenhuis, et al,. "Synthetic Dural Sealant for Prevention of Post-operative CSF Leakage," Presented at the American Association of Neurological Surgeons; Apr. 2003, San Diego, CA. Available from: http://www.confluentsurgical.com/pdf/ds/AbstractGrotenhuisAbstract.pdf.
Grotenhuis, et al., "A Novel Absorbable Hydrogel for Dural Repair: Results of a Pilot Clinical Study," Confluent Surgical, Inc. (2005) 'White Paper. Available from: http://www.confluentsurgical.com/pdf/ds/DuraSeal_Pilot_Study_WP4-7-05.pdf.
Grotenhuis, "Costs of postoperative cerebrospinal fluid leakage: 1-year, retrospective analysis of 412 consecutive nontrauma cases," *Surg. Neurol.*, vol. 64, No. 6 (2005), pp. 493-494.
Gu, et al., "Synthesis of Aluminum Oxide/Gradient Copolymer Composites by Atom Transfer Radical Polymerization," *Macromolecules* 35 (2002). pp. 8913-8916.
Gu, et al., "The role of microbial biofilms in deterioration of space station candidate materials," *Int. Biodeterioration Biodegradation* 41 (1998). pp. 25-33.
Guvendiren, et al., "Adhesion in Self-Assembled Hydrogels with High DOPA Content," *Proceedings of the 30$^{th}$ Annual Meeting of the Adhesion Society* (2007).
Guvendiren, et al., "Synthesis and Adhesion Properties of DOPA Incorporated Acrylic Triblock Hydrogels," *Proceedings of the 29$^{th}$ Annual Meeting of the Adhesion Society* (2006). pp. 277-279.
Haemers, et al., "Effect of Oxidation Rate on Cross-Linking of Mussel Adhesive Proteins," *Biomacromolecules*, vol. 4 (2003), pp. 632-640.
Hajjaji, et al., "Effect of N-Alkybetaines on the Corrosion of Iron in 1 M HCl Soluction," *Corrosion*, vol. 49, No. 4 (1993), pp. 326-334.
Hanawa, et al., "XPS Characterization of the Surface Oxide Film of 316L Stainless Steel Samples that were Located in Quasi-Biological Environments," *Mater. Trans., JIM*, vol. 43, No. 12 (2002), pp. 3088-3092.
Hansen, et al., "Enzymatic Tempering of a Mussel Adhesive Protein Film," *Langmuir* 14 (1998). pp. 1139-1147.
Harris, "Laboratory Synthesis of Polyethylene Glycol Derivatives," *JIMS—Rev. Macromol. Chem. Phys.*, vol. C25, No. 3 (1985), pp. 325-373.
Harris (ed.), "Introduction to Biotechnical and Biomedical Applications of Poly(Ethylene Glycol)" in *Poly(Ethylene Glycol) Chemistry: Biotechnical and Biomedical Applications*, Plenum Press: New York, 1992. pp. 1-14.
Hennink, et al., "Novel crosslinking methods to design hydrogels," *Adv. Drug Deliver. Rev.*, vol. 54 (2002), pp. 13-36.
Hern, et al., "Incorporation of adhesion peptides into nonadhesive hydrogels useful for tissue resurfacing," *J. Biomed. Mater. Res.*, vol. 39, Issue 2 (1998), pp. 266-276.
Hillery, et al., "The effect of adsorbed poloxamer 188 and 407 surfactants on the intestinal uptake of 60-nm polystyrene particles after oral administratin in the rat," *Int. J. Pharm.* 132 (1996). pp. 123-130.
Ho, et al., "Nanoseparated Polymeric Networks with Multiple Antimicrobial Properties," *Adv. Mater.* 16 (12), 2004. pp. 957-961.
Hoffman, "Hydrogels for biomedical applications," *Adv. Drug Deliver. Rev.*, vol. 43 (2002), pp. 3-12.

(56) References Cited

OTHER PUBLICATIONS

Hohenadl, et al., "Two Adjacent N-terminal Glutamines of BM-40 (Osteonectin, SPARC) Act as Amine Acceptor Sites in Transglutaminase$_c$-catalyzed Modification," *J. Biol. Chem.* 270 (40), 1995. pp. 23415-23420.
Hrkach, et al., "Synthesis of Poly(L-lactic acid-*co*-L-lysine) Graft Copolymers," *Macromolecules*, vol. 28 (1995), pp. 4736-4739.
Hu, et al., "Protection of 3,4-dihydroxyphenylalanine (DOPA) for Fmoc solid-phase peptide synthesis," *Tetra. Lett.* 41 (2000). pp. 5795-5798.
Hu, et al., "Rational Design of Transglutaminase Substrate Peptides for Rapid Enzymatic Formation of Hydrogels," *J. Am. Chem. Soc.*, vol. 125, (2003), pp. 14298-14299.
Huang, et al., "Synthesis and Characterization of Self-Assembling Block Copolymers Containing Adhesive Moieties," *Polym. Prepr.* 42 (2), 2001. pp. 147-148.
Huang, et al., "Synthesis and Characterization of Self-Assembling Block Copolymers Containing Bioadhesive End Groups," *Biomacromolecules* 3 (2002). pp. 397-406.
Huang, et al., "Covalent Attachment of Novel Poly(ethylene glycol)—Poly(DL-lactic acid) Copolymeric Micelles to TiO$_2$ Surfaces," *Langmuir* 18 (2002). pp. 252-258.
Huang, et al., "Functionalization of Surfaces by Water-Accelerated Atom-Transfer Radical Polymerization of Hydroxyethyl Methacrylate and Subsequent Derivatization," *Macromolecules* 35 (2002). pp. 1175-1179.
Huang, et al., "Poly(L-lysine)-*g*-poly(ethylene glycol) Layers on Metal Oxide Surfaces: Surface-Analytical Characterization and Resistance to Serum and Fibrinogen Adsorption," *Langmuir*, vol. 17 (2001), pp. 489-498.
Huang, "Molecular aspects of muco- and bioadhesion: Tethered structures and site-specific surfaces," *J. Controlled Release*, vol. 65 (2000), pp. 63-71.
Huber, et al., "Resolving the nanoscale adhesion of individual gecko spatulae by atomic force microscopy," *Biol. Lett.* 1 (2005). pp. 2-4.
Huber, et al., "Evidence for capillarity contributions to gecko adhesion from single spatula nanomechanical measurements," *Proc. Nat. Acad. Sci. USA*, 102 (45), 2005. pp. 16293-16296.
Huin-Amargier, et al., "New physically and chemically crosslinked hyaluronate (HA)-based hydrogels for cartilage repair," *J. Biomed. Mater. Res.* 76A (2), 2006. pp. 416-424.
Hunter, "Molecular hurdles in polyfectin design and mechanistic background to polycation inducted cytotoxicity," *Adv. Drug Deliver. Rev.*, vol. 58 (2006). pp. 1523-1531.
Huller, et al., "Calibration of atomic-force microscope tips," *Rev. Sci. Instrum.* 64 (7), Jul. 1993. pp. 1868-1873.
Hvidt, et al., "Micellization and Gelation of Aqueous Solutions of a Triblock Copolymer Studied by Rheological Techniques and Scanning Calorimetry," *J. Phys. Chem.* 98 (1994). pp. 12320-12328.
Hwang, et al., "Expression of Functional Recombinant Mussel Adhesive Protein Mgfp-5 in *Escherichia coli*," *Appl. Environ. Microbiol.* 70 (6), 2004. pp. 3352-3359.
Ikada, "Tissue Adhesives, in *Wound Closure Biomaterials and Devices*," Chu, et al. (eds.), CRC Press, Inc.: Boca Raton, FL, 1997. pp. 317-346.
International Search Report for PCT/US2003/034633; WO 2004/042068 A3 (May 21, 2005); Northwestern University (Applicant); Messersmith, et al. (inventors).
International Search Report for PCT/US2005/006418; WO 2005/118831 A3 (Dec. 15, 2005); Northwestern University (Applicant); Messersmith, et al. (inventors).
International Search Report for PCT/US2005/024642; WO 2006/091226 A3 (Aug. 31, 2006); Northwestern University (Applicant); Messersmith, et al. (inventors).
International Search Report for PCT/US/2005/041280; WO 2006/055531 A3 (May 26, 2006); Northwestern University (Applicant); Messersmith, et al. (Inventors).
International Search Report for PCT/US2007/075299; WO 2008/019352 A3 (Feb. 14, 2008); Nerites Corporation (Applicant); Lee (Inventor).
International Search Report for PCT/US2002/23005; WO 03/008376 A3 (Jan. 30, 2003); Northerwestern University (Applicant); Messersmith, et al. (inventors).
Ishihara, et al., "Photocrosslinkable chitosan as a dressing wound occlusion and accelerator in healing process," *Biomaterials*, vol. 23, No. 3 (2002), pp. 833-840.
Jackson, "Tissue sealants: Current status, future potential," *Nat. Med.*, vol. 2, No. 5, (May 1996), pp. 637-638.
Jackson, "Fibrin sealants in surgical practice: An overview," *Am. J. Surg.*, vol. 182 (2001), pp. 1S-7S.
Jänchen, et al., "Adhesion Energy of Thin Collagen Coatings and Titanium," *Surf. Interface Anal.*, vol. 27 (1999), pp. 444-449.
Jensen, et al., "Lipopeptides Incorporated into Supported Phospholipid Monolayers Have High Specific Activity at Low Incorporation Levels," *J. Am. Chem. Soc.*, vol. 126, No. 46 (2004), pp. 15223-15230.
Jeon, et al., "Protein-Surface Interactions in the Presence of Polyethylene Oxide," *J. Colloid. Interface Sci.*, vol. 142, No. 1 (1991), pp. 159-166.
Jewell, et al., "Pharmacokinetics of RheothRx Injection in Healthy Male Volunteers," *J. Phar. Sci.* vol. 86, No. 7 (1997), pp. 808-812.
Jo, et al., "Surface modification using silanated poly(ethylene glycol)s," *Biomaterials*, vol. 21 (2000), pp. 605-616.
Johnson, et al., "Surface Energy and Contact of Elastic Solids," *Proc. R. Soc. Lond., A*, vol. 324, No. 1558 (1971), pp. 301-313.
Jones, et al., "Controlled Surface-Initiated Polymerization in Aqueous Media," *Adv. Mater.*, vol. 13, No. 16 (2001), pp. 1256-121259.
Jones, et al., "In Situ forming biomaterials," *Oral Maxillofacial Surg. Clin. N. Am.*, vol. 14 (2002), pp. 29-38.
Kacher, et al., "DuraSeal MR and CT Imaging: Evaluation in a Canine Craniotomy Model," Date: 2006.
Kahlem, et al., "Peptides containing glutamine repeats as substrates for transglutaminase-catalyzed cross-linking: Relevance to diseases of the nervous system," *Proc. Natl. Acad. Sci. USA*, vol. 93 (Dec. 1996), pp. 14580-14585.
Kellaway, et al., "Oral Mucosal Drug Delivery," in *Oral Mucosal Drug Delivery*, Rathbone (ed.). 1996, Marcel Dekkers, Inc.: New York, NY. pp. 221-239.
Kenausis, et al., "Poly(L-lysine)-*g*-Poly(ethylene glycol) Layers on Metal Oxide Surfaces: Attachment Mechanism and Effects on Polymer Architecture on Resistance to Protein Adsoprtion," *J. Phys. Chem. B*, vol. 104 (2000), pp. 3298-3309.
Khudyakov, et al., "Kinetics of Photopolymerization of Acrylates with Functionality of 1-6," *Ind. Eng. Chem. Res.* 38 (1999). pp. 3353-3359.
Kingshott, et al., "Effects of cloud-point grafting, chain length, and density of PEG layers on competitive adsorption of ocular proteins," *Biomaterials* 23 (2002). pp. 2043-2056.
Kirschenbaum, et al., "Sequence-specific polypeptoids: A diverse family of heteropolymers with stable secondary structure," *Proc. Natl. Acad. Sci. USA* 95 (1998). pp. 4303-4308.
Kitano, et al., "Resistance of zwitterionic telomers accumulated on metal surfaces against nonspecific adsorption of proteins," *J. Colloid Interface Sci.* 282 (2005). pp. 340-348.
Klug, et al, "In Situ Analysis of Peptidyl DOPA in Mussel Byssus Using Rotational-Echo Double-Resonance NMR," *Arch. Biochem. Biophys.*, vol. 333, No. 1 (Sep. 1, 1996), pp. 221-224.
Kolb, et al., "Click Chemistry: Diverse Chemical Function from a Few Good Reactions," *Agnew. Chem. Int. Ed.*, vol. 40 (2001), pp. 2005-2021.
Koob, et al., "Mechanical and thermal properties of novel polymerized NDGA-gelatin hydrogels," *Biomaterials*, vol. 24 (2003), pp. 1285-1292.
Korobkova, et al., "From molecular noise to behavioural variability in a single bacterium," *Nature* 428 (2004). pp. 574-578.
Kummert, et al., "The Surface Complexation of Organic Acids of Hydrous γ-Al$_2$O$_3$," *J. Colloid Interface Sci.*, vol. 75, No. 2 (Jun. 1980), pp. 373-385.
Laucournet, et al., "Catechol derivatives and anion adsorption onto alumina surfaces in aqueous media: influence on the electrokinetic properties," *J. Eur. Ceram. Soc.* 21 (2001). pp. 869-878.
LaVoie, et al., "Dopamine covalently modifies and functionally inactivates parkin," *Nature Med.* 11 (11), 2005. pp. 1214-1221.

(56) References Cited

OTHER PUBLICATIONS

Lee, et al., "Enzymatic and Non-Enzymatic Pathways to Formation of DOPA-Modified PEG Hydrogels," *Polymer Preprints* 42 (2), 2001. pp. 151-152.

Lee, et al., "Synthesis and Gelation of DOPA-Modified Poly(ethylene glycol) Hydrogels," *Biomacromolecules* 3 (2002). pp. 1038-1047.

Lee, et al., "Synthesis of 3,4-dihydroxyphenylalanine (DOPA) containing monomers and their co-polymerizations with PEG-diacrylate to form hydrogels," *J. Biomater. Sci. Polymer Edn*, 15 (4), 2004. pp. 449-464.

Lee, et al., "Biomimetic Adhesive Polymers Based on Mussel Adhesive Proteins," in *Biological Adhesives*, Smith, et al. (eds.), Springer-Verlag: Berlin Heidelberg, 2006. pp. 257-278.

Lee, et al., "Single-Molecule Mechanics of Mussel Adhesion," *Proc. Natl. Acad. Sci. USA*, vol. 103, No. 35 (2006), pp. 12999-13003.

Lee, et al., "Bioadhesive-Based Dosage Forms: The Next Generation," *J. Pharm. Sci.* 89 (7) (2000). pp. 850-866.

Lee, et al., "Hydrogels for Tissue Engineering," *Chem. Rev.*, vol. 101, No. 7 (Jul. 2001), pp. 1869-1879.

Lemieux, et al., "Block and Graft Copolymers and Nanogel™ Copolymer Networks for DNA Delivery into Cell," *J. of Drug Targeting* 8 (2), 2000. pp. 91-105.

Li, et al., "Protein Adsortion on Oligo(ethylene glycol)-Terminated Alkanethiolate Self-Assembled Monolayers: The Molecular Basis for Nonfouling Behavior," *J. Phys. Chem. B* 109 (2005). pp. 2934-2941.

Li, et al., "Copper-Based Metallization for ULSI Applications," *MRS Bulletin* 18 (6), Jun. 1993. pp. 18-21.

Li, et al., "Chemical Modifications of Surface Active Poly(ethylene oxide)—Poly(propylene oxide) Triblock Copolymers," *Bioconj. Chem.* 7 (1996). pp. 592-599.

Li, et al., "Two-Level Antibacterial Coating with Both Release-Killing and Contact-Killing Capabilities," *Langmuir* 22 (24), 2006. pp. 9820-9823.

Long, et al., "A peptide that inhibits hydroxyapatite growth is in an extended conformation on the crystal surface," *Proc. Natl. Acad. Sci. USA* 95 (1998). pp. 12083-12087.

Lorand, et al., "Transglutaminases," *Mol. Cell. Biochem.*, vol. 58 (1984), pp. 9-35.

Love, et al., "Self-Assembled Monolayers of Thiolates on Metals as a Form of Nanotechnology," *Chem. Rev.* 105 (2005). pp. 1103-1169.

Lovich, et al., "Arterial heparin deposition: role of diffusion, convection, and extravascular space," *Am. J. Phsyiol.—Heart C.*, vol. 275 (1998), pp. 2236-2242.

Lu, et al., "Studies on the synthesis and antibacterial activities of polymeric quaternary ammonium salts from dimethylaminoethyl methacrylate," *Reactive & Functional Polymers* 67 (2007). pp. 355-366.

Lucast, "Adhesive considerations for developing stick-to-skin products," *Adhesives Age* 43 (2000). pp. 36, 38-39.

Luo, et al., "Surface-Initiated Photopolymerization of Poly(ethylene glycol) Methyl Ether Methacrylate on a Diethyldithiocarbamate-Mediated Polymer Substrate," *Macromolecules*, vol. 35 (2002), pp. 2487-2493.

Lyman, et al., "Characterization of the formation of interfacially photopolymerized thin hydrogels in contact with arterial tissue," *Biomaterials* 17 (1996). pp. 359-364.

Martin, et al., "Surface Structures of a 4-Chlorocatechol Adsorbed on Titanium Dioxide," *Environ. Sci. Technol.*, vol. 30 (1996), pp. 2535-2542.

Maugh, et al., "Recombinant bioadhesive proteins of marine animals anad their use in adhesive compositions," in Genex Corp. 1988: USA. pp. 196 (1987).

Matyjaszewski, et al., "Atom Transfer Radical Polymerization," *Chem. Rev.* 101 (2001). pp. 2921-2990.

McBride, "Adsorption and Oxidation of Phenolic Compounds by Iron and Manganese Oxides," *Soil Sci. Soc. Am. J.*, vol. 51 (1987), pp. 1466-1472.

McWhitrter, et al., "Siderophore-Mediated Covalent Bonding to Metal (Oxide) Surfaces during Biofilm Initiation by *Pseudomonas aeruginosa* Bacteria," *Langmuir*, vol. 19 (2003), pp. 3575-3577.

Meisel, et al., "Estimation of calcium-binding constants of casein phosphopeptides by capillary zone electrophoresis," *Anal. Chim. Acta* 372 (1998). pp. 291-297.

Mellott, et al., "Release of protein from highly cross-linked hydrogels of poly(ethylene glycol) diacrylate fabricated by UV polymerization," *Biomaterials*, vol. 22 (2001), pp. 929-941.

Merrifield, "Solid Phase Peptide Synthesis. I. The Synthesis of a Tetrapeptide," *J. Am. Chem. Soc.*, vol. 85 (Jul. 20, 1963), pp. 2149-2154.

Merrill, "Distinctions and Correspondences among Surfaces Contacting Blood," *Annals of the NY Acad. Sci.* 516 (1987). pp. 196-203.

Miron, et al., "A Simplified Method for the Preparation of Succinimidyl Carbonate Polyethylene Glycol for Coupling to Proteins," *Bioconj. Chem.* 4 (1993). pp. 568-569.

Morgan, et al., "Biochemical characterisation of polycation-induced cytotoxicity to human vascular endothelial cells," *Journal of Cell Science* 94 (3), 1989,. pp. 553-559.

Morikawa, "Tissue sealing," *Am. J. Surg.*, vol. 182 (2001), pp. 29S-35S.

Mougin, et al., "Construction of Cell-Resistant Surfaces by Immobilization of Poly(ethylene glycol) on Gold," *Langmuir*, vol. 20 (2004), pp. 4302-4305.

Mowery, et al., "Adhesion of Thermally Reversible Gels to Solid Surfaces," *Langmuir*, vol. 13 (1997), pp. 6101-6107.

Mrksich, et al., "Using Self-Assembled Monolayers that Present Oligo(ethylene glycol) Groups to Control the Interactions of Proteins with Surfaces," *American Chemical Society Symposium Series on Chemistry and Biological Applications of Polyethylene Glycol*, vol. 680 (1997), pp. 361-373.

Mukkamala, et al., "Hydrogel Polymers from Alkylthio Acrylates for Biomedical Applications," *Polymer Gels: Fundamentals and Applciations* 833 (2003). pp. 163-174.

Müller, et al., "Interaction of differentiated HL60 cells with poloxamer and poloxamine surface modified model drug carriers," *Eur. J. Phar. Sci.* 5 (1997). pp. 147-153.

Nakagawa, et al., "ENH, Containing PDZ and LIM Domains, Heart/Skeletal Muscle-Specific Protein, Associates with Cytoskeletal Proteins through the PDZ Domain," *Biocehm. Biophys. Res. Commun.* 272 (2000). pp. 505-512.

Nakayama, et al., "Newly Designed Hemostatic Technology Based on Photocurable Gelatin," *ASAIO J.*, vol. 41, No. 3 (1995), pp. M374-M378.

Nakayama, et al., "Photocurable Surgical Tissue Adhesive Glues Composed of Photoreactive Gelatin and Poly(ethylene glycol) Diacrylate," *J. Biomed. Mater. Res.*, vol. 48, Issue 4 (1999), pp. 511-521.

Nakayama, et al., "Development of high-performance stent: gelatinous photogel-coated stent that permits drug delivery and gene transfer," *J. Biomed. Mater. Res.*, vol. 57, Issue 4 (2001), pp. 559-566.

Nakonieczna, et al., "A New Convenient Route for the Synthesis of DOPA Peptides," *Liebigs Annalen der Chemie*, Issue 10 (1994). pp. 1055-1058.

Neff, et al., "A novel method for surface modification to promote cell attachment to hydrophobic substrates," *J. Biomed. Mater. Res.* 40 (1998). pp. 511-519.

Ninan, et al., "Adhesive strength of marine mussel extracts on porcine skin," *Biomaterials* 24 (2003). pp. 4091-4099.

Nishiyama, et al., "Effects of a structural change in collagen upon binding to conditioned dentin studied by $^{13}$C NMR," *J. Biomed. Mater. Res.*, vol. 29 (1995), pp. 107-111.

Nishiyama, et al., "Adhesion mechanisms of resin to etched dentin primed with N-methacryloyl glycine studied by $^{13}$C-NMR," *J. Biomed. Mater. Res.*, vol. 40 (1998). pp. 458-463.

Nishiyama, et al., "Adhesion of N-Methacryloyl-ω-Amino Acid Primers to Collagen Analyzed by $^{13}$C NMR," *J. Dent. Res.*, vol. 80, No. 3 (2001), pp. 855-859.

Northen, et al., "A batch fabricated biomimetic dry adhesive," *Nanotechnology* 16 (8), 2005. pp. 1159-1166.

(56) References Cited

OTHER PUBLICATIONS

Northen, et al., "Meso-scale adhesion testing of integrated micro- and nano-scale structures," *Sensors and Actuators A* 130-131 (2006). pp. 583-587.

Nyström, et al., "Dynamic Light Scattering and Rheological Studies of Thermoreversible Gelation of a Poly(ethylene oxide)-Poly(propylene oxide)-Poly(ethylene oxide) Triblock Copolymer in Aqueous Solution," *Faraday Discuss*. 101 (1995). pp. 335-344.

Nyström, et al., "Dynamic Viscoelasticity of an Aqueous System of a Poly(ethylene oxide)—Poly(propylene oxide)—Poly(ethylene oxide) Triblock Copolymer during Gelation," *J. Phys. Chem*. 100 (1996). pp. 5433-5439.

O'Keefe, et al., "Poloxamer-188 as an Adjunct to Primary Percutaneous Transluminal Coronary Angioplasty for Acute Myocardial Infarction," *Am. J. Cardiol*. 78 (1996). pp. 747-750.

Okino, et al., "In situ hydrogelation of photocurable gelatin and drug release," *J. Biomed. Mater. Res*., vol. 59, Issue 2 (2001), pp. 233-245.

Online Medical Dictionary. "Amino acid." Available from: http://cancerweb.ncl.ac.uk/cgi-bin/omd?query=amino+acid, Date: 1997.

Ono, et al., "Photocrosslinkable chitosan as a biological adhesive," *J. Biomed. Mater. Res*., vol. 49, Issue 2 (1999), pp. 289-295.

Ooka, et al., "Surface-Enhanced Raman Spectroscopy of DOPA-Containing Peptides Related to Adhesive Protein of Marine Mussel, *Mytilus edulis*," *Biopolymers (Biospectroscopy)*, vol. 57, Issue 2 (2000), pp. 92-102.

Orban, et al., "Cytomimetic Biomaterials. 4. In-Situ Photopolymerization of Phospholipids on an Alkylated Surface," *Macromolecules* 33 (2000). pp. 4205-4212.

Ostuni, et al., "A Survey of Structure—Property Relationships of Surfaces that Resist the Adsorption of Protein," *Langmuir* 17 (2001). pp. 5605-5620.

Palmer, et al., "Surfactant Administration Reduces Testicular Ischemia-Reperfusion Injury," *J. Urol*. 159 (1998). pp. 2136-2139.

Papov, et al., "Hydroxyarginine-containing Polyphenolic Proteins in the Adhesive Plaques of the Marine Mussel *Mytilus edulis*," *J. Biol. Chem*. 270 (34) (1995). pp. 20183-20192.

Pardo, et al., "Purification of Adhesive Proteins from Mussels," *Protein Expression and Purif*. 1 (2), 1990. pp. 147-150.

Parsons, "Characteristics of the amino acids as components of a peptide hormone sequence," in *Peptide Hormones*, University Park Press: 1976. pp. 1-7.

Pasche, et al., "Effects of Ionic Strength and Surface Charge on Protein Adsorption at PEGylated Surfaces," *J. Phys. Chem. B* 109 (2005). pp. 17545-17552.

Patel, et al., "Synthesis of Benzyl Esters of α-Amino Acids," *J. Org. Chem*. 30 (1965). pp. 3575-3576.

Peressadko, et al, "When Less is More: Experimental Evidence for Tenacity Enhancement by Division of Contact Area," *J. Adhes*. 80 (2004). pp. 247-261.

Perruchot, et al., "Synthesis of Well-Defined, Polymer-Grafted Silica Particles by Aqueous ATRP," *Langmuir*, vol. 17 (2001), pp. 4479-4481.

Pierpont, et al., "Transition Metal Complexes of o-Benzoquinone, o-Semiquinone, and Catecholate Ligands," *Coord. Chem. Rev*., vol. 38 (1981), pp. 45-87.

Preul, et al., "A Unique Dual-Function Device: A Dural Sealant with Adhesion Prevention Properties," Date: 2006.

Preul, et al., "Use of a Novel Hydrogel Sealant in a Canine Dural Repair Model," Presented at the American Association of Neurological Surgeons; Apr. 2002, Chicago, IL. Available from: http://www.confluentsurgical.com/pdf/ds/Abstract0BNI_PreulAbstract.pdf.

Preul, et al., "Obtaining Watertight Closures of Duraplasty Onlay Grafts in a Craniotomy Preclinical Model," Confluent Surgical, Inc. (2005), 'White Paper.' Available from: http://www.confluentsurgical.com/pdf/LT-6000-034RevA-DuraSeal_duraplasty_study_white_paper.pdf.

Prime, et al., "Adsorption of Proteins onto Surfaces Containing End-Attached Oligo(ethylene oxide): A Model System Using Self-Assembled Monolayers," *J. Am. Chem. Soc*. 115 (1993). pp. 10714-10721.

Prucker, et al., "Polymer Layers through Self-Assembled Monolayers of Initiators," *Langmuir*, vol. 14 (1998), pp. 6893-6898.

Pyun, et al., "Synthesis of Polymer Brushes Using Atom Transfer Radical Polymerization," *Macromol. Rapid. Commun*. 24 (2003). pp. 1043-1059.

Rajh, et al., "Surface Restructuring of Nanoparticles: An Efficient Route for Ligand-Metal Oxide Crosstalk," *J. Phys. Chem. B*, vol. 106 (2002), pp. 10543-10552.

Ramakrishna, et al., "Effect of Particle Size on the Reactivity of Quantum Size ZnO Nanoparticles and Charge-Transfer Dynamics with Adsorbed Catechols," *Langmuir*, vol. 19 (2003), pp. 3006-3012.

Ranger, et al., "Pneumostasis of Experimental Air Leaks with a New Photopolymerized Synthetic Tissue Sealant," *Am. Surg*., vol. 63, Issue 9 (1997), pp. 788-795.

Reed, et al., "A One-Step Synthesis of Monoprotected Polyethylene Glycol Ethers," *J. Org. Chem*., vol. 65 (2000), pp. 5843-5845.

Rodriguez, et al., "Surface Complexation at the $TiO_2$ (anatase)/Aqueous Solution Interface: Chemisorption of Catechol," *J. Colloid Interface Sci*., vol. 177 (1996), pp. 122-131.

Rodriguez-Hernández, et al., "High Branched Poly(L-lysine)," *Biomacromolecules*, vol. 4 (2003), pp. 249-258.

Ross-Murphy, "Rheological Characterization of Polymer Gels and Networks," *Polym. Gels Networks*, vol. 2 (1994), pp. 229-237.

Rozier, et al., Gelrite®: A novel, ion-activated, in situ gelling polymer for ophthalmic vehicles. Effect on bioavailability of timolol, *Int. J. Pharm*. 57 (2), 1989. pp. 163-168.

Ruel-Gariépy, et al., "In situ-forming hydrogels—review of temperature-sensitive systems," *Eur. J. Pharm. Biopharm*. 58 (2004). pp. 409-426.

Ruibal, et al., "The Structure of the Digital Setae of Lizards," *J. Morph*. 117 (1965). pp. 271-294.

Ryu, et al., "A Generalized Approach to the Modification of Solid Surfaces," *Science* 308 (2005). pp. 236-239.

Rzepecki, et al., "α,β-Dehydro-3,4-dihydroxyphenylalanine Derivatives: Potential Schlerozation Intermediates in Natural Composite Materials," *Arch. Biochem. Biophys*. 285 (1) (1991). pp. 17-26.

Rzepecki, et al., "Wresting the muscle from mussel beards: research and applications," *Mol. Mar. Biol. Biotech*. 4 (4) (1995). pp. 313-322.

Rzepecki, et al., "Bioadhesives: DOPA and Phenolic proteins as components of organic composite materials", *Principles of Cell Adhesion*, P.D. Richardson and M. Steiner (eds.), CRC Press, Boca Raton, FL. (1995). pp. 107-142142.

Saby, et al., "*Mytilus edulis* Adhesive Protein (MAP) as an Enzyme Immobilization Matrix in the Fabrication of Enzyme-Based Electrodes," *Electroanalysis* 10 (17) (1998). pp. 1193-1199.

Sanborn, et al., "In situ crosslinking of a biomimetic peptide-PEG hydrogel via thermally triggered activation of factor XIII," *Biomaterials*, vol. 23 (2002), pp. 2703-2710.

Sawada, et al., "Micropatterning of Copper on a Poly(ethylene terephthalate) Substrate Modified with a Self-Assembled Monolayer," *Langmuir* 22 (2006). pp. 332-337.

Sawhney, et al., "Interfacial photopolymerization of poly(ethylene glycol)-based hydrogels upon alginate-poly(l-lysine) microcapsules for enhanced biocompatibility," *Biomaterials*, vol. 14, No. 13 (1993), pp. 1008-1016.

Sawhney, et al., "Bioerodible Hydrogels Based on Photopolymerized Poly(ethylene glycol)-*co*-poly(α-hydroxy acid) Diacrylate Macromers," *Macromolecules*, vol. 26 (1993), pp. 581-587.

Schmolka, "Articifial Skin. I. Preparation and Properties of Pluronic F-127 Gels for Treatment of Burns," *J. Biomed. Mater. Res*. 6 (6) (1972). pp. 571-582.

Schnurrer, et al., "Mucoadhesive properties of the mussel adhesive protein," *Int. J. Pharm*. 141 (1996). pp. 251-256.

Sever, et al., "Synthesis of peptides containing DOPA (3,4-dihydroxyphenylalanine)," *Tetrahedron* 57 (2001). pp. 6139-6146.

Sever, et al., "Metal-Mediated Cross-Linking in the Generation of a Marine-Mussel Adhesive," *Angew. Chem. Int. Ed*., vol. 43 (2004), pp. 448-450.

Shull, et al., "Fracture Mechanics Studies of Adhesion in Biological Systems," *Interface Sci*., vol. 8 (2000), pp. 95-110.

Shull, "Contact mechanics and the adhesion of soft solids," *Mater. Sci. Eng., R* 36 (2002). pp. 1-45.

(56) References Cited

OTHER PUBLICATIONS

Sichel, et al., "Relationship Between Melanin Content and Superoxide Dismutase (SOD) Activity in the Liver of Various Species of Animals," *Cell Biochem. Funct.* 5 (1987). pp. 123-128.
Sierra, "Fibrin Sealant Adhesive Systems: A Review of Their Chemistry, Material Properties and Clinical Applications," *J. Biomed. Appl.*, vol. 7 (1993), pp. 309-352.
Sitti, et al., "Synthetic Gecko Foot-Hair Micro/Nano-Structures as Dry Adhesives," *J. Adhes. Sci. Technol.*, vol. 17, No. 8 (2003), pp. 1055-1073. Available from: http://nanolab.me.cmu.edu/publications/papers/Sitti-JAST2003.pdf.
Skelhorne, et al., "Hydrogel Adhesives for Wound-Care Applications," *Medical Device Technology* (Nov. 2002). pp. 19-23.
Soriaga, et al., "Determination of the Orientation of Adsorbed Molecules at Solid-Liquid Interfaces by Thin-Layer Electrochemistry: Aromatic Compounds at Platinum Electrodes," *J. Am. Chem. Soc.* 104 (1982). pp. 2735-2742.
Sousa, et al., "Human Serum Albumin Adsorption on $TiO_2$ from Single Protein Solutions and from Plasma," *Langmuir*, vol. 20 (2004), pp. 9745-9754.
Sperinde, et al., "Synthesis and Characterization of Enzymatically-Cross-Linked Poly(ethylene glycol) Hydrogels," *Macromolecules* 30 (18) (1997). pp. 5255-5264.
Sperinde, et al., "Control and Prediction of Gelation Kinetics in Enzymatically Cross-Linked Poly(ethylene glycol) Hydrogels," *Macromolecules* 33 (2000). pp. 5476-5480.
Spolenak, et al., "Adhesion design maps for bio-inspired attachment systems," *Acta. Biomater.* 1 (2005). pp. 5-13.
Spotnitz, "History of Tissue Adhesives." In: Sierra, et al. (eds.), *Surgical Adhesives and Sealants: Current Technology and Applications*. Technomic Publishing Company, Inc.: Lancaster, PA (1997). pp. 3-11.
Spotnitz, "Commercial fibrin sealants in surgical care," *Am. J. Surg.* 182 (2001). pp. 8S-14S.
Statz, et al., "New Peptidomimetic Polymers for Antifouling Surfaces," *J. Am. Chem. Soc.*, vol. 127, No. 22 (2005), pp. 7972-7973.
Stevens, "Trace bio-organic constituents of gelatins—a review," *Food Australia*, vol. 44, No. 7 (1992), pp. 320-324.
Stile, et al., "Sequential robust design methodology and X-ray photoelectron spectroscopy to analyze the grafting of hyaluronic acid to glass substrates," *J. Biomed. Mater Res.*, vol. 61, Issue 3 (2002), pp. 391-398.
Stiles, et al., "Axisymmetric Adhesion Test to Examine the Interfacial Interactions between Biologically-Modified Networks and Models of the Extracellular Matrix," *Langmuir*, vol. 19 (2003), pp. 1853-1860.
Strausberg, et al., "Protein-based medical adhesives," *Trends in Biotechnology* 8 (2) (1990). pp. 53-57.
Strausberg, et al., "Development of a microbial system for production of mussel adhesive protein." In: *Adhesives from Renewable Resources*. Hemingway, et al. (eds.), ACS Symposium Series 385, American Chemical Society, Washington, D.C. (1989). pp. 453-464.
Sugumaran, et al., "Chemical- and Cuticular Phenoloxidase-Mediated Synthesis of Cysteinyl-Catechol Adducts," *Arch. Insect Biochem. Physiol.* 11 (2) (1989). pp. 127-137.
Sugumaran, "Unified Mechanism for Sclerotization of Insect Cuticle," *Adv. Insect. Physiol.*, vol. 27 (1998), pp. 229-334.
Sun, et al., "Improved antifouling property of zwitterionic ultrafiltration membrane composed of acrylonitrile and sulfobetaine copolymer," *J. of Memr. Sci.* 285 (2006). pp. 299-305.
Sun, et al., "The Nature of the Gecko Lizard Adhesive Force," *Biophys. J.* 89 (2005). pp. L14-L16.
Swerdloff, et al., "Solid phase synthesis of bioadhesive analogue peptides with trifluoromethanesulfonic acid cleavage from PAM resin," *Int. J. Peptide Protein Res.*, vol. 33 (1989), pp. 318-327.
Tae, et al., "Sustained release of human growth hormone from in situ forming hydrogels using self-assembly of fluoroalkyl-ended poly(ethylene glycol)," *Biomaterials*, vol. 26 (2005), pp. 5259-5266.
Taira, et al., "Analysis of Photo-iniators in Visible-light-cured Dental Composite Resins," *J. Dent. Res.*, vol. 67, No. 1 (1988), pp. 24-28.
Tan, et al., "Surface modification of nanoparticles by PEO/PPO block copolymers to minimize interactions with blood components and prolong blood circulation in rats," *Biomaterials*, vol. 14, No. 11 (1993), pp. 823-833.
Tatehata, et al., "Model Polypeptide of Mussel Adhesive Protein. I. Synthesis and Adhesive Studies of Sequential Polypeptides (X-Tyr-Lys)$_n$ and (Y-Lys)$_n$," *J. Appl. Polym. Sci.*, vol. 76, No. 6 (2000), pp. 929-937.
Taylor, et al., "Polargraphic and Spectrophotometric Investigation of Iron(III) Complexation to 3,4-Dihydroxyphenylalanine-Containing Peptides and Proteins from *Mytilus edulis*," *Inorg. Chem.*, vol. 33 (1994), pp. 5819-5824.
Taylor, et al., "*trans*-2,3-*cis*-3,4-Dihydroxyproline, a New Naturally Occurring Amino Acid, Is the Sixth Residue in the Tandemly Repeated Consensus Decapeptides of an Adhesive Protein from *Mytilus edulis*," *J. Am. Chem. Soc.*, vol. 116 (1994), pp. 10803-10804.
Taylor, et al., "Ferric Ion Complexes of a DOPA-Containing Adhesive Protein from *Mytilus edulis*," *Inorg. Chem.*, vol. 35 (1996), pp. 7572-7577.
Uyama, et al., "Surface Modification of Polymers by Grafting," *Advances in Polymer Science*, vol. 137 (1998), pp. 1-39.
Venkatraman, et al., "Skin adhesives and skin adhesion. 1. Transdermal drug delivery systems," *Biomaterials*, vol. 19 (1998), pp. 1119-1136.
Vörös, et al., "Optical grating coupler biosensors," *Biomaterials*, vol. 23 (2002), pp. 3699-3710.
Waite, "Evidence for a Repeating 3,4-Dihydroxyphenylalanine- and Hydroxyproline-containing Decapeptide in the Adhesive Protein of the Mussel, *Mytilus edulis* L.," *J. Biol. Chem.*, vol. 258, No. 5 (1983), pp. 2911-2915.
Waite, et al., "Assay of Dihdroxyphenylalanine (Dopa) in Invertebrate Structural Proteins," *Methods Enzymol.*, vol. 107 (1984), pp. 397-413.
Waite, "Adhesion à la Moule," *Integr. Comp. Biol.*, vol. 42 (2002), pp. 1172-1180.
Waite, "Mussel Beards: A Coming of Age" *Chem. Ind.* (Sep. 2, 1991), pp. 607-611.
Waite, "Nature's underwater adhesive specialist," *Int. J. Adhes. Adhes.*, vol. 7, No. 1 (1987), pp. 9-14.
Waite, "Nature's underwater adhesive specialist," *Chemtech*, vol. 17 (1987), pp. 692-697.
Waite, et al., "3,4-Dihydroxyphenylalanine in an Insoluble Shell Protein of *Mytilus edulis*," *Biochem. Biophys. Acta*, vol. 541 (1978), pp. 107-114.
Waite, et al., "Polyphosphoprotein from the Adhesive Pads of *Mytilus edulis*," *Biochemistry*, vol. 40 (2001), pp. 2887-2893.
Waite, et al., "The Bioadhesive of *Mytilus byssus*: A Protein Containing L-DOPA," *Biochem. & Biophy. Res. Comm.*, vol. 96, No. 4 (1980), pp. 1554-1561.
Waite, et al., "Mussel Adhesion: Finding the Tricks Worth Mimicking," *J. Adhes.*, vol. 81 (2005), pp. 297-317.
Waite, et al., "Polyphenolic Substance of *Mytilus edulis*: Novel Adhesive Containing L-Dope and Hydroxyproline," *Science*, vol. 212, No. 4498 (1981), pp. 1038-1040.
Waite, "Precursors of Quinone Tanning: Dopa-Containing Proteins," *Methods Enzymol.*, vol. 258 (1995), pp. 1-21.
Wang, et al., "Facile synthesis of well-defined water-soluble polymers via atom transfer radical polymerization in aqueous media at ambient temperature," *Chem. Commun.* (1999), pp. 1817-1818.
Wang, et al., "Facile Atom Transfer Radical Polymerization of Methoxy-Capped Oligo(ethylene glycol) Methacrylate in Aqueous Media at Ambient Temperature," *Macromolecules*, vol. 33 (2000), pp. 6640-6647.
Wanka, et al., "The aggregation behavior of poly-(oxyethylene)-poly-(oxypropylene)-poly-(oxyethylene)-block-copolymers in aqueous solution," *Cooloid. Polym. Sci.*, vol. 268 (1990), pp. 101-117.
Warner, et al., "Expression of multiple forms of an adhesive plaque protein in an individual mussel, *Mytilus edulis*," *Mar. Biol.*, vol. 134 (1999), pp. 729-734.

(56) References Cited

OTHER PUBLICATIONS

Watanabe, et al., "Bonding durability of photocured phenyl-P in TEGDMA to smear layer-retained bovine dentin," *Quint. Int.*, vol. 24, No. 5 (1993), pp. 335-342.

Webber, et al., "Effects of geometric confinement on the adhesive debonding of soft elastic solids," *Phys. Rev. E*, vol. 68 (2003), pp. 021805-1-to-021805-11.

Whitesides, "The origins and the future of microfluidics," *Nature*, vol. 442 (2006), pp. 368-373.

Wisniewski, et al., "Methods for reducing biosensor membrane biofouling," *Colloids Surf., B*, vol. 18 (2000), pp. 197-219.

Yamada, "Chitosan Based Water-Resistant Adhesive. Analogy to Mussel Glue," *Biomacromolecules*, vol. 1 (2000), pp. 252-258.

Yamamoto, "Marine Adhesive Proteins and Some Biotechnological Applications," *Biotechnol. Genet. Eng. Rev.*, vol. 13 (1996), pp. 133-165.

Yamamoto, "Adhesive studies of synthetic polypeptides: A model for marine adhesive proteins," *J. Adhesion Sci. Tech.*, vol. 1, No. 2 (1987), pp. 177-183.

Yamamoto, "Synthesis and Adhesive Studies of Marine Polypeptides," *J. Chem. Soc. Perkin Trans.*, vol. 1 (1987), pp. 613-618.

Yamamoto, "Insolubilizing and adhesive studies of water-soluble synthetic model proteins," *Int. J. Biol. Macromol.*, vol. 12 (1990), pp. 305-310.

Yamamoto, et al., "Synthesis and Adhesives of Marine Adhesive Proteins of the Chilean Mussel *Aula comya ater*," *Biomimetics*, vol. 1, No. 3 (1992), pp. 219-238.

Yamamoto, et al., "Work of Adhesion of Synthetic Polypeptides Containing L-Lysine," *J. Colloid Interface Sci.*, vol. 156 (1993), pp. 515-517.

Yamamoto, et al., "Wettability and Adhesion of Synthetic Marine Adhesive Proteins and Related Model Compounds," *J. Colloid Interface Sci.*, vol. 176 (1995), pp. 111-116.

Yang, et al., "Physicochemical aspects of drug delivery and release from polymer-based colloids," *Curr. Opin. Colloid Interface Sci.*, vol. 5 (2000), pp. 132-143.

Young, et al., "Marine Animals and Adhesion." In: Allen (ed.), *Adhesion 6*. Applied Science Publishers: London and New Jersey, 1982. pp. 19-39.

Yu, et al., "Micellisation and Gelation of Triblock Copoly(oxyethylene/oxypropylene/oxyethylene), F127," *J. Chem. Soc., Faraday Trans.*, vol. 88, No. 17 (1992), pp. 2537-2544.

Yu, et al., "Synthetic Polypeptide Mimics of Marine Adhesives," *Macromolecules*, vol. 31 (1998), pp. 4739-4745.

Yu, et al., "Role of L-3,4-Dihydroxyphenylalanine in Mussel Adhesive Proteins," *J. Am. Chem. Soc.*, vol. 121 (1999), pp. 5825-5826.

Yurdumakan, et al., "Synthetic gecko foot-hairs from multiwalled carbon nanotubes," *Chem. Commun.*, vol. 30 (2005), pp. 3799-3801.

Zekorn, et al., "Biocompatibility and immunology in the encapsulation of islets of Langerhans (bioartificial pancreas)," *Int. J. Artif. Organs*, vol. 19, No. 4 (1996), pp. 251-257.

Zeng, et al., "Synthesis and Characterization of DOPA-PEG Conjugates," *Polymer Preprints*, vol. 41, No. 1 (2000), pp. 989-990.

Zhan, et al., "Functionalization of Nano-Faujasite Zeolite with PEG-Grafted PMA Tethers Using Atom Transfer Radical Polymerization," *Macromolecules*, vol. 37 (2004), pp. 2748-2753.

Zhao, et al., "Polymer brushes: surface-immobilized macromolecules," *Prog. Polym. Sci.*, vol. 25 (2000), pp. 677-710.

Zuckermann, et al., "Efficient Method for the Preparation of Peptoids [Oligo(N-substituted glycines)] by Submonomer Solid-Phase Synthesis," *J. Am. Chem. Soc.*, vol. 114 (1992), pp. 10646-10647.

\* cited by examiner

C-(PEG-DOPA₃-Lys₂)₄
PEG 10K – (DL)₄

(c)

C-(PEG-DOHA)₄
(d) PEG 10K – (DH)₄ m=56
(g) PEG 20K – (DH)₄ m=113

C-(PEG-DMu)₄
PEG 10K – (DMu)₄
(e)

C-(PEG-DMe)₄
PEG 10K – (DMe)₄
(f)

DOPA-FUNCTIONALIZED, BRANCHED, POLY(AKLYLENE OXIDE) ADHESIVES

CROSS REFERENCE TO RELATED APPLICATIONS

This application claims benefit of U.S. Provisional Ser. No. 60/910,683 filed on Apr. 9, 2007, entitled "DOPA-Functionalized, Branched, Poly(ethylene-Glycol) Adhesives", by Sean A. Burke, Jeffrey L. Dalsin, Bruce P. Lee and Phillip B. Messersmith the contents of which are incorporated in their entirety herein by reference.

REFERENCE TO FEDERAL FUNDING

This invention was made with government support under Grant Number RO1DEO14193, awarded by the National Institutes of Health. The government has certain rights in the invention.

FIELD OF THE INVENTION

The invention relates generally to new synthetic medical adhesives which exploit the key components of natural marine mussel adhesive proteins. The method exploits a biological strategy to modify surfaces that exhibit adhesive properties useful in a diverse array of medical applications. Specifically, the invention describes the use of peptides that mimic natural adhesive proteins in their composition and adhesive properties. These adhesive moieties are coupled to a polymer chain, and provide adhesive and crosslinking cohesive properties to the synthetic polymer.

BACKGROUND OF THE INVENTION

Mussel adhesive proteins (MAPs) are remarkable underwater adhesive materials secreted by certain marine organisms which form tenacious bonds to the substrates upon which they reside. During the process of attachment to a substrate, MAPs are secreted as adhesive fluid precursors that undergo a crosslinking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives.

In the medical arena, few adhesives exist which provide both robust adhesion in a wet environment and suitable mechanical properties to be used as a tissue adhesive or sealant. For example, fibrin-based tissue sealants (e.g., Tisseel VH™, Baxter Healthcare) provide a good mechanical match for natural tissue, but possess poor tissue-adhesion characteristics. Conversely, cyanoacrylate adhesives (e.g., Dermabond™, ETHICON, Inc.) produce strong adhesive bonds with surfaces, but tend to be stiff and brittle in regard to mechanical properties and tend to release formaldehyde as they degrade.

Therefore, a need exists for new synthetic medical adhesive materials that overcome one or more of these current disadvantages.

BRIEF SUMMARY OF THE INVENTION

The present invention surprisingly provides a multi-armed, poly(alkylene oxide)polyether, multihydroxy(dihydroxy) phenyl derivative (DHPD) having the general formula:

$$\text{CA-}[\text{Z-PA-}(L)_a\text{-}(DHPD)_b\text{-}(AA)_c\text{-PG}]_n \quad (II)$$

wherein
CA is a central atom that is carbon;
each Z, independently, is a C1 to a C6 linear or branched, substituted or unsubstituted alkyl group or a bond;
each PA, independently, is a substantially poly(alkylene oxide)polyether or derivative thereof;
each L, independently, optionally, is a linker or is a linking group selected from amide, ester, urea, carbonate or urethane linking groups;
each DHPD, independently, is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value of 4.

Such materials are useful as adhesives, and more specifically, medical adhesives that can be utilized as sealants for wound repair.

The adhesives of the invention can be utilized for wound closure and materials of this type are often referred to as tissue sealants or surgical adhesives.

In one aspect, CA is a carbon atom, each Z is a methylene, each PA is a polyethylene oxide polyether that is a polyethylene oxide (PEG), the linking group is an amide, ester, urea, carbonate or urethane, the DHDP is dopamine, 3,4-dihydroxyphenylalanine, 3,4-dihydroxyphenyl ethanol or 3,4-dihydroxyhydrocinnamic acid (or combinations thereof) and each AA is lysine. The molecular weight of each PEG is between about 1,250 and about 12,500 daltons, in particular between about 2,500 and about 5,000 daltons. In particular, the linking group is an amide, urethane or ester.

In another aspect, CA is a carbon atom, each Z is a methylene, each PA is a polyethylene oxide polyether that is a polyethylene oxide (PEG), the linking group is an amide, ester, urea, carbonate or urethane, the DHDP is dopamine, 3,4-dihydroxyphenylalanine, 3,4-dihydroxyphenyl ethanol or 3,4-dihydroxyhydrocinnamic acid (or combinations thereof) and the PG is either a tert-butoxycarbonyl ("Boc") or a hydrogen atom. The molecular weight of each PEG is between about 1,250 and about 12,500 daltons, in particular between about 2,500 and about 5,000 daltons. In particular, the linking group is an amide, urethane or ester.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
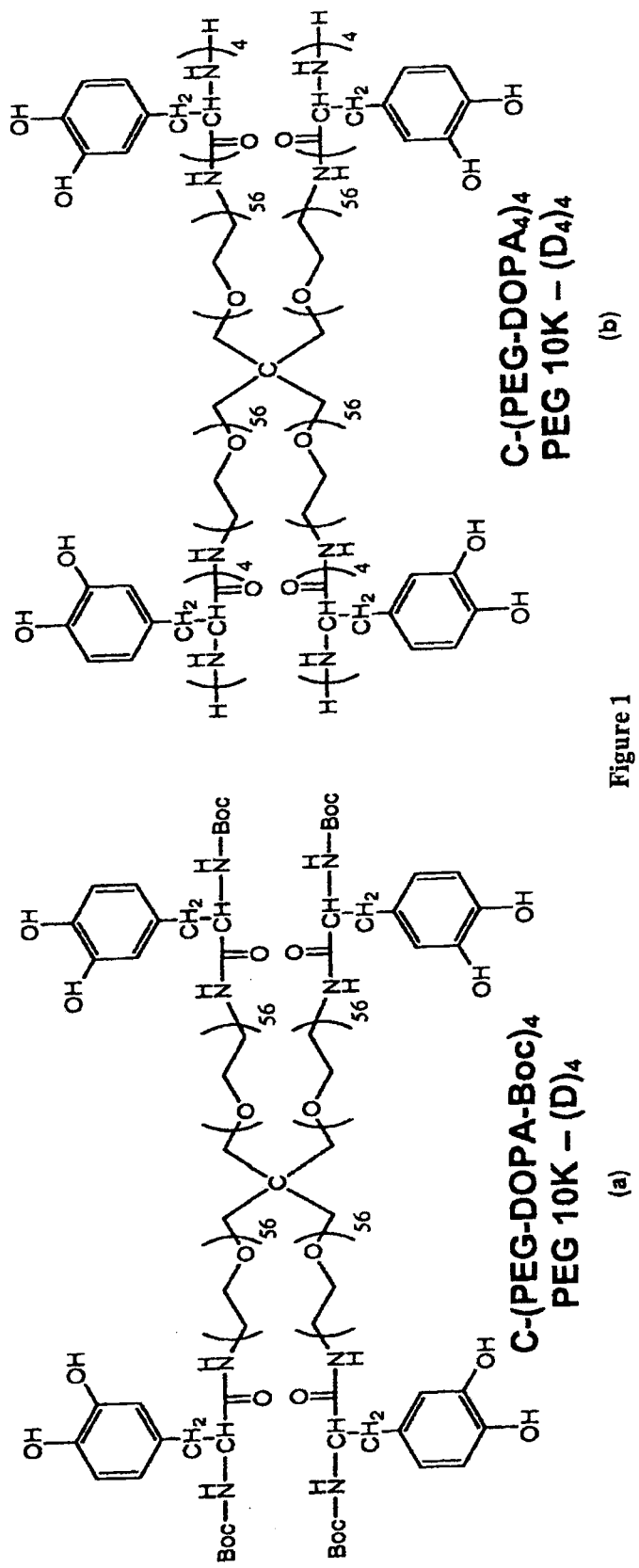
FIGS. 1(a)-(g) depicts novel synthetic liquid adhesives are comprised of branched or armed poly(ethylene glycols) end functionalized with DOPA-based amino acids and short peptides of this invention. The unique catechol side chains provide both adhesive and cohesive properties to these polymers.
FIG. 1(h) shows, schematically a possible reaction sequence to obtain the cured adhesive. Also shown in FIGS. 1e and 1f are exemplary molecular structures referred to as C-(PEG-DMu)$_4$ and C-(PEG-DMe)$_4$. These later structures illustrate an embodiment of this invention in which linking groups, specifically, urethane and ester linking groups, are introduced into or incorporated into the "arms" to control or adjust e.g., their biodegradability, cost effectiveness of synthesis or other properties.
Figure 1:
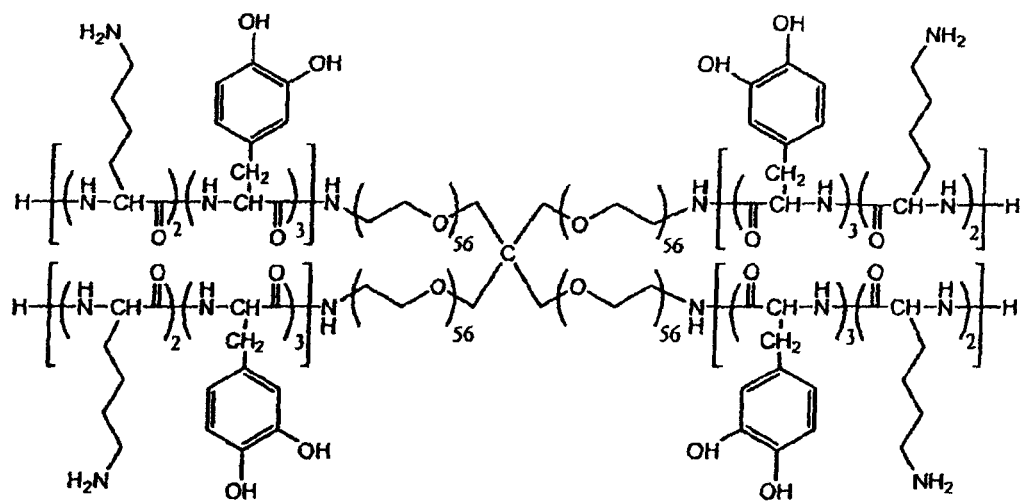
Figure 1:
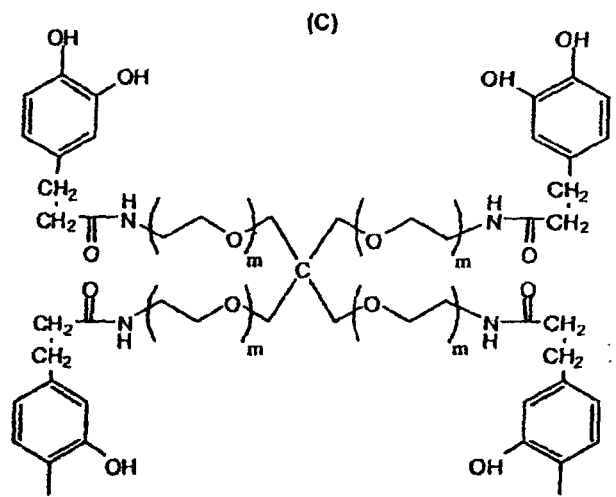
Figure 1:
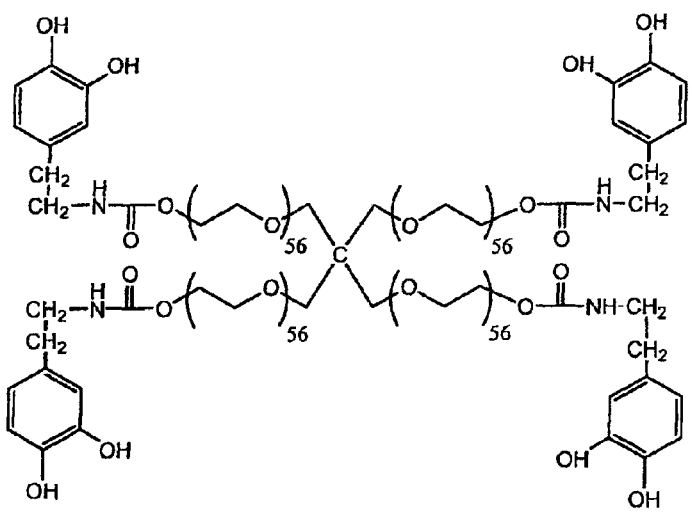
Figure 1:
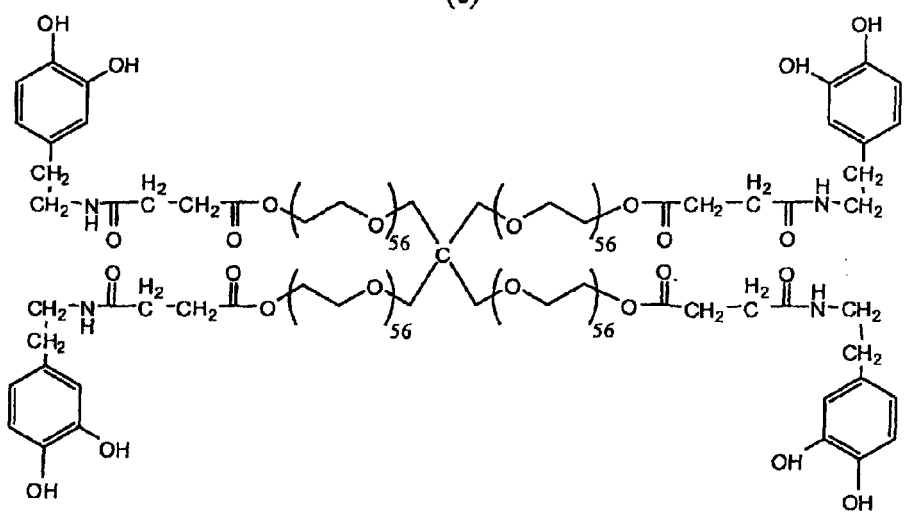
Figure 1:
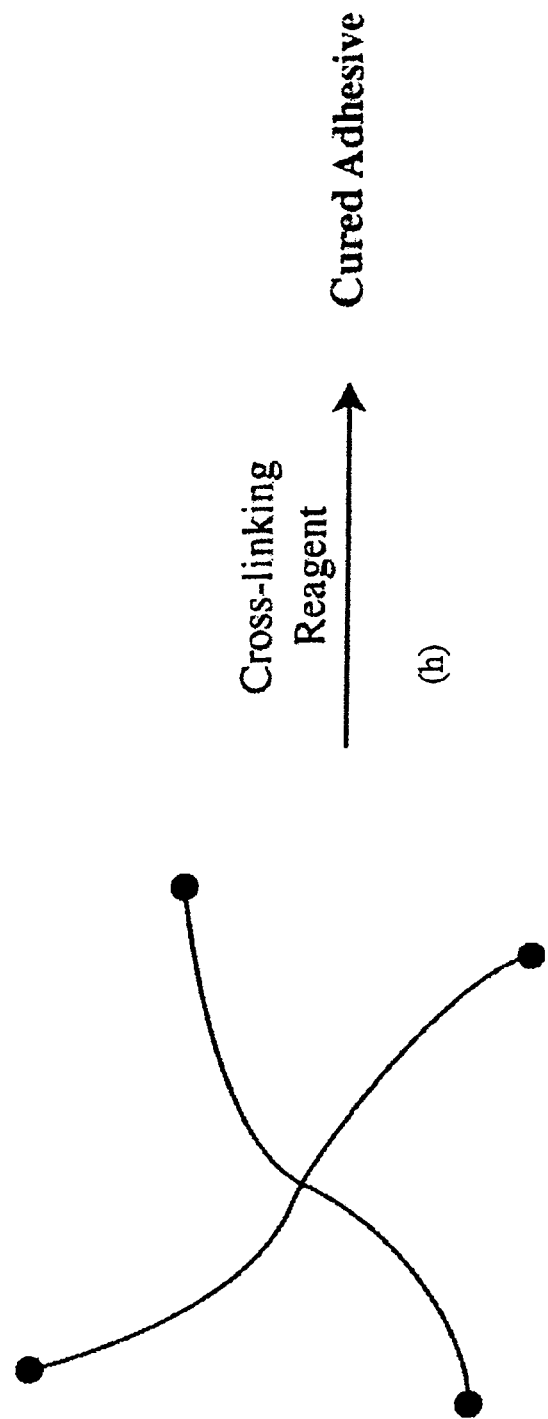
Figure 2:
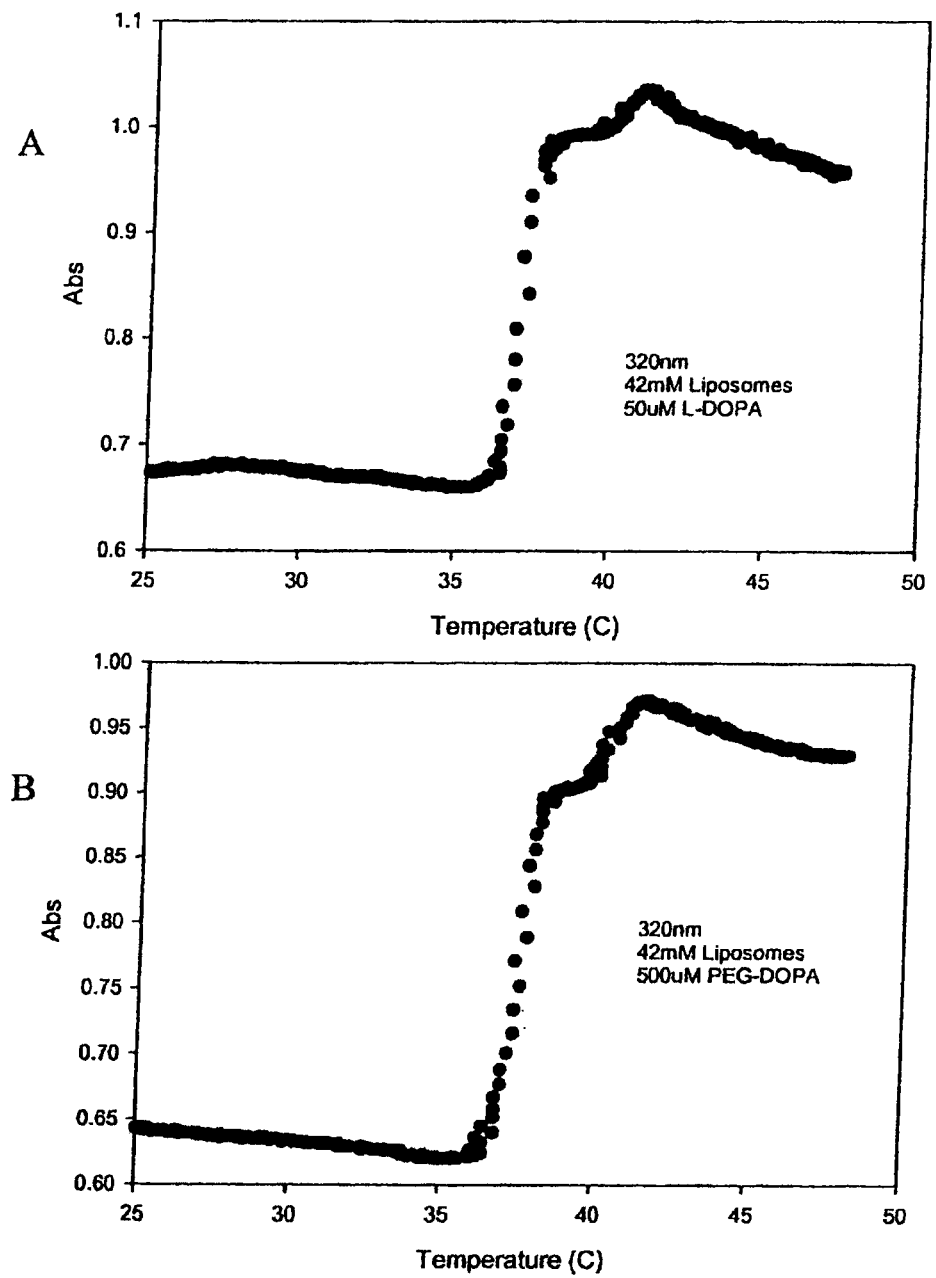
FIG. 2 depicts temperature-dependent release of liposomally encapsulated NaIO$_4$, and subsequent oxidation of L-DOPA (A) and C-(PEG-DOPA-Boc)$_4$ (B).
Figure 3:
FIG. 3 depicts, schematically, a lap-shear tensile test arrangement used to test adhesion.
Figure 4:
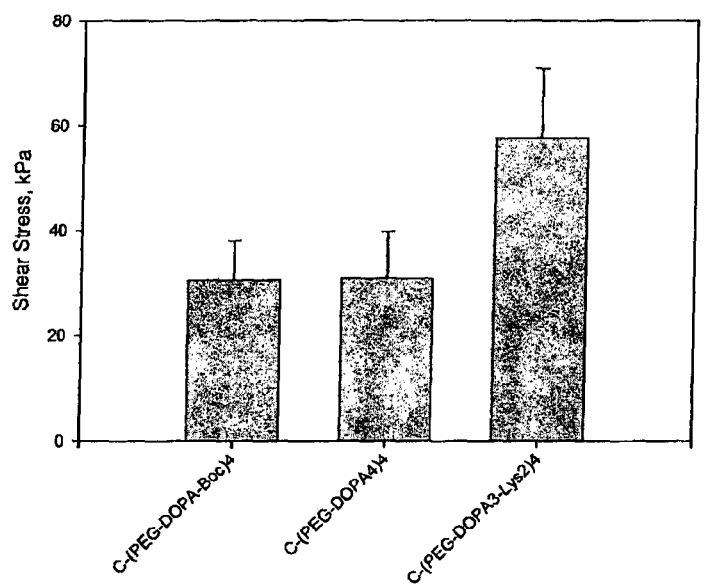
FIG. 4 depicts lap-shear tensile stress of branched PEG-DOPA liquid adhesive on titanium surfaces.
Figure 5:
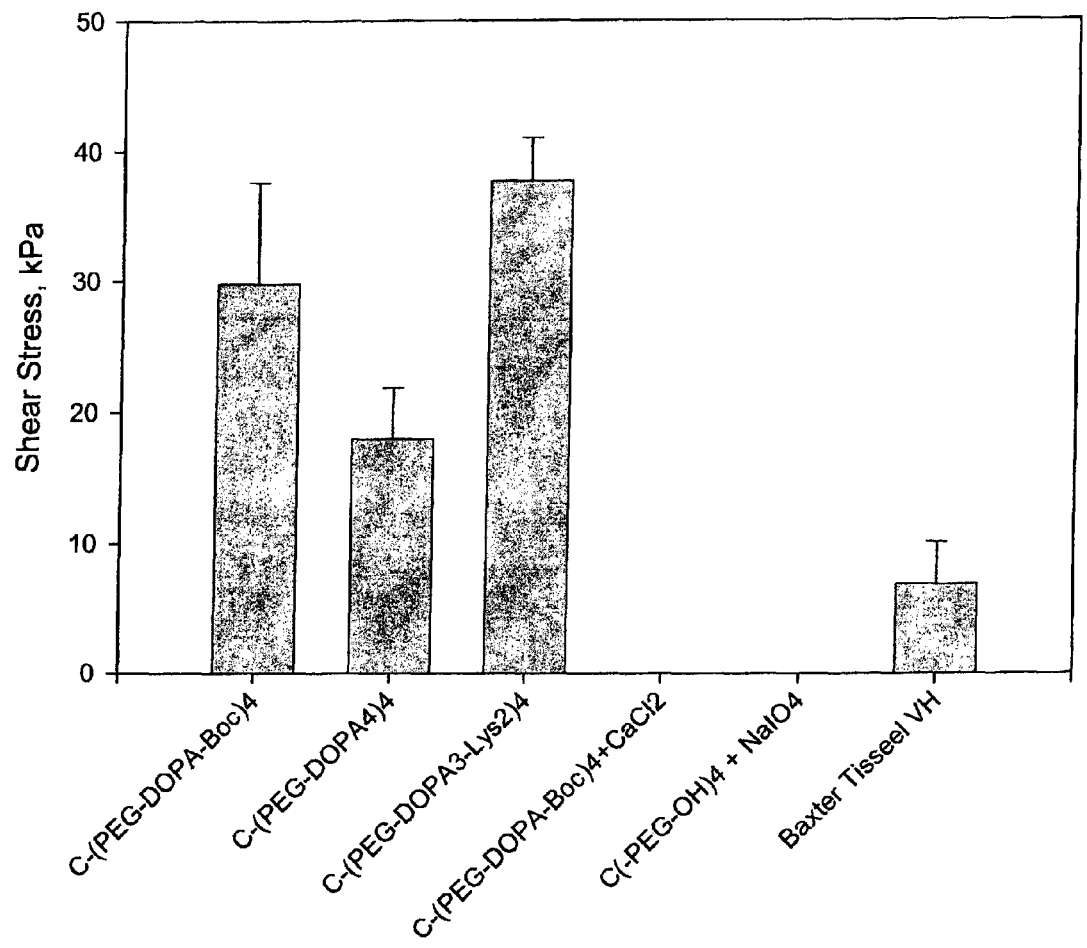
FIG. 5 depicts lap-shear tensile stress of branched PEG-DOPA liquid adhesives on porcine dermal tissue. Shear stress was also compared to Tisseel VH™ (Baxter Healthcare).
Figure 6:
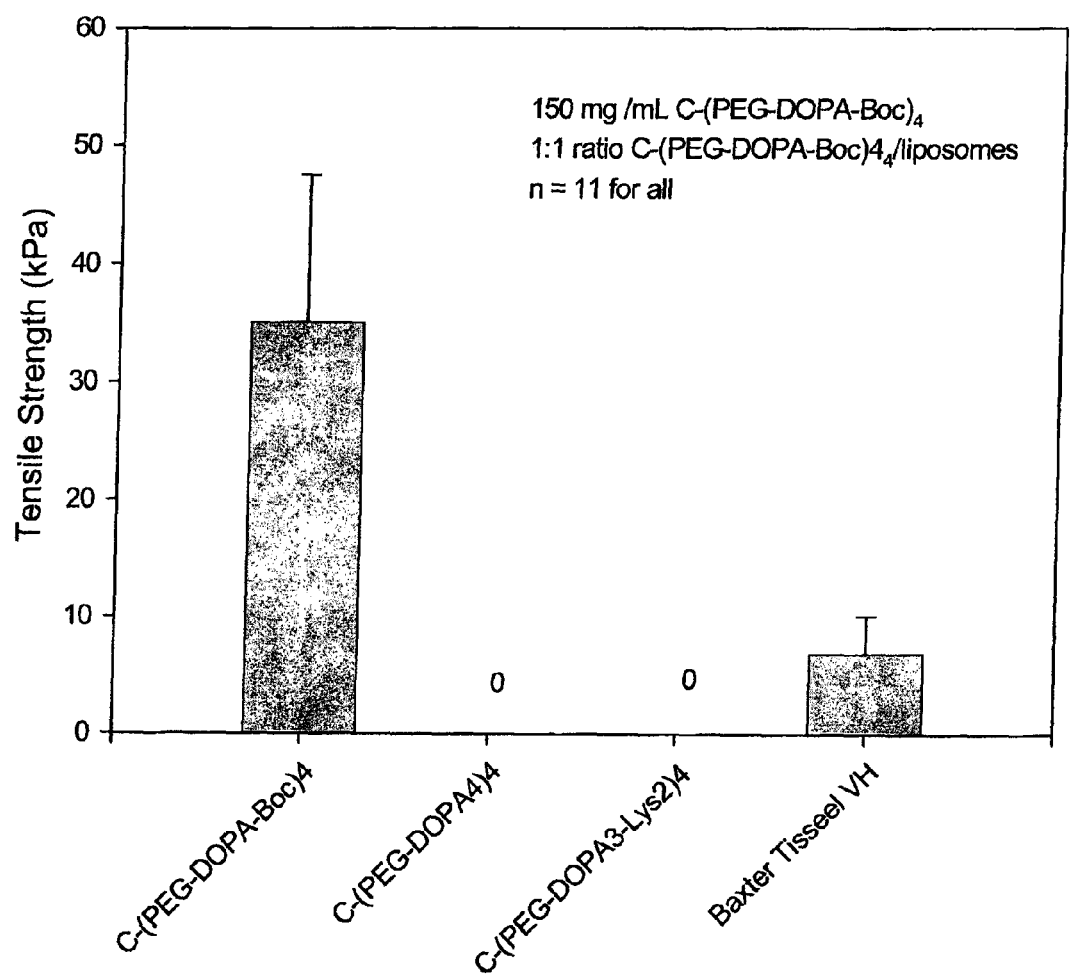
FIG. 6 depicts lap-shear tensile stress of branched C-(PEG-DOPA-Boc)$_4$/IFV—NaIO$_4$ liquid adhesives on porcine dermal tissue. Shear stress was also compared to Tisseel VH™ (Baxter Healthcare).

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention surprisingly provides a multi-armed, poly(alkylene oxide)polyether, multihydroxy(dihydroxy)phenyl derivative (DHPD) having the general formula:

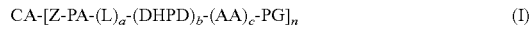

$$\text{CA-[Z-PA-(L)}_a\text{-(DHPD)}_b\text{-(AA)}_c\text{-PG]}_n \qquad (I)$$

wherein

CA is a central atom selected from carbon, oxygen, sulfur, nitrogen, or a secondary amine, most particularly a carbon atom;

each Z, independently, is a C1 to a C6 linear or branched, substituted or unsubstituted alkyl group or a bond;

each PA, independently, is a substantially poly(alkylene oxide)polyether or derivative thereof;

each L, independently, optionally, is a linker or is a linking group selected from amide, ester, urea, carbonate or urethane linking groups;

each DHPD, independently, is a multihydroxy phenyl derivative;

each AA, independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker "b" has a value of one or more;

"c" has a value in the range of from 0 to about 20; and

"n" has a value from 3 to 15.

Such materials are useful as adhesives, and more specifically, medical adhesives that can be utilized as sealants.

The identifier "CA" refers to a central atom, a central point from which branching occurs, that can be carbon, oxygen, sulfur, a nitrogen atom or a secondary amine. It should be understood therefore, that when carbon is a central atom, that the central point is quaternary having a four armed branch. However, each of the four arms can be subsequently further branched. For example, the central carbon could be the pivotal point of a moiety such as 2,2-dimethylpentane, wherein each of the methylenes attached to the quaternary carbon could each form 3 branches for an ultimate total of 12 branches, to which then are attached one or more PA(s) defined herein below. An exemplary CA containing molecule is pentaerythritol, C(CH$_2$OH)$_4$.

Likewise, oxygen and sulfur can serve as the central atom. Both of these heteroatoms can then further be linked to, for example, a methylene or ethylene that is branched, forming multiple arms therefrom and to which are then attached one or more PA(s).

When the central atom is nitrogen, branching would occur so that at least 3 arms would form from the central nitrogen. However, each arm can be further branched depending on functionality linked to the nitrogen atom. As above, if the moiety is an ethylene, the ethylene group can serve as additional points of attachment (up to 5 points per ethylene) to which are then attached one or more PA(s). Hence, it is possible that a molecule where the central atom is nitrogen could have up to 15 branches starting therefrom, wherein 3 fully substituted ethylene moieties are attached to the central nitrogen atom.

Where the central atom is a secondary amine,

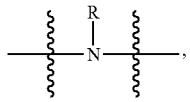

R can be a hydrogen atom or a substituted or unsubstituted, branched or unbranched alkyl group. The remaining sites on the amine then would serve as points of attachment for at least 2 arms. Again, each arm can be further branched depending on the functionality linked to the nitrogen atom. As above, if the moiety is an ethylene, the ethylene group can serve as additional points of attachment (up to 5 points per ethylene) to which are then attached one or more PA(s). Hence, it is possible that a molecule where the central atom is a secondary amine, could have up to 10 branches emanating therefrom, wherein 2 fully substituted ethylene moieties are attached to the central nitrogen atom.

In particular, the central atom is a carbon atom that is attached to four PAs as defined herein.

It should be understood that the central atom (CA) can be part of a PA as further defined herein. In particular, the CA can be either a carbon or an oxygen atom when part of the PA.

The compound can include a spacer group, Z, that joins the central atom (CA) to the PA. Suitable spacer groups include C1 to C6 linear or branched, substituted or unsubstituted alkyl groups. In one embodiment, Z is a methylene (—$CH_2$—, ethylene —$CH_2CH_2$— or propene —$CH_2CH_2CH_2$—). Alternatively, the spacer group can be a bond formed between the central atom and a terminal portion of a PA.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, e.g., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl", "alkenyl", and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl", by itself or as part of another substituent, refers to a saturated, branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl," by itself or as part of another substituent, refers to an unsaturated, branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl(methano); ethan-1,2-diyl(ethano); propan-1,3-diyl(propano); butan-1,4-diyl(butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^b C(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)O^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms, e.g., N, O, S, P, etc. and of functional groups, e.g., —COOH, —$NH_2$, —SH, as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, or of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—($CH_2$—$CH(CH_3)$—O)$_{xx}$—$CH_2$—$CH(CH_3)$—$NH_2$, where xx is 0 to about 3, e.g., PEG-O—($CH_2$—CH($CH_3$)—O)$_{xx}$—$CH_2$—$CH(CH_3)$—$NH_2$ and a PA with an acid end-group typically has a structure of PA-O—$CH_2$—COOH, e.g., PEG-O—$CH_2$—COOH. These are all contemplated as being within the scope of the invention and should not be considered limiting.

Generally each PA of the molecule has a molecular weight between about 1,250 and about 12,500 daltons and most particularly between about 2,500 and about 5,000 daltons. Therefore, it should be understood that the desired MW of the whole or combined polymer is between about 5,000 and about 50,000 Da with the most preferred MW of between about 10,000 and about 20,000 Da, where the molecule has four "arms", each arm having a MW of between about 1,250 and about 12,500 daltons with the most preferred MW of 2,500 and about 5,000 Da.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation. In one embodiment, the PA is a polyalkylene glycol polyether or derivative thereof, and most particularly is polyethylene glycol (PEG), the PEG unit having a molecular weight generally in the range of between about 1,250 and about 12,500 daltons, in particular between about 2,500 and about 5,000 daltons.

It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

It should be understood that the PA terminal end groups can be functionalized. Typically the end groups are OH, $NH_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (succinic acid) would "link" a terminal end group of a PA (such as a hydroxyl or an amine to form an ester or an amide respectively) with a reactive group of the DHPD (such as an $NH_2$, OH, or COOH). Suitable linkers include an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C3 through C10 dicarbonyl alkylenes such as malonic acid, succinic acid, etc.

A linking group refers to the reaction product of the terminal end moieties of the PA and DHPD (the situation where "a" is 0; no linker present) condense to form an amide, ester, urea, carbonate or urethane linkage depending on the reactive sites on the PA and DHPD. In other words, a direct bond is formed between the PA and DHPD portion of the molecule and no linker is present.

The denotation "HDP" refers to a multihydroxy phenyl derivative, such as a dihydroxy phenyl derivative, for example, a 3,4 dihydroxy phenyl moiety. Suitable DHDP derivatives include the formula:

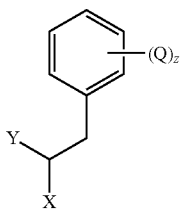

wherein Q is an OH;
"z" is 2 to 5;
X is $NH_2$, OH, or COOH; and
Y is H or COOH.

In particular, "z" is 2 and the hydroxyls are located at the 3 and 4 positions of the phenyl ring.

It should be understood that upon condensation of the DHDP molecule with the PA that a molecule of water, for example, is generated such that a bond is formed as described above (amide, ester, urea, carbonate or urethane).

In particular, DHPD molecules include dopamine, 3,4-dihydroxy phenylalanine (DOPA), dihydroxyhydrocinnamic acid, 3,4-dihydroxyphenyl ethanol, etc.

The denotation "AA" refers to an optional amino acid moiety or segment comprising one or more amino acids. Of particular interest are those amino acids with polar side chains, and more particularly amino acids with polar side chains and which are weakly to strongly basic. Amino acids with polar acidic, polar-neutral, non-polar neutral side chains are within the contemplation of the present invention. For some applications non-polar side chain amino acids may be more important for maintenance and determination three-dimensional structure than, e.g., enhancement of adhesion. Suitable amino acids are lysine, arginine and histidine, with any of the standard amino acids potentially being useable. Non-standard amino acids are also contemplated by the present invention.

The denotation "PG" refers to an optional protecting group, and if the protecting group is absent, PG is a hydrogen atom. A "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

The denotation "a" refers to a value of 0 when no linker is present (a bond is formed between the terminal end reactive portions of a PA and a DHPD) or is 1 when a linker is present.

The denotation of "b" has a value of one or more, typically between about 1 and about 20, more particularly between about 1 and about 10 and most particularly between about 1 and about 5, e.g., 1 to 3 inclusive. It should be understood that the DHPD can be one or more DHPD different molecules when b is 2 or more The denotation of "c" refers to a value of from 0 to about 20. It should be understood that the AA can be one or more different amino acids if c is 2 or more. In one embodiment, the sum of b+c is between 1 to about 20, in particular between about 1 to about 10 and more particularly between about 1 and about 5.

The denotation of "n" refers to values from 3 to about 15. In particular, n is 3, 4, or 5.

Note that as indicated in formula I, DHPD and AA moieties can be segments or "blocks" and can be and often are interspersed such that the DHPD/AA portion of each "arm" molecule can be a random copolymer or a random "block" copolymer. Therefore, for example, formula I(a) comprises:

While generally conforming to structural formula I, the "arms" of the compositions of this invention are separately and independently the same or different.

The present invention provides in one embodiment, a multi-armed, poly (alkylene oxide)polyether, multihydroxy (dihydroxy)phenyl derivative (DHPD) having the general formula:

$$CA\text{-}[Z\text{-}PA\text{-}(L)_a\text{-}(DHPD)_b\text{-}(AA)_c\text{-}PG]_n \qquad (II)$$

wherein

CA is carbon;

each Z, independently, is a C1 to a C6 linear or branched, substituted or unsubstituted alkyl group or a bond;

each PA, individually, is a substantially poly(alkylene oxide)polyether or derivative thereof;

each L, independently, optionally, is a linker or is a linking group selected from amide, ester, urea, carbonate or urethane linking groups;

each DHPD, independently, is a multihydroxy phenyl derivative;

each AA, independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value of 4.

Such materials are useful as adhesives, and more specifically, medical adhesives that can be utilized as sealants.

In one aspect, CA is a carbon atom and each Z is a methylene.

In another aspect, CA is a carbon atom, each Z is a methylene and each PA is a polyethylene oxide polyether that is a polyethylene oxide (PEG). The molecular weight of each PEG unit is between about 1,250 and about 12,500 daltons, in particular between about 2,500 and about 5,000 daltons.

In still another aspect, CA is a carbon atom, each Z is a methylene, each PA is a polyethylene oxide polyether that is a polyethylene oxide (PEG) and the linking group is an amide, ester, urea, carbonate or urethane. The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane and the DHDP is dopamine, 3,4-dihydroxyphenyl alanine, 3,4-dihydroxyphenyl ethanol or 3,4-dihydroxyhydrocinnamic acid (or combinations thereof). The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane, the DHDP is dopamine, 3,4-dihydroxyphenyl alanine, 3,4-dihydroxyphenyl ethanol or 3,4-dihydroxyhydrocinnamic acid (or combinations thereof) and each AA is lysine. The molecular weight of each PEG unit is between about 1,250 and about 12,500 daltons, in particular between about 2,500 and about 5,000 daltons. In particular, the linking group is an amide, urethane or ester.

In still another aspect, CA is a carbon atom, each Z is a methylene, each PA is a polyethylene oxide polyether that is a polyethylene oxide (PEG), the linking group is an amide, ester, urea, carbonate or urethane, the DHDP is dopamine, 3,4-dihydroxyphenyl alanine, 3,4-dihydroxyphenyl ethanol or 3,4-dihydroxyhydrocinnamic acid (or combinations thereof) and the PG is either a "Boc" or a hydrogen atom. The molecular weight of each PEG unit is between about 1,250 and about 12,500 daltons, in particular between about 2,500 and about 5,000 daltons. In particular, the linking group is an amide, urethane or ester.

In certain embodiments, "b" has a value of 1, 2, 3, or 4.

In certain embodiments, "c" has a value of zero, 1, 2, 3 or 4.

AA moieties can be segments or "blocks" and can be and often are interspersed such that the DHPD/AA portion of each "arm" molecule can be a random copolymer or a random or sequenced "block" copolymer. Therefore, for example, formula II(a) comprises:

$$CA\text{-}[Z\text{-}PA\text{-}(L)_a\text{-}[(DHPD)_b\text{-}(AA)_c]_{zz}\text{-}PG]_n \qquad II(a)$$

wherein CA is a carbon atom, Z, PA, L, DHPD, AA, PG, "a", "b", "c" and "n" are as defined above and zz is from 1 to about 20, in particular from about 2 to about 10 and most particularly from about 4 to about 8.

In certain embodiment, molecules according to this invention may be represented by:

$$C[-(OCH_2-CH_2)_{n1}\text{-}[(DOPA)_{n2}\text{-}(lys)_{n3}]_a[(lys)_{n3}\text{-}(DOPA)_{n2}]_b]_4$$

wherein a+b=1 means if a is 1 b is 0 and vice versa;

$n_1$ has a value in the range of about 10 to 500, preferably about 20 to about 250, and most preferably about 25 to about 100, for example, $n_1$ has value of between about 28 and 284 for PA of between about 1,250 and about 12,500 Da and in particular between about 56 and about 113 for a PA of between about 2,500 and about 5,000 Da;

$n_2$ has a value of 1 to about 10; $n_3$ has a value of 0 to about 10. In the above formula, it is to be understood that DOPA-lys (or other amino acids) peptide can be sequential or random.

Typically, formulations of the invention (the adhesive composition) have a solids content of between about 10% to about 50% solids by weight, in particular between about 15% and about 40% by weight and particularly between about 20% and about 35% by weight.

Exemplifying this invention, refined liquid adhesives possessing related chemical architecture were synthesized. The adhesive formulations depicted in FIG. 1 comprise a preferred branched, 4-armed poly(ethylene glycol) (PEG) end-functionalized with a single DOPA (C-(PEG-DOPA-Boc)$_4$), several DOPA residues (C-(PEG-DOPA$_4$)$_4$), a randomly alternating DOPA-lysine peptide (C-(PEG-DOPA$_3$-Lys$_2$)$_4$), a deaminated DOPA, 3,4-dihydroxyhydrocinnamic acid (C-(PEG-DOHA)$_4$), a dopamine through a urethane-linkage (C-(PEG-DMu)$_4$) and dopamine succinamic acid through an ester-linkage (C-(PEG-DMe)$_4$).

C-(PEG)-(DOHA)$_4$ is also sometimes referred to as Quadra Seal-DH herein. Regardless of polymer formulation, DOPA provides both adhesive and cohesive properties to the system, as it does in the naturally occurring MAPs. Without wishing to be bound to a theory, it is believed that the addition of the preferred amino acid lysine, contributes to adhesive interactions on metal oxide surfaces through electrostatic interactions with negatively charged oxides. Cohesion or crosslinking is achieved via oxidation of DOPA catechol by sodium periodate (NaIO$_4$) to form reactive quinone. It is further theorized, again without wishing to be bound by a theory, that quinone can react with other nearby catechols and functional groups on surfaces, thereby achieving covalent crosslinking.

The adhesives of the invention can be utilized for wound closure, such as a dura sealant.

As used herein, a wound includes damage to any tissue in a living organism. The tissue may be an internal tissue, such as the stomach lining, dura mater or pachymeninx or a bone, or an external tissue, such as the skin. As such a wound may include, but is not limited to, a gastrointestinal tract ulcer, a broken bone, a neoplasia, or cut or abraided skin. A wound may be in a soft tissue, such as the spleen, or in a hard tissue, such as bone. The wound may have been caused by any agent, including traumatic injury, infection or surgical intervention.

As used herein, the adhesives/compositions of the invention can be considered "tissue sealants" which are substances or compositions that, upon application to a wound, seals the wound, thereby reducing blood loss and maintaining hemostasis.

Typically the adhesive composition of the invention is applied to the surface to be treated, e.g., repaired, as a formulation with a carrier (such as a pharmaceutically acceptable carrier) or as the material per se.

The phrase "pharmaceutically acceptable carrier" means a pharmaceutically-acceptable material, composition or vehicle, such as a liquid or solid filler, diluent, excipient, solvent or encapsulating material that can be combined with the adhesive compositions of the invention. Each carrier should be "acceptable" in the sense of being compatible with the other ingredients of the composition and not injurious to the individual. Some examples of materials which may serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; phosphate buffered saline with a neutral pH and other non-toxic compatible substances employed in pharmaceutical formulations.

Alternatively, the adhesive composition of the invention can be applied as a "patch" that includes any shaped substrate compatible with surgical implantation and capable of being coated by an inventive sealant. The adhesive compositions can be formulated for use as an aqueous suspension, a solution, a powder, a paste, a sheet, a ring, a stent, a cone, a plug, a pin, a screw and complex three-dimensional shapes contoured to be complementary to specific anatomical features. Inventive patch materials include collagen; polylactic acid; hyaluronic acid; fluoropolymers; silicones; knitted or woven meshes of, for example, cellulosic fibers, polyamides, rayon acetates and titanium; skin; bone; titanium and stainless steel. Alternatively, pericardial or other body tissue may be used instead of a collagen patch. More preferably, the collagen is a flexible, fibrous sheet readily formed into a variety of shapes that is bioabsorbable and has a thickness of 25 millimeters. Such fibrous sheet collagen is commercially available from a number of suppliers. A collagen patch serves to enhance sealant strength while allowing some penetration of the inventive tissue sealant thereto. Optionally, in a surgical setting, a dry or a wetted absorbent gauze is placed proximal to the wound site in order to wick away any excess inventive tissue sealant prior to cure.

The inventive tissue adhesive composition can be delivered in conjunction with a propellant that is provided in fluid communication with a spray nozzle tip. Propellants include aerosol propellants such as carbon dioxide, nitrogen, propane, fluorocarbons, dimethyl ether, hydrochlorofluorocarbon-22, 1-chloro-1,1-difluoroethane, 1,1-difluoroethane, and 1,1,1-trifluoro-2-fluoroethane, alone or in combination.

The invention further provides crosslinked hydrogels derived from the compositions described herein. For example, two DHDP moieties from two separate polymer chains can be reacted to form a bond between the two DHDP moieties. Typically, this is an oxidative/radical initiated crosslinking reaction wherein oxidants/initiators such as $NaIO_3$, $FeCl_3$, $H_2O_2$, oxygen, an inorganic base, an organic base or an enzymatic oxidase can be used. Typically, a ratio of oxidant/initiator to DHDP containing material is between about 0.2 to about 1.0 (on a molar basis) (oxidant:DHDP). In one particular embodiment, the ratio is between about 0.25 to about 0.75 and more particularly between about 0.4 to about 0.6 (e.g., 0.5). It has been found that periodate is very effective in the preparation of crosslinked hydrogels of the invention.

Typically, when the DHDP containing material is treated with an oxidant/initiator as described, the material gels (crosslinks) within 1 minute, more particularly within 30 seconds, most particularly under 5 seconds and in particular within 2 seconds or less. For example, QuadraSeal-D4 (PEG10k-$(D_4)_4$) gelled with in 2 seconds or less at a $IO_4$:DOPA mole ratio of 0.25 or higher.

The following paragraphs enumerated consecutively from 1 through 30 provide for various aspects of the present invention. In one embodiment, in a first paragraph (1), the present invention provides a composition comprising the formula:

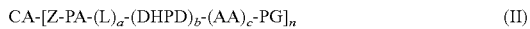

$$\text{CA-[Z-PA-(L)}_a\text{-(DHPD)}_b\text{-(AA)}_c\text{-PG]}_n \qquad (II)$$

wherein

CA is carbon;

each Z, independently, is a C1 to a C6 linear or branched, substituted or unsubstituted alkyl group or a bond;

each PA, independently, is a substantially poly(alkylene oxide)polyether or derivative thereof;

each L, independently, optionally, is a linker or is a linking group selected from amide, ester, urea, carbonate or urethane linking groups;

each DHPD, independently, is a multihydroxy phenyl derivative;

each AA independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value of 4.

2. The composition of claim 1, wherein each Z is a methylene.

3. The composition of any of claims 1 or 2, wherein each PA is a polyethylene glycol polyether.

4. The composition of any of claim 1 through 3, wherein the molecular weight of each of the PAs is between about 1,250 and about 12,500 daltons.

5. The composition of any of claims 1 through 4, wherein each DHPD is either dopamine, 3,4-dihydroxyphenyl alanine, 2-phenyl ethanol or 3,4-dihydroxyhydrocinnamic acid.

6. The composition of claim 5, wherein "c" is zero.

7. The composition of any of claims 1 through 6, wherein PG is a hydrogen atom.

8. The composition of any of claims 1 through 7, wherein "a" is zero.

9. The composition of any of claims 1 through 8, wherein "b" is 1, 2, 3 or 4.

10. The composition of any of claims 1 through 9, wherein the linking group is an amide, urea or urethane.

11. The composition of claim 5, wherein "c" is 1, 2, 3 or 4.

12. The composition of claim 11, wherein each AA is lysine.

13. The composition of any of claims 11 or 12, wherein PG is a hydrogen atom.

14. The composition of any of claims 11 through 13, wherein "a" is zero.

15. The composition of any of claims 11 through 14, wherein "b" is 1, 2, 3 or 4.

16. The composition of any of claims 11 through 15, wherein the linking group is an amide, ester or urethane.

17. The composition of claim 5, wherein "a" is 1 and each L is an alkylene dicarboxylic acid moiety.

18. The composition of claim 17, wherein the alkylene dicarboxylic acid moiety is succinic acid.

19. The composition of any of claims 17 or 18, wherein PG is a hydrogen atom.

20. The composition of any of claims 17 through 19, wherein "b" is 1, 2, 3 or 4.

21. The composition of any of claims 1 through 4 or 6, wherein the DHPD has at least 2 hydroxyl groups.

22. The composition of any of claims 1 through 4 or 6, wherein the DHPD has 2 hydroxyl groups.

23. A method to adhere biological tissues together, comprising the step of administering to the tissue a sufficient amount of an adhesive material as claimed in any of claims 1 through 22, such that the biological tissues remain adhered to each other.

24. A method to adhere biological tissues together, comprising the step of expressing onto the tissue a sufficient amount of an adhesive material as claimed in any of claims 1 through 22, such that the biological tissues remain adhered to each other.

25. A method to crosslink the material as claimed in any of claims 1 through 22 by reacting said hydroxyphenyl groups with an oxidant to yield hydroxyphenyl free radical species, such that the free radical species react to yield a crosslinkage comprising multiple hydroxyphenyl species.

26. The method of claim 25, wherein the oxidant is a periodate.

27. The method of claim 25, wherein the oxidant is NaIO$_3$, FeCl$_3$, H$_2$O$_2$, oxygen, an inorganic base, an organic base or an oxidase.

28. A cross linked macromolecular hydrogel comprising the formula:

$$CA\text{-}[Z\text{-}PA\text{-}(L)_a\text{-}(DHPD)_b\text{-}(AA)_c\text{-}PG]_n \quad (II)$$

as claimed in any of paragraphs 1 through 22, wherein
CA is a central atom that is carbon;
each Z, independently, is a C1 to a C6 linear or branched, substituted or unsubstituted alkyl group or a bond;
each PA, independently, is a substantially poly(alkylene oxide)polyether or derivative thereof;
each L, independently, optionally, is a linker or is a linking group selected from amide, ester, urea, carbonate or urethane linking groups;
each DHPD, independently is a multihydroxy phenyl derivative;
each AA independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value of 4, wherein at least one or more linkage(s) is/are formed between two DHPD groups attached respectively to adjacent molecules.

29. A composition comprising the formula:

$$CA\text{-}[Z\text{-}PA\text{-}(L)_a\text{-}(DHPD)_b\text{-}(AA)_c\text{-}PG]_n \quad (I)$$

wherein
CA is a central atom selected from carbon, oxygen, sulfur, nitrogen, or a secondary amine;
each Z, independently is a C1 to a C6 linear or branched, substituted or unsubstituted alkyl group or a bond;
each PA, independently, is a substantially poly(alkylene oxide)polyether or derivative thereof; each L, independently, optionally, is a linker or is a linking group selected from amide, ester, urea, carbonate or urethane linking groups;
each DHPD, independently, is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value from 3 to 15.

30. A cross linked macromolecular hydrogel comprising the formula:

$$CA\text{-}[Z\text{-}PA\text{-}(L)_a\text{-}(DHPD)_b\text{-}(AA)_c\text{-}PG]_n \quad (I)$$

wherein
CA is a central atom selected from carbon, oxygen, sulfur, nitrogen, or a secondary amine;
each Z, independently, is a C1 to a C6 linear or branched, substituted or unsubstituted alkyl group or a bond;
each PA, independently, is a substantially poly(alkylene oxide)polyether or derivative thereof;
each L, independently, optionally, is a linker or is a linking group selected from amide, ester, urea, carbonate or urethane linking groups;each DHPD, independently, is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value from 3 to 15, wherein at least one or more linkage(s) is/are formed between two DHPD groups attached respectively to adjacent molecules.

EXAMPLES

It should be understood that throughout the specification different abbreviations may be used for certain of the compounds. For example, C-(PEG-DOPA-Boc)$_4$ equals PEG10k-(D)$_4$, C-(PEG-DOPA$_4$)$_4$ equals PEG10k-(D$_4$)$_4$, C-(PEG-DOPA$_3$-Lys$_2$)$_4$ equals PEG10k-(DL)$_4$, C-(PEG-DOHA)$_4$ equals PEG10k-(DH)$_4$, C-(PEG-DMu)$_4$ equals PEG10k-(DMu)$_4$ and C—PEG-DMe)$_4$ equals PEG10k-(DMe)$_4$.

Detailed descriptions of the synthesis, curing, and adhesive experimentation for these adhesive polymers is as follow:
Synthesis of C-(PEG-DOPA-Boc)$_4$, C-(PEG-DOHA)$_4$, and C-(PEG-DMe)$_4$ C-(PEG-DOPA-Boc)$_4$ was synthesized by dissolving branched PEG-NH$_2$ (MW=10,000 Da) in a 2:1 DCM:DMF to make a 45 mg/mL polymer solution. 1.6 molar equivalent (relative to —NH$_2$) of N-Boc-DOPA, 1-hydroxybenzotriazole hydrate, and O-(Benzotriazol-1-yl)-N,N,N',N'-tetramethyluronium hexafluorophosphate were then added. 2.4 equivalent of triethylamine was finally added and the mixture was stirred at room temperature for 1 hour. Polymer purification was performed by precipitation in diethyl ether and cold methanol.

C-(PEG-DOHA)$_4$ (m=56) was synthesized as described above using 3,4-dihydroxy-hydrocinnamic acid (DOHA) instead of N-Boc-DOPA. The resulting polymer was purified by precipitation in diethyl ether followed by dialysis with deionized water (3500 MWCO) for 24 hours. Subsequent lyophilization yielded C-(PEG-DOHA)$_4$ (m=56), FIG. 1(d).

C-(PEG-DOHA)$_4$ (m=113) was synthesized as described above using 3,4-dihydroxy-hydrocinnamic acid (DOHA) instead of N-Boc-DOPA and PEG-NH$_2$ (MW=20,000 Da). The resulting polymer was purified by precipitation in diethyl ether followed by dialysis with deionized water (3500 MWCO) for 24 hours. Subsequent lyophilization yielded C-(PEG-DOHA)$_4$ (m=113), FIG. 1g.

C-(PEG-DMe)$_4$ was synthesized by first reacting branched PEG-OH (MW=10,000 Da) with 5 times excess (relative to —OH) of succinic anhydride and catalytic amount of pyridine in chloroform at 70° C. for 18 hrs. After repeated precipitation in chloroform/ethyl ether, the resulting C-(PEG-SA)$_4$ is further reacted with 1.6 equivalent of dopamine hydrochloride using similar procedures as described above. The resulting polymer was purified by precipitation in diethyl ether followed by dialysis with deionized water acidified to pH 3.5 with hydrochloric acid (3500 MWCO) for 24 hours. Subsequent lyophilization yielded C-(PEG-DMe)$_4$.
Synthesis of C-(PEG-DOPA$_4$)$_4$ and C-(PEG-DOPA$_3$-Lys$_2$)$_4$ N-carboxyanhydrides (NCAs) of DOPA (diacetyl-DOPA-NCA) and lysine (Fmoc-Lys-NCA) were prepared by following literature procedures [1,2]. Four-armed PEG-NH$_2$ (MW=10,000 Da) was first dried by azeotropic evaporation with benzene and dried in a desiccator for ≥3 h. Ring-opening polymerization of NCA was performed by dissolving 4-armed PEG-NH$_2$ in anhydrous THF at 100 mg/mL and purged with argon. Six molar excess (relative to —NH$_2$) of diacetyl-DOPA-NCA with or without Fmoc-Lys-NCA was added neat. The reaction mixture was stirred at room temperature for 5 d with a dry tube outlet. The peptide-modified block copolymers were purified in succession with ethyl ether three times. Peptide-coupled PEG was dissolved in anhydrous DMF at a concentration of 50 mg/mL and bubbled with Ar for 10 min. Pyridine was added to make a 5% solution and stirred for 15 min with Ar bubbling. The mixture was rotary evaporated to remove excess pyridine and precipitated in ethyl ether. The crude polymer was further purified by dialyzing the compound in deionized water (MWCO 3500) for 4 hours and lyophilized to yield the final products.
Synthesis of PEG10k-(DMU)$_4$ 10 g of 4-armed PEG-OH (10,000 MW; 4 mmol —OH) was dried with azeotropic evaporation with toluene and dried in a vacuum desiccator. To PEG in 90 mL of toluene was added 10.6 mL of phosgene solution (20% phosgene in toluene; 20 mmol phosgene) and the mixture was stirred for 4 hrs in a 55° C. oil bath, with Ar purging and a NaOH solution trap in the outlet to trap escaped phosgene. The mixture was evaporated and dried with vacuum overnight. 65 mL of chloroform and 691 mg of N-hydroxysuccinimide (6 mmol) were added to chloroformate-activated PEG and 672 mL of triethylamine (4.8 mmol) in 10 mL of chloroform was added dropwise. The mixture was stirred under Ar for 4 hrs. 1.52 g of dopamine-HCl (8 mmol), 2.24 mL of triethylamine (8 mmol), and 25 mL of DMF was added, and the polymer mixture was stirred at room temperature for overnight. 100 mL of chloroform was added and the solution was washed successively with 100 mL each of 12 mM HCl, saturated NaCl solution, and H$_2$O. The organic layer was dried over MgSO$_4$. MgSO$_4$ was removed by filtration and the filtrate was reduced to around 50 mL and added to 450 mL of diethyl ether. The precipitate was filtered and dried to yield 8.96 g of PEG10k-(DMu)$_4$.
Characterization of Adhesive Polymers Both $^1$H NMR and UV-vis were used to quantify the amount of PEG-bound DOPA and Lys following literature procedures [3].
Adhesive Formulations For each polymer formulation, the molar and volume ratios of periodate (IO$_4^-$) to polymer endgroups were adjusted to yield the most desirable gelation times (20-40s). The results of these experiments are summarized in Table 1.

TABLE 1

Volume ratios of the adhesive polymer and crosslinking agent solutions that yielded optimal gelation times.

| | Endgroup:IO$_4^-$ Molar Ratio | Polymer:NaIO$_4$ Volume Ratio | Gelation Time (sec) |
|---|---|---|---|
| C-(PEG-DOPA-Boc)$_4$ | 2 | 10 | 20 |
| C-(PEG-DOPA$_4$)$_4$ | 2 | 1 | 25 |
| C-(PEG-DOPA$_3$-Lys$_2$)$_4$ | 2 | 2 | 40 |

The adhesive performance of these three new liquid adhesives was tested by lap-shear method in two different systems. Titanium was chosen for its relevance to orthopedics to test performance in a metal-metal system. Titanium was sputter-coated onto glass slides at a thickness of 50 nm (Platypus Technologies, Madison, Wis.) to produce suitable test surfaces. To examine adhesive behavior on soft tissue, porcine dermal tissue was selected. Titanium test surfaces were prepared by sputter coating commercially pure Ti on to glass microscope slides. Soft tissue test surfaces were created by slicing porcine dermal tissue into 120 µm sections (~25 mm×25 mm) and gluing those sections to glass microscope slides using gel-type cyanoacrylate glue.

The parameters shown in Table 1 were used to prepare test assemblies for tensile adhesion tests for each C-(PEG-X)$_4$ formulation. To test adhesive performance, a small volume (typically 100-200 µL) of adhesive precursor (C-(PEG-DOPA-Boc)$_4$, C—(PEG-DOPA$_4$)$_4$, or C-(PEG-DOPA$_3$-Lys$_2$)$_4$) was dissolved in phosphate-buffered saline (PBS; pH 7.4) was placed on a 25 mm×25 mm area of the test surface. An appropriate volume of NaIO$_4$ in ultrapure water was added to the precursor solution on the surface. The two components were mixed on the surface for several seconds using a pipette tip, and the second surface was approximated immediately after mixing. The surfaces were allowed to let stand undisturbed for at least one minute to allow for curing. For all formulations, the final polymer adhesive concentration was 150 mg/mL.

Liposomal Delivery of Crosslinking Reagent

A modification in the delivery method of the crosslinking reagent was achieved by encapsulating $NaIO_4$ in thermally-triggerable liposomes. $NaIO_4$-loaded liposomes were prepared by the interdigitation-fusion (IF) approach. Briefly, a dry thin film of phospholipids (90 mol % dipalmitoylphosphatidylcholine and 10 mol % dimyristoylphosphatidylcholine) was hydrated with aqueous $NaIO_4$ in PBS (pH 6, 42 mM, 357 mOsm) in a round bottom flask for 15 minutes at 50° C. The resulting vesicle suspension was sonicated at 50° C. until optically clear using a probe-type ultrasonicator to form small unilamellar vesicles (SUVs). The SUV suspension was centrifuged to remove metal particles released from the probe tip, and 100% ethanol was added with vortexing to achieve a final ethanol concentration of 4M. After incubation at room temperature for 15 min, the suspension was heated to 50° C. and bubbled with $N_2$ gas for 30 min to remove EtOH, yielding $NaIO_4$-encapsulated interdigitation-fusion vesicles ($NaIO_4$-IFVs). All subsequent manipulations of liposomes were performed at 20° C. to prevent release of entrapped $NaIO_4$. Unentrapped $NaIO_4$ was removed from the liposome suspension by washing with iso-osmotic PBS (pH 6), centrifuging at 20,000×g, and decanting the supernatant. This process was repeated a minimum of five times or until $NaIO_4$ could not be detected in the supernatant, using a standard spectrophotometric method.

$NaIO_4$ concentration was determined spectrophotometrically. Standard solutions containing 0-72 mM $NaIO_4$ were prepared by dissolution in 2 mL of 0.1M citrate buffer (pH 6) and 2 mL of 0.01% Triton, and diluted to 9 ml total volume with ultrapure water. Liposome-containing solution was prepared similarly adding 15 uL $NaIO_4$ liposomes in place of aqueous $NaIO_4$. Each solution had NaI (1 mL) added to it, was vortexed and incubated for 3 minutes. The absorbance of each solution was then measured at 352 nm (Hitachi U-2010 UV/VIS spectrophotometer). A linear standard curve was produced and the concentration of the liposome-containing solution was calculated. An average concentration of 33.4 mM $NaIO_4$ was obtained.

Temperature-dependent release of $NaIO_4$ was observed spectrophotometrically by heating $NaIO_4$-IFV's suspended in isosmotic solutions containing either L-DOPA or C-(PEG-DOPA-Boc)$_4$. The release of periodate into solution results in oxidation of the catechol sidechain in DOPA. The release of periodate in the presence of L-DOPA was first determined. 15 µL of $NaIO_4$ liposomes were added and mixed into osmotically balanced PBS (5 mL, pH 6) containing 50 µM L-DOPA. A portion of this solution was placed in a cuvette. A water bath and heat exchanger were used to slowly raise the temperature of the liposome-containing solution from 25° C. to 50° C. at a rate of 1° C./min. The release of periodate was followed by measuring the absorbance of the liposomes containing solution at 320 nm. The thermal release of periodate and subsequent oxidation of C-(PEG-DOPA-Boc)$_4$ was observed similarly by replacing L-DOPA with C-(PEG-DOPA-Boc)$_4$ (500 µM).

To measure adhesive strength of thermally-triggered hydrogel formation, C-(PEG-DOPA-Boc)$_4$ was dissolved in PBS (300 mg/mL) by vortexing at room temperature for 2 minutes. C-(PEG-DOPA-Boc)$_4$ hydrogel adhesive was prepared by mixing equal parts of the PEG-DOPA solution with $NaIO_4$-IFV's to a final C-(PEG-DOPA-Boc)$_4$ concentration of 150 mg/mL. Adhesive (100 µL) was applied to one surface of the aluminum backed tissue substrate. Two copper wire spacers (250 µm) were placed at each end of the overlap area to create a space between the two tissue surfaces of the test pieces. The second test piece was then placed on top of the first being careful to ensure that the proper 1 cm overlap area guideline was followed. Moist gauze and a 200 g weight were then placed on top of the test pieces and remained in place for the duration of the cure time. PBS was added to the container that the test pieces were placed and the ends of the gauze strips were immersed into the solution to maintain hydration throughout the duration of the cure time. The container with test assemblies was placed into a 37° C. oven for 24 hours. The time between applying adhesive to the first surface and the placing of the test pieces into the oven was approximately 10 minutes.

Adhesive Strength

An Instron 5566 mechanical testing apparatus was used to assay lap-shear tensile adhesive strength of the three branched PEG-DOPA liquid adhesives. Samples were loaded into the pneumatic grips (90 psi) and the samples were strained at a rate of 5 mm/min until the adhesive failed. Load was recorded throughout the experiment and was converted to shear stress by normalizing to the adhered surface area (6.25 $mm^2$). Additionally, observations were made during individual tests regarding the mode of failure to determine whether adhesive or cohesive failure predominated. Five replicate tests were performed for each formulation and surface.

Table 2 illustrates the typical failure modes for each formulation in the metal-metal system. While the maximum shear stress did not increase between C-(PEG-DOPA-Boc)$_4$ and C-(PEG-DOPA$_4$)$_4$, the typical mode of failure transitioned from principally adhesive failure to principally cohesive failure. This phenomenon suggests that the increase in the number of DOPA residues in the adhesive produces stronger bond with the Ti surface. The C-(PEG-DOPA$_3$-Lys$_2$)$_4$ withstood a markedly higher maximum shear stress and failure occurred in cohesion on all five test samples.

TABLE 2

Number of occurrences of each failure mode of liquid adhesive formulations between titanium surfaces.

| | Adhesion | ⟵⟶ | | Cohesion |
|---|---|---|---|---|
| C-(PEG-DOPA-Boc)$_4$ | XXXXX | | | |
| C-(PEG-DOPA$_4$)$_4$ | X | X | | XXX |
| C-(PEG-DOPA$_3$-Lys$_2$)$_4$ | | | | XXXXX |

The maximum shear stresses for all three branched PEG-DOPA formulations between soft tissue surfaces were measured. A decrease in maximum shear stress between C-(PEG-DOPA-Boc)$_4$ and C-(PEG-DOPA$_4$)$_4$ on porcine skin was anomalous plain, but may have been the result of decreased solubility of the endgroup as DOPA content is increased. Again C-(PEG-DOPA$_3$-Lys$_2$)$_4$ showed a marked increase in maximum shear stress over the other two formulations. Negative control tests with C-(PEG-DOPA-Boc)$_4$+$CaCl_2$ and unfunctionalized branched PEG+$NaIO_4$ showed no adhesive activity as anticipated, indicating that the presence of both DOPA and the crosslink agent are required for rapid curing to form an adhesive bond between the surfaces. Of particular note is that all branched PEG-DOPA formulations out-perform commercially available fibrin glue (Baxter's Tisseel VH).

Table 3 illustrates the typical failure modes for each formulation in the skin-skin system. Once again, the failure mode in the skin-skin adhesion model trended toward consistent cohesive failure with increasing number of DOPA and lysine residues in the polymer endgroup.

TABLE 3

Number of occurrences of each failure mode of liquid adhesive formulations between soft tissue surfaces.

|  | Adhesion | ⟵⟶ | Cohesion |
|---|---|---|---|
| C-(PEG-DOPA-Boc)$_4$ | X | X | XXX |
| C-(PEG-DOPA$_4$)$_4$ | X |  | XXXX |
| C-(PEG-DOPA$_3$-Lys$_2$)$_4$ |  |  | XXXXX |

Adhesive Strength of Liposomally-Triggered Adhesive

By utilizing liposomes to compartmentalize the oxidation reagent NaIO$_4$ in solution with PEG-DOPA a mixture is created that can be stored at room temperature that can be later polymerized at the wound site by the increase in temperature caused by body heat. Furthermore, the adhesive mixture is a single solution which may lead to greater ease of use compared to two component systems such as fibrin glue and could be injected into sites without having to worry about proper mixing. The adhesive properties of C-(PEG-DOPA-Boc)$_4$/NaIO$_4$-IFV's as a tissue adhesive were studied on porcine skin. Mechanical tests were performed on an Instron mechanical testing machine along with control solutions. After allowing the adhesive to cure for 24 hours at 37° C. the substrates could be manipulated for tensile test measurements. They were carefully placed in position and tested. The adhesive had a mean lap shear tensile strength of 35 kPa (SD=12.5 kPa, n=11). Inspection of the adhesive site after testing showed gelled C-(PEG-DOPA-Boc)$_4$/NaIO$_4$ covering both tissue surfaces which indicated gel cohesive failure as opposed to adhesive failure to tissue surface. The gel and tissue maintained hydration throughout the experiment as the surfaces were still moist to the touch after experiments were concluded. Neither control solutions showed signs of adhesion; all specimens broke after the 24 hour cure time, when the weight was lifted off of the substrate.

Summary

A set of liquid polymer adhesives has been demonstrated to function as effective adhesives in vitro for binding metal oxides and porcine dermal tissue together. The resulting adhesive strength for all formulations is substantially higher than that of the leading commercial fibrin adhesive when tested on skin.

Encapsulation of crosslinking reagent in liposomes may be desirable for certain indications where access to the wound site is limited and injection of the adhesive precursor is required, or where adequate mixing is a substantial concern. It should be noted that preparation of liposomal crosslinking reagents is more costly (materials and labor), and from a cost-efficacy standpoint may not be warranted for all applications.

The observation that failure occurred largely in the cohesive mode suggests that DOPA-mediated adhesion shows a great deal of promise as a commercial tissue adhesive, and provides optimism that the inventors can engineer future formulations with enhanced cohesive properties which may further broaden areas of application where stronger, tougher medical adhesives are required.

Figure 7:
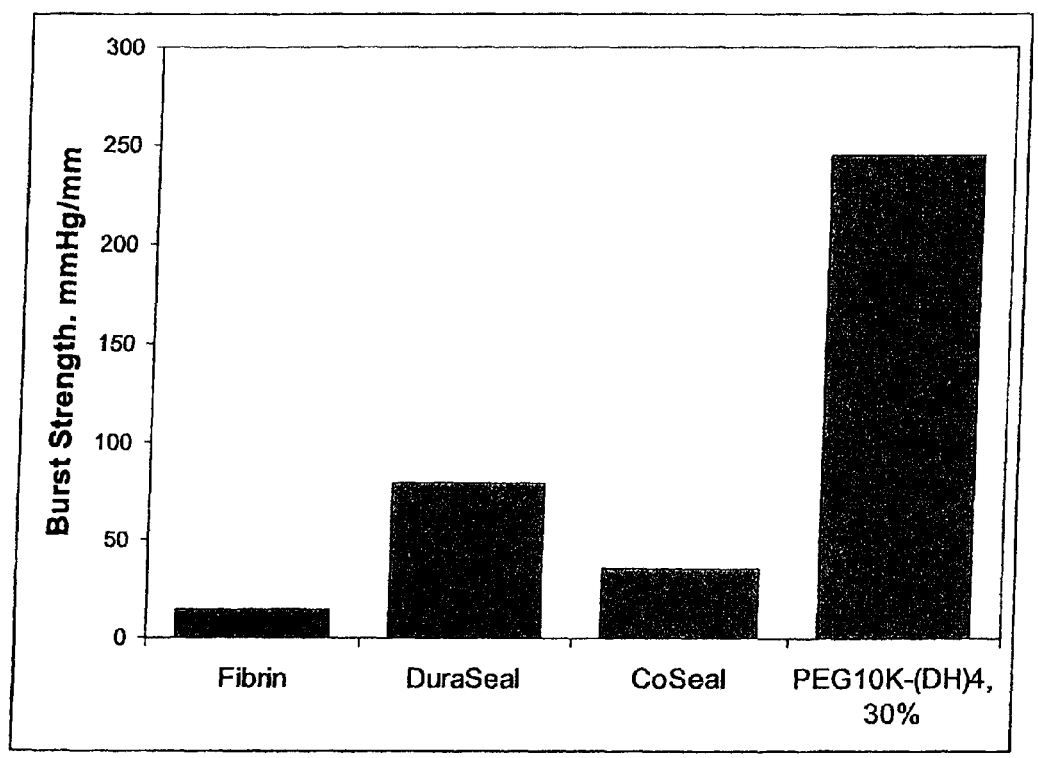
FIG. 7 shows comparative burst strength results for PEG10K-(DH)$_4$, 30% (FIG. 1(d)) versus other tissue adhesions.

Comparison of PEG10K-(DH)$_4$, 30% Solids, Tissue Adhesive, Burst Strength Versus Other Tissue Adhesives Comparative burst strength measurements for an adhesive of this invention (FIG. 1(d)) versus other tissue adhesives are shown in FIG. 7. The measurements were made in accordance with ASTM Test Standard F 2392-04, the contents of which are incorporated herein in their entirety and a method described by authors at Confluent Surgical, Inc. entitled "Evaluation of Absorbable Surgical Sealants: In vitro Testing" Patrick K. Campbell et al., white paper, Confluent Surgical, 2005, the contents of which are incorporated herein in their entirety. The adhesives described herein exhibited a surprising and unexpected improvement over existing products.

PEG10K-(DH)$_4$, 30% solids, FIG. 1(d), has been also evaluated in two different animal model tests; a rat skin laceration closure test and a rat aorta resealing evaluation. In the case of skin laceration closure, PEG10K-(DH)$_4$, 30% solids, was compared directly to Dermabond™, a leading cyanoacrylate adhesive, and sutures. Rat skin lacerations were sealed with either sutures or one of the two skin adhesives. No differences were observed in the wound closure strength of PEG10K-(DH)$_4$, 30% solids and Dermabond products and all cases showed complete healing between one to three weeks. This demonstrates that PEG10K-(DH)$_4$, 30% solids is compatible with living tissues and does perform well as a tissue adhesive. Note that the cyanoacrylate based Dermabond is the strongest tissue adhesive approved for use in the United States for use in closing external wounds but cannot be used for internal would sealing due to safety concerns.

Formulation of PEG10k-(DH)$_4$ with NaIO$_4$

The polymer precursor was prepared by dissolving 300 mg of PEG10k-(DH)$_4$ (0.45 μmol DHP/mg) in 1.0 mL double-strength phosphate buffered saline (PBS2x; Fisher Scientific p/n BP661-10) (30% solids). The crosslinking precursor was prepared by dissolving 11.4 mg of NaIO$_4$ (Sigma) in 1.0 mL ultrapure water. After correction for the volume contributed by the polymer, the formulation gives a 2:1 stoichiometry of DHP groups to periodate ions.

Formulation of PEG10k-(DH)$_4$ with NaIO$_4$ and NaOH

The polymer precursor was prepared by dissolving 300 mg of PEG10k-(DH)$_4$ (0.45 μmol DHP/mg) in 1.0 mL PBS2x containing 20 mM NaOH (30% solids). The crosslinking precursor was prepared by dissolving 11.4 mg of NaIO$_4$ (Sigma) in 1.0 mL ultrapure water. After correction for the volume contributed by the polymer, the formulation gives a 2:1 stoichiometry of DHP groups to periodate ions.

Formulation of PEG10k-(DH)$_4$ with NaIO$_4$, NaOH, and FD&C Blue #1

The polymer precursor was prepared by dissolving 300 mg of PEG10k-(DH)$_4$ (0.45 μmol DHP/mg) in 1.0 mL PBS2x containing 20 mM NaOH (30% solids). The crosslinking precursor was prepared by dissolving 11.4 mg of NaIO$_4$ (Sigma) in 1.0 mL ultrapure water containing 0.025% FD & C Blue #1 dye (Spectrum Chemical Mfg. Corp., p/n FD110). After correction for the volume contributed by the polymer, the formulation gives a 2:1 stoichiometry of DHP groups to periodate ions.

Procedure to Form a 15% Solids Hydrogel from PEG10k-(DH)$_4$ (Example A)

PEG10k-(DH)$_4$ (300 mg) was dissolved in 1 mL PBS2x and loaded into a 3 mL disposable polypropylene syringe. NaIO$_4$ (11.4 mg) was dissolved in 1 mL ultrapure water and loaded into a second 3 mL disposable polypropylene syringe. The syringes were loaded such that on combination in an equal volume delivery system the resulting gel would have a final % solids of 15%. The two syringes were attached to a blending connector with a spray tip (Micromedics, p/n SA-3674) and mounted in a double barrel syringe holder (Micromedics, p/n SA-3303).

Procedure to Form a 30% Solids Hydrogel from PEG10k-(DH)$_4$ (Example B)

PEG10k-(DH)$_4$ (600 mg) was dissolved in 1 mL PBS2x and loaded into a 3 mL disposable polypropylene syringe. NaIO$_4$ (18.8 mg) was dissolved in 1 mL ultrapure water and loaded into a second 3 mL disposable polypropylene syringe. The syringes were loaded such that on combination in an equal volume delivery system the resulting gel would have a final % solids of 30%. The two syringes were attached to a blending connector with a spray tip (Micromedics, p/n SA-3674) and mounted in a double barrel syringe holder (Micromedics, p/n SA-3303).

Procedure to Form a 15% Solids Colored Hydrogel from PEG10k-(DH)$_4$

PEG10k-(DH)$_4$ (300 mg) was dissolved in 1 mL PBS2x and loaded into a 3 mL disposable polypropylene syringe. NaIO$_4$ (11.4 mg) was dissolved in 1 mL ultrapure water containing 0.025% FD & C Blue #1 dye and loaded into a second 3 mL disposable polypropylene syringe. The syringes were loaded such that on combination in an equal volume delivery system the resulting gel would have a final % solids of 15%. The two syringes were attached to a blending connector with a spray tip (Micromedics, p/n SA-3674) and mounted in a double barrel syringe holder (Micromedics, p/n SA-3303).

Gel Time Measurement by Vial Tilt Method

200 µL of the polymer precursor was added to a 10 mm glass test tube. 200 µL of the crosslinking precursor was added to the test tube and the mixture was rapidly agitated for ~1 second on a vortexer. The test tube was then tilted every 5 seconds to observe the gross flow characteristics of the fluid. Gelation was defined as the absence of fluid flow when the vial is tilted.

Gel Time Measurement by Stir Bar Method

A 5 mm×2 mm Teflon-coated stir bar was placed in a 10 mm test tube containing 100 µL of the polymer precursor solution. The stir bar was rotated at 300 rpm. 100 µL of the crosslinking precursor was added to the test tube. Gelation was defined as the time when the stir bar stopped spinning.

Equilibrium Swelling Method

Six 20 mL plastic scintillation vials were weighed (without the cap) and labeled and weights were recorded. Adhesive precursor solutions (1 mL each) were individually loaded into 3 mL disposable polypropylene syringes. Using a manual spray-type applicator (Micromedics, #SA-3674), the adhesive was expressed in a Teflon sheet in 1-2 cm drops. The adhesive drops were allowed to cure on the bench for 10 min. The gels were carefully placed in each of the vials and weighed. The weight of the vial was subtracted to arrive at the relaxed weight ($W_r$) of the gel. The gels were covered with 10 mL of phosphate-buffered saline and allowed to stand at room temperature for 24 h. The saline solution was aspirated and excess liquid in the vial was absorbed using a laboratory tissue. The vials containing the gels were reweighed to obtain the swollen weight ($W_s$). Swollen gels were placed in a vacuum dessicator overnight to remove water and were then reweighed to obtain dry weight ($W_d$). The volumetric swelling ratio (R) is calculated as follows:

$$R = \frac{V_s}{V_r}$$

$$V_s = \frac{W_d}{\rho_{PEG}} + \frac{W_s - W_d}{\rho_{Solvent}}$$

$$V_r = \frac{W_d}{\rho_{PEG}} + \frac{W_r - W_d}{\rho_{Solvent}}$$

where $\rho_{PEG}$ is the density of the polymer (1.123 g/mL) and $\rho_{solvent}$ is the density of the solvent (1.123 g/mL for water).

Lap Shear Adhesion Testing Method

Figure 8:
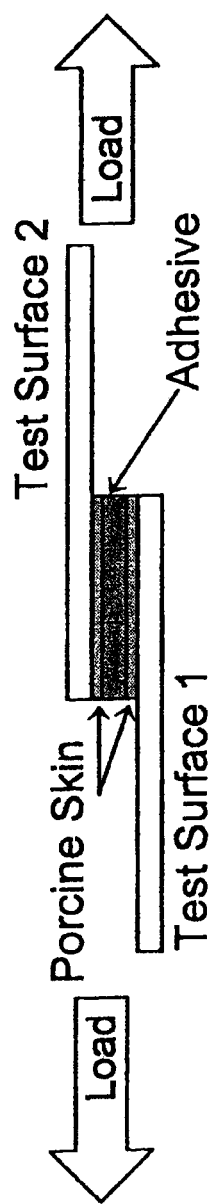
FIG. 8 provides lap-shear tensile stress measurements performed on porcine tissue or collagen film.

Lap-shear tensile stress measurements were performed on porcine tissue (Brennen Medical, Inc.) or collagen film (Vista International, p/n F-320) following the procedures described in ASTM standard F 2255-05, the contents of which are incorporated herein in their entirety. The biological substrate was prepared by adhering thinly sliced porcine dermis or collagen to a glass slide using cyanoacrylate glue. Aqueous solutions of various adhesive formulations were applied to one substrate and the second substrate was approximated as shown in FIG. 8. Test assemblies were allowed to cure for 5 minutes. The test samples were placed in an incubator at 37° C. and 100% RH for 1 h before testing. Test assemblies were strained in shear at 5 mm/min until failure. The peak stress was recorded.

T-Peel Adhesion Testing Method

Collagen test material (Vista International, p/n F-320) was prepared by re-hydrating in water. The collagen was rinsed with 0.1% sodium dodecyl sulfate solution, followed by a rinse with water and then allowed to soak in PBS for 10 minutes before testing. The collagen material was cut into 3×1 samples. Adhesive was spread evenly on the samples, which were then approximated and a ~1N force was applied for 5 min while the adhesive set. The test samples were placed in an incubator at 37° C. and 100% RH for 1 h before testing. The average force required to pull the samples apart at a rate of 175 mm/min was recorded.

Burst Strength Test Method

The burst strengths of various adhesive formulations were tested using a protocol based on ASTM Standard F 2392-04. In brief, collagen sausage casing (Vista International) was rinsed well in water and 0.1% sodium dodecyl sulfate to remove glycerin preservative. The collagen material was cut into 30 mm dia. circular pieces. In each piece a 3 mm circular defect was created on-center using a leatherworking punch. Adhesive formulations were applied to the collagen substrate inside a PFTE mask (inside diameter=15 mm). The adhesive gels were allowed to cure at ambient for 5 min and were then transferred to a 37° C. saline bath for one hour. Sealed defects were tested on a custom built apparatus consisting of a syringe pump, test fixture, and pressure gauge. The system was pressurized at 2 mL/min until the gel failed. The maximum pressure attained was recorded.

Sterilization of 4-armed PEGs by Various Methods

Figure 9:
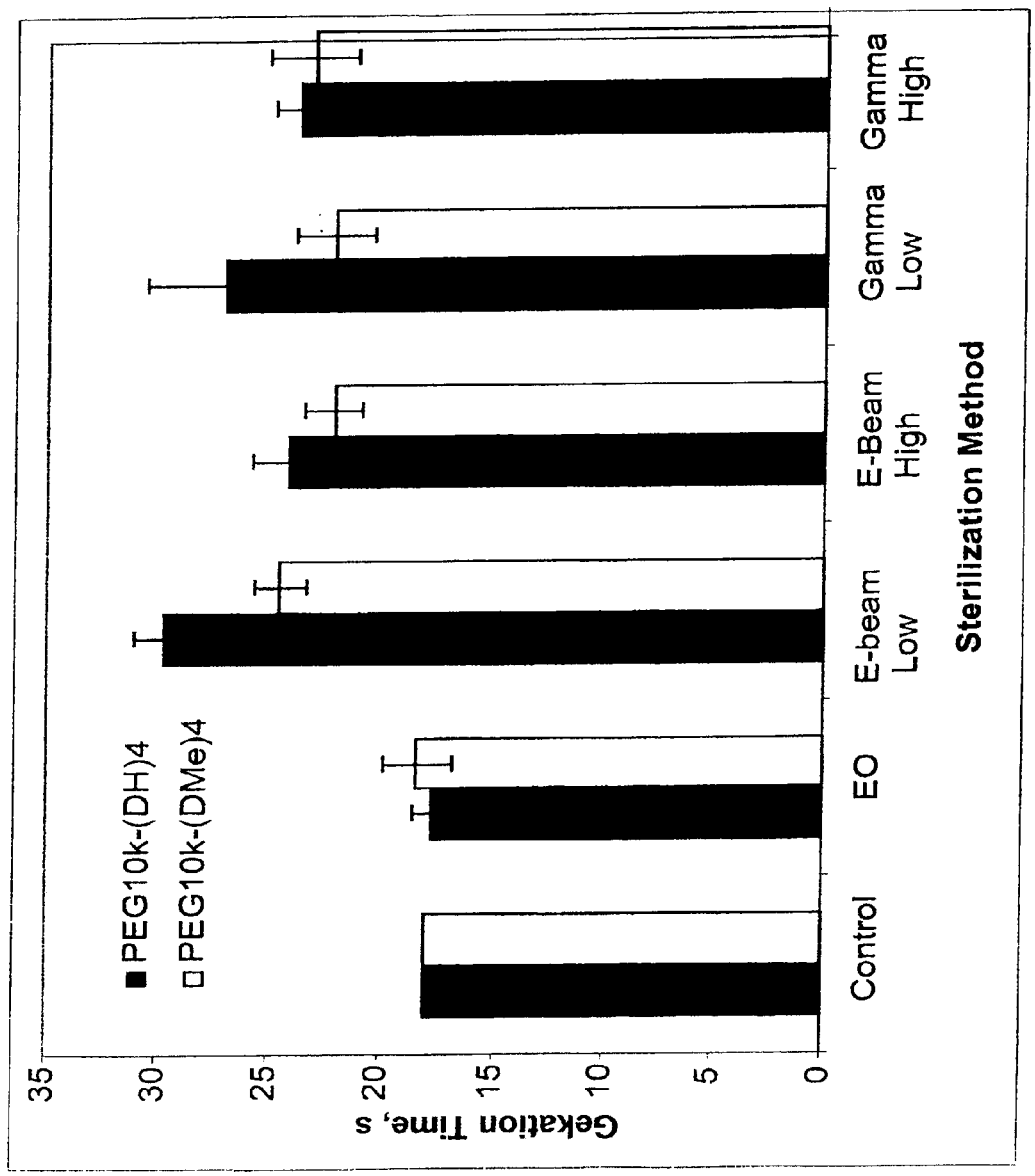
FIG. 9 provides bulk samples of PEG10k-(DH)$_4$, and of PEG10k-(DMe)$_4$ that were subjected the various sterilization treatments.

Bulk samples of PEG10k-(DH)$_4$ and of PEG10k-(DMe)$_4$ were subjected the various sterilization treatments (Steris/ISOMEDIX). The sterilization methods utilized were ethylene oxide gas (EO), electron beam irradiation (E-beam) at low (10 kGy) and high (30 kGy) doses, and gamma irradiation at low (10 kGy) and high (30 kGy) doses. After sterilization, the precursor solutions were formulated for gels containing 15% solids as described above. Gelation times of the formulations were determined by the vial-tilt method. The data are shown in FIG. 9.

Change in Gel Time as a Function of Polymer Precursor Solution Age

Figure 10:
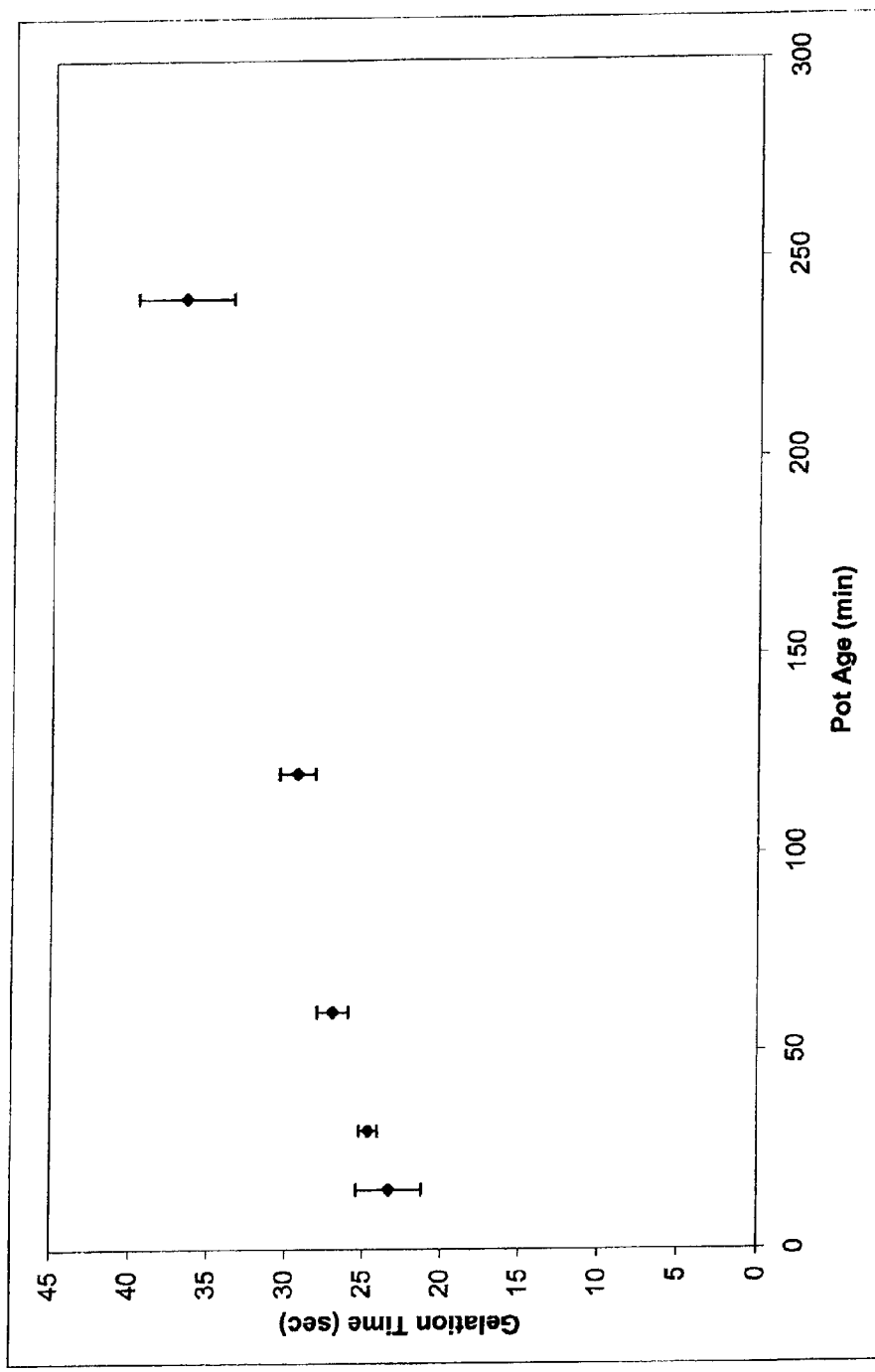
FIG. 10 provides various time points after reconstitution (pot ages) for gelation time of various formulations determined by the vial-tilt method.

The polymer precursor was prepared by dissolving 900 mg of PEG10k-(DH)$_4$ (0.45 µmol DHP/mg) in 3.0 mL double-strength phosphate buffered saline (PBS2x; Fisher Scientific p/n BP661-10) (30% solids). The crosslinking precursor was prepared by dissolving 34.2 mg of NaIO$_4$ (Sigma) in 3.0 mL ultrapure water. At various time points after reconstitution (pot ages), gelation time of the formulation was determined by the vial-tilt method. The data are plotted in FIG. 10.

Gel Formation at Different Percent Solids from PEG10k-(DH)$_4$

Figure 11:
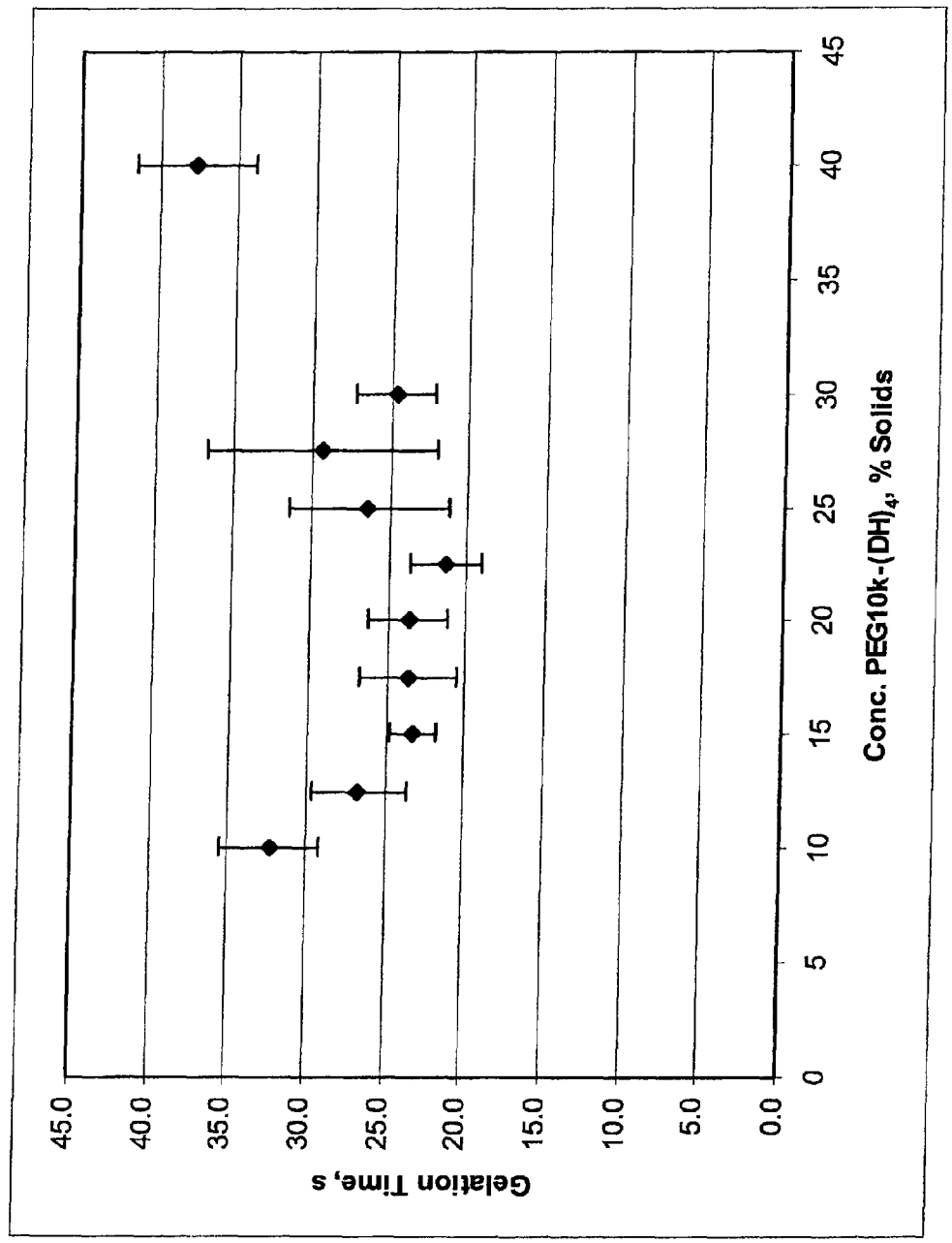
FIG. 11 provides gel formation at different percent solids for PEG10k-(DH)$_4$.

Polymer precursor solutions of PEG10k-(DH)$_4$ in PBS2x ranging from 20-80% solids were prepared. Crosslinking precursor solutions were prepared such that after correction for the volume contributed by the polymer, the each formulation gave a 2:1 stoichiometry of DHP groups to periodate ions. Gelation time of each formulation was determined by the vial-tilt method. The data are plotted in FIG. 11.

Thermal Profile of Gel Formation

The polymer precursor was prepared by dissolving 450 mg of PEG10k-(DH)$_4$ (0.45 μmol DHP/mg) in 1.5 mL double-strength phosphate buffered saline (PBS2x; Fisher Scientific p/n BP661-10) (30% solids). The crosslinking precursor was prepared by dissolving 17.1 mg of NaIO$_4$ (Sigma) in 1.5 mL ultrapure water. The gelation of each sample proceeded as described for the vial-tilt gelation method. The temperature of the polymer precursor ($T_{begin}$) was recoded using a digital temperature probe. After addition of the crosslinking precursor, the temperature of the gelling mixture was monitored and the temperature 1 min after mixing ($T_{gel}$) was recorded. The difference in temperatures was recorded. The data are listed in Table 4.

TABLE 4

| Sample # | $T_{begin}$ (° C.) | $T_{gel}$ (° C.) | Δ T(° C.) |
|---|---|---|---|
| 1 | 22.4 | 23.2 | 0.8 |
| 2 | 22.7 | 23.2 | 0.5 |
| 3 | 22.3 | 23 | 0.7 |
| 4 | 22.3 | 22.9 | 0.6 |
| 5 | 22.1 | 23 | 0.9 |
| 6 | 21.4 | 22.5 | 1.1 |
|   |      | Mean | 0.8 |

Preparation of Rapidly Gelling Formulations Using Elevated pH Buffer

Figure 12:
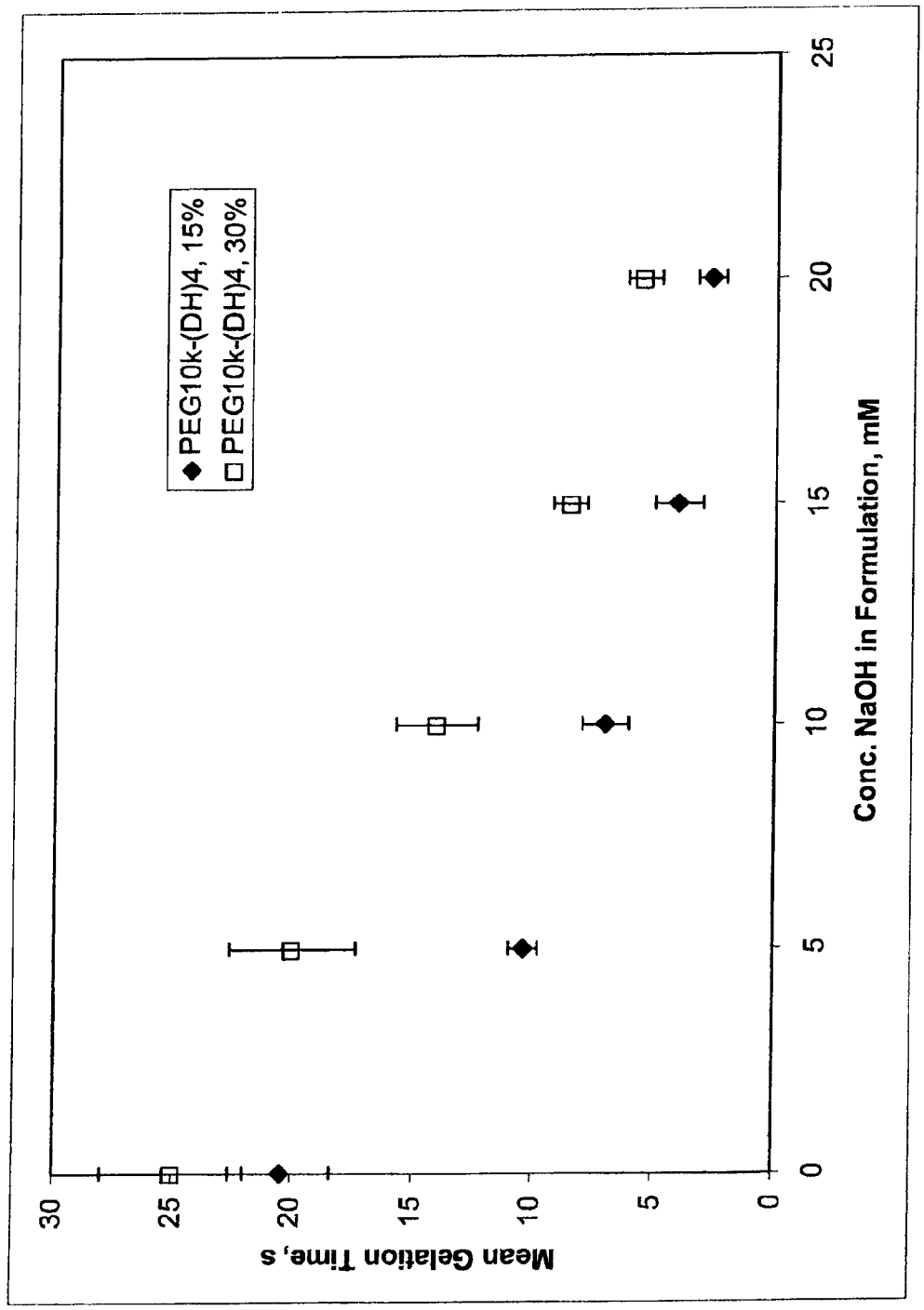
FIG. 12 provides data for the preparation of rapidly gelling formulations using an elevated pH buffer.

Adhesive formulations were prepared either with or without NaOH as described above at 15 and 30% solids. The concentration of NaOH in the polymer precursor solution was varied from 10 to 40 mM. Crosslinking precursor solutions were prepared such that after correction for the volume contributed by the polymer, the each formulation gave a 2:1 stoichiometry of DHP groups to periodate ions. The gelation time of each formulation was determined by the vial-tilt method. The data are plotted in FIG. 12.

Swelling of Adhesives Under Physiological Conditions

The equilibrium swelling ratios of two formulations of adhesive were determined by the method described above. The individual formulations were prepared either with or without 20 mM NaOH as described above. The average volumetric swelling ratios for 6 samples of each formulation are shown in Table 5.

TABLE 5

| Formulation | Volumetric Swelling Ratio |
|---|---|
| PEG10k-(DH)$_4$ in PBS 2x (30% solids) 11.4 mg/mL NaIO$_4$ | 2.88 ± 0.20 |
| PEG10k-(DH)$_4$ in PBS 2x + 20 mM NaOH (30% solids) 11.4 mg/mL NaIO$_4$ | 3.60 ± 0.56 |

Lap Shear Adhesion on Porcine Dermis

Figure 13:
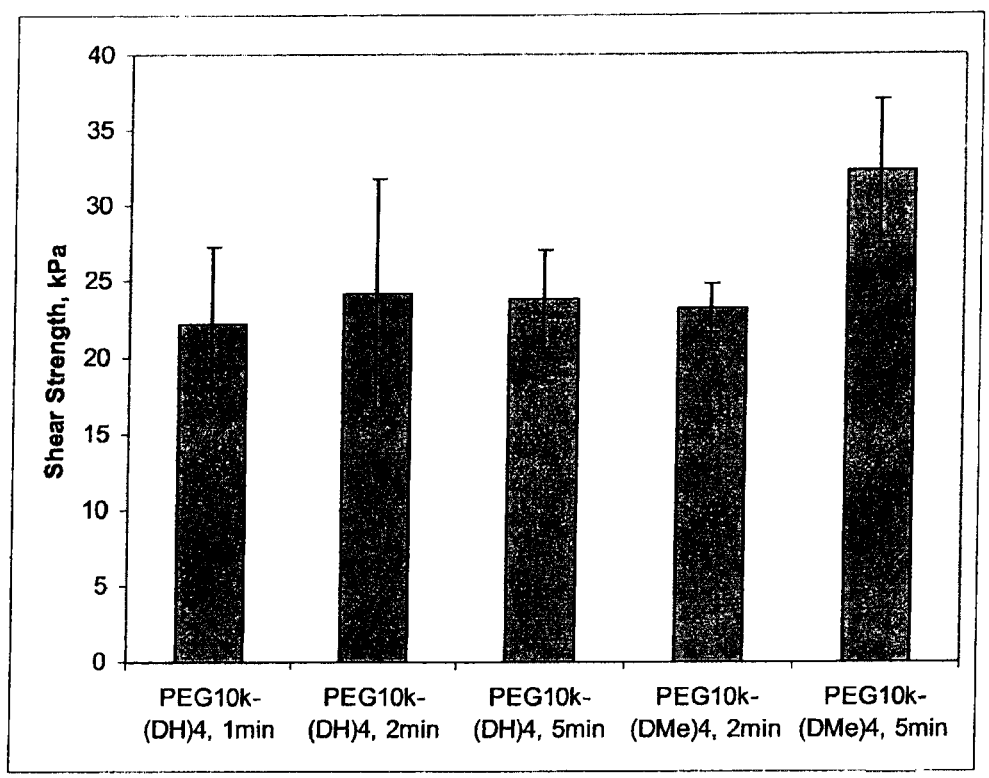
FIG. 13 provides lap shear testing on porcine dermis.

Adhesive formulations were prepared as described above to form gels containing 15% solids using either PEG10k-(DH)$_4$ or PEG10k-(DMe)$_4$, which contains an ester bond between the PEG backbone and the DHP functional group. Lap shear testing on porcine dermis was performed as described above after curing the samples for 1, 2 or 5 minutes. The data are shown in FIG. 13.

Lap Shear Strength of Adhesives on Collagen Substrate

Figure 14:
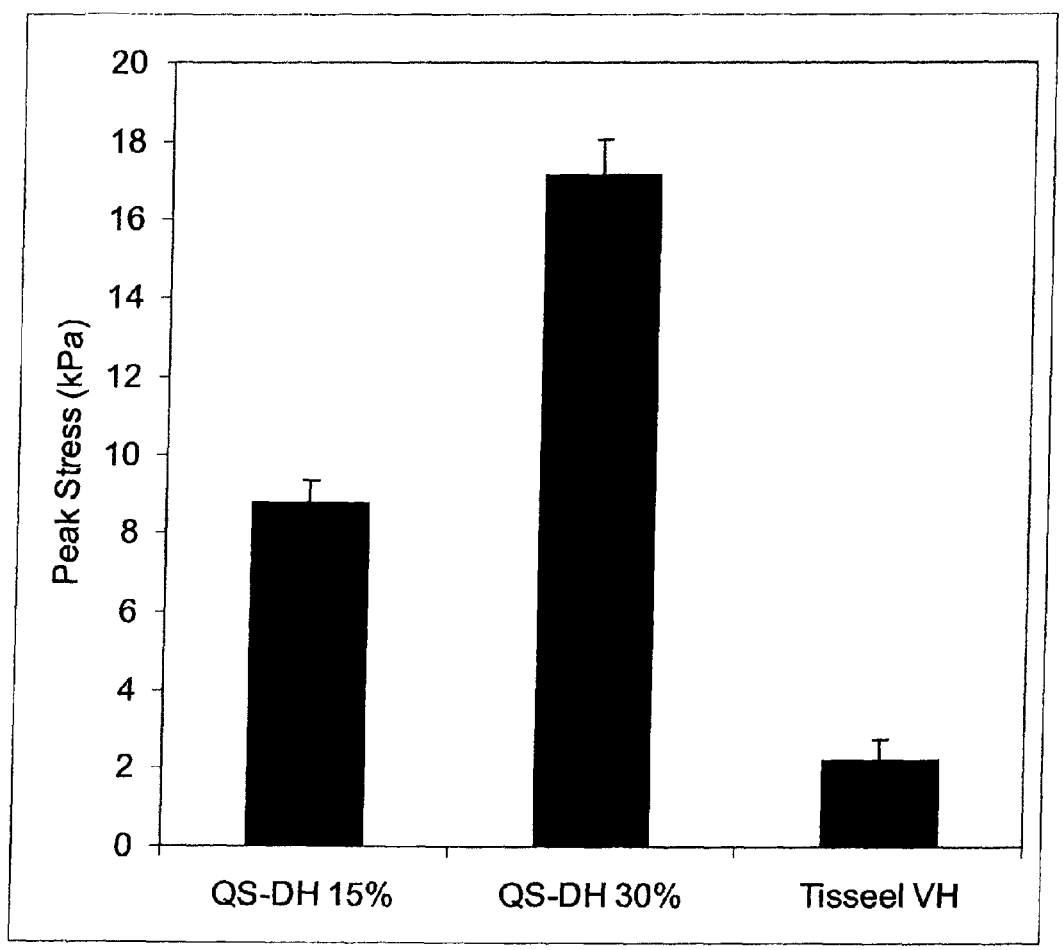
FIG. 14 provides lap shear strength of adhesives on a collagen substrate.

Polymer precursor solutions were prepared as described above to form gels containing 15 or 30% solids using PEG10k (DH)4. The lap shear adhesive strength of these formulations was determined according the method described above. Tisseel®, a commercially available fibrin sealant (Baxter Healthcare), was used as a control and was prepared and applied in a method consistent with the manufacturer's recommendations. The data are shown in FIG. 14.

T-Peel Strength of Adhesives on Collagen Substrate

Figure 15:
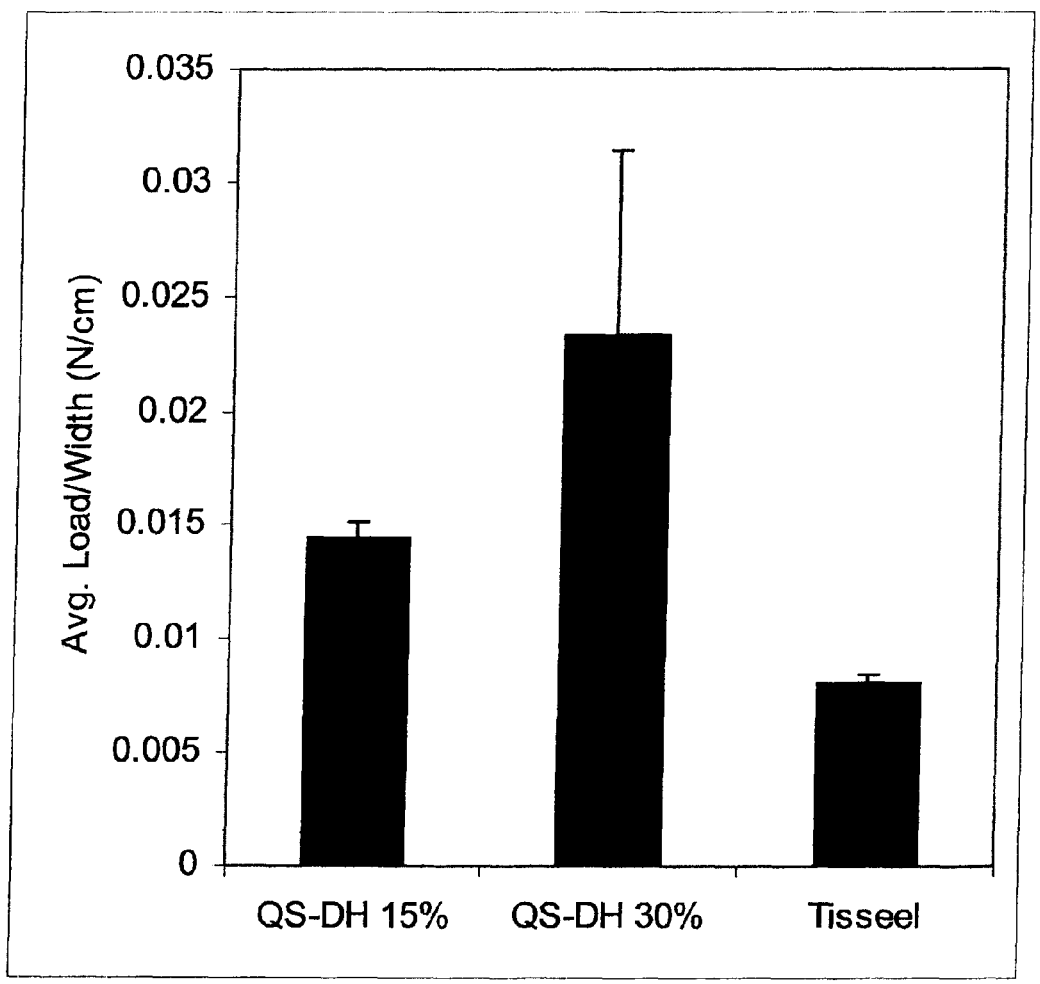
FIG. 15 provides T-Peel strength of adhesives on a collagen substrate.

Polymer precursor solutions were prepared as described above to form gels containing 15 or 30% solids using PEG10k (DH)$_4$. The lap shear adhesive strength of these formulations was determined according the method described above. Tisseel®, a commercially available fibrin sealant (Baxter Healthcare), was used as a control and was prepared and applied in a method consistent with the manufacturer's recommendations. The data are shown in FIG. 15.

Burst Strength of Adhesives on Collagen Substrate

Figure 16:
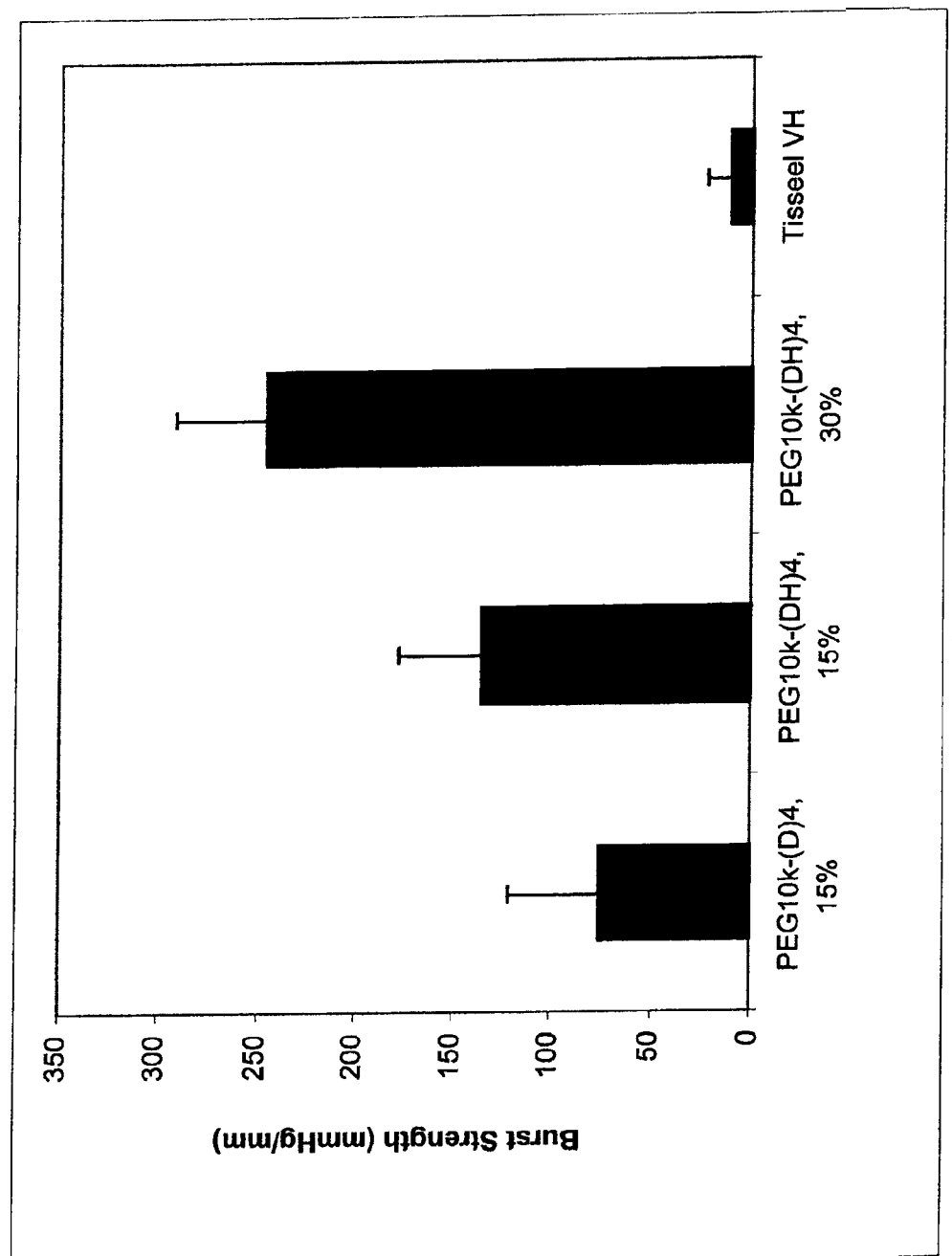
FIG. 16 provides burst strength of adhesives on a collagen substrate.

Polymer precursor solutions were prepared as described above to form gels containing 15 or 30% solids using PEG10k (D)$_4$ or PEG10k(DH)$_4$. The burst strength of these formulations was determined according the method described above. Tisseel®, a commercially available fibrin sealant (Baxter Healthcare), was used as a control and was prepared and applied in a method consistent with the manufacturer's recommendations. The data are shown in FIG. 16.

Adhesion of Bone and Demineralized Bone Matrix

Figure 17:
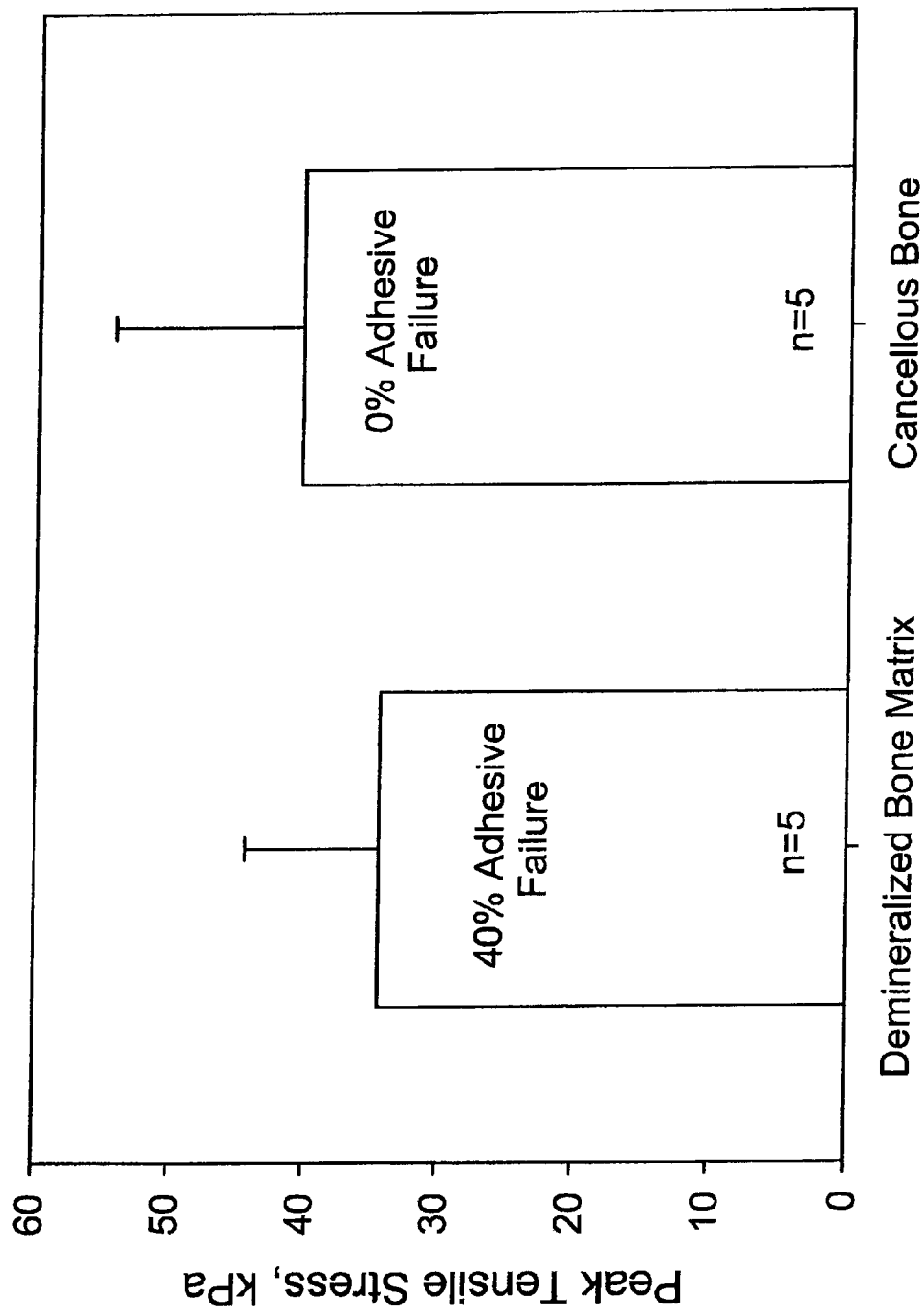
FIG. 17 provides adhesion of bone and demineralized bone matrix.

Polymer precursor solutions were prepared as described above to form gels containing 15% solids using PEG10k (DH)$_4$. Cubes of bovine cancellous bone and demineralized bone matrix (each approx. 1 cm$^3$; Osteotech, Inc.. Eatontown, N.J.) were drilled and tapped to receive a #8×32 machine screw to accommodate the adhesion testing apparatus. Adhesive was expressed from a dual syringe device (Micromedics, p/n SA-3303) using a static mixing tip (Micromedics, p/n SA-3678) onto one cube on the face opposite the drilled hole. The second cube was immediately approximated on top of the first and the assemblies were allowed to cure for 2 min at room temperature on the laboratory bench. Test assemblies were subsequently incubated in a 37° C. saline bath for 1 hour. Assemblies were then removed from the bath and mounted in a universal tester to test adhesive strength. Assemblies were strained axially until failure at a 5 mm/min strain rate. Peak load was recorded for each of the five assemblies tested and the results of the adhesive strength tests were normalized to area and reported in kPa. For each test assembly the mode of failure (adhesive or cohesive) was noted. The data are in shown in FIG. 17.

Spray Application of Crosslinker and Polymer to Form Crosslinked Colored Hydrogel Film Two solutions (Component A and B) were prepared. Component A consisted of PEG10k(DH)$_4$ in PBS2x buffer supplemented with 15 mM NaOH. Component B consisted of NaIO$_4$ dissolved in water containing 15 mM NaOH and 0.025% FD & C Blue #1 dye. These solutions were prepared such that the DHP to IO$_4^-$ stoichiometric ratio was 2:1 when delivered in equal volumes and the final total solution concentration was 15% solids.

Figure 18:
FIG. 18 provides spray application of crosslinker and polymer to form crosslinked colored hydrogel film.

A Fibriject™ (Micromedics, Inc.) 3 mL syringe holder and plunger link was used, preloaded with 2 mL of each solution and attached to a dual barrel atomizing sprayer (Micromedics, Inc., p/n SA-3652). The sprayer has two hubs for the syringes to connect to allowing the to fluids to be advanced through two separate lumens over a preset distance. A third hub exists for the application of the atomizing gas. Nitrogen was used in this example. The distal tip of the sprayer contain a chamber where the gas expands out of an introduction tube, then flows past the two polymer solution nozzles in an annular space around each. The atomized mixture in then forced through a spray orifice to allow for well mixed, thin uniform coatings to be applied to surfaces as illustrated in FIG. 18.

Wound Closure in Rat Dermis Model

Surgical Procedure: A total of 48 Sprague-Dawley rats (350-399 g) were tested. The dorsal skin was shaved, and the skin prepped for surgery. Two 5-cm long incision wounds were made 15 mm from and parallel to the dorsal midline, and centered on the thoracolumbar junction. The incisions were made perpendicular to the skin surface, and through the epidermis, dermis and subcutaneous muscle layers, but leaving the deep fascia intact. Hemostasis was obtained by direct pressure using sterile gauze. The wounds were repaired by 1 of the 4 following treatments:

15% solids formulation of PEG10k-(DH)$_4$ (Example A).
30% solids formulation of PEG10k-(DH)$_4$ (Example B).
Dermabond™ (2-octyl cyanoacrylate adhesive).
Interrupted 5-0 polypropylene sutures only (placed 5 mm apart and 3-4 mm from the wound line).

The repaired wounds were dressed with gauze and tape, appropriate antibiotic was administered, and the animals were allowed to recover. Twelve animals were euthanized at each of 4 hours, and 3, 7, and 21 days.

Assessments: The skin from the incision wound test area on both sides of the spine was harvested from each animal. The subcutaneous muscle fascia was separated from the undersurface of the skin. Three uniform 30 mm×10 mm test strips of skin were cut at equally spaced intervals from the skin samples from both sides of the spine. Two of these samples from each incision were stored in a zip-lock plastic bag and transported to a biomechanics lab for mechanical testing within two hours from sample harvest. The third strip from each incision was fixed in formalin and prepared for histology as described below. The test strips of skin for mechanical testing were mounted in a materials test machine by means of grips with serrated surfaces to minimize slippage during testing. The test strips were loaded to failure in tension at a rate of 10 mm/min, and the tensile failure strength was recorded and the character of the tissue failure noted. Note that in specimens from the 3, 7 and 21-day groups where the wound was closed with sutures, one of the two specimens from the incision was tested with the sutures cut, and the other specimen with the sutures intact.

Figure 19:
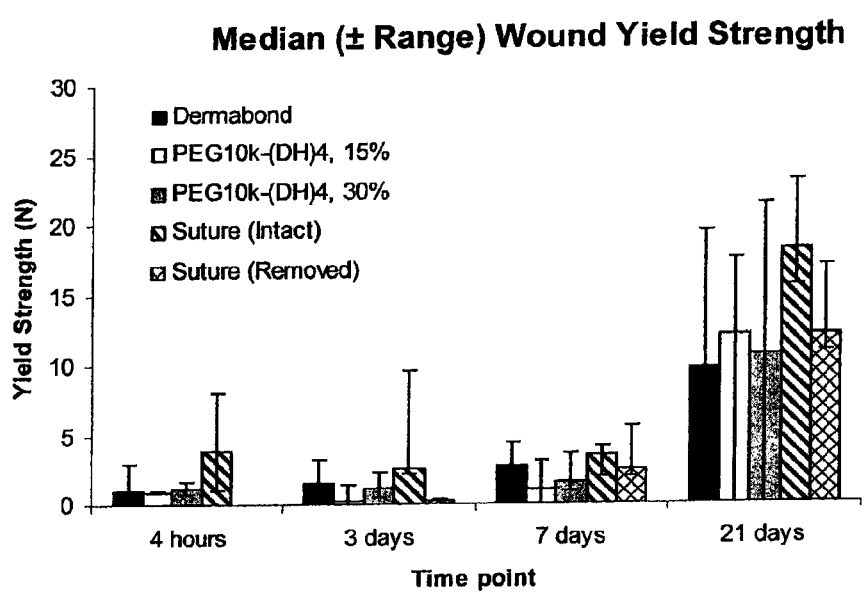
FIG. 19 provides mean wound yield strength for various repair methods.
Figure 20:
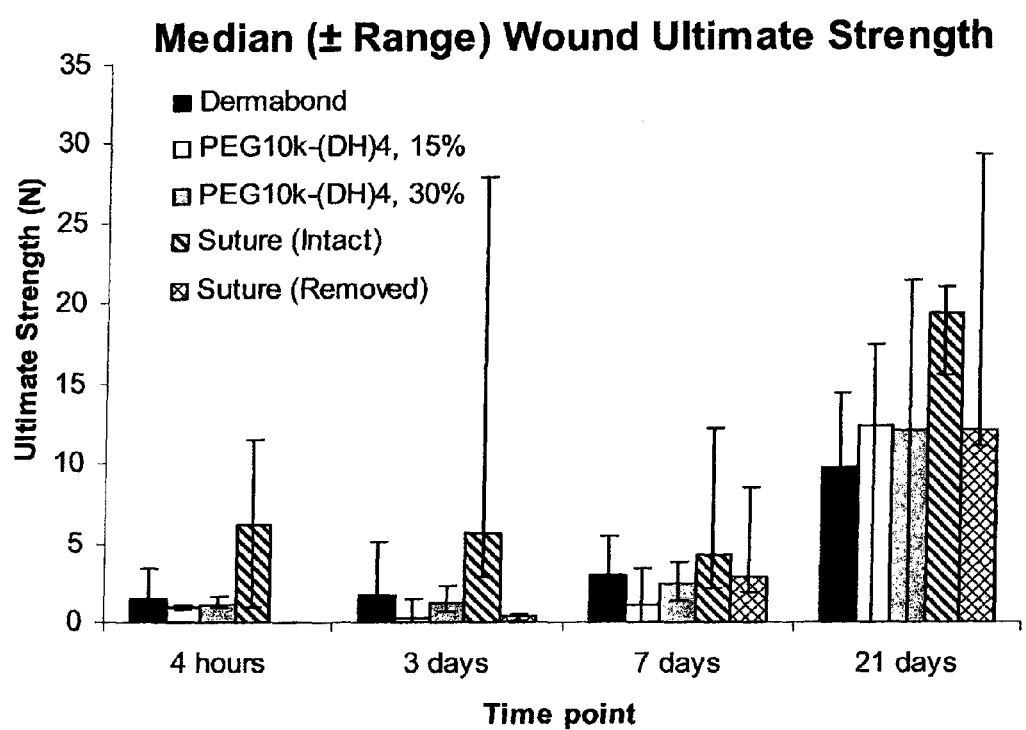
FIG. 20 provides wound ultimate strength for various repair methods.
Figure 21:
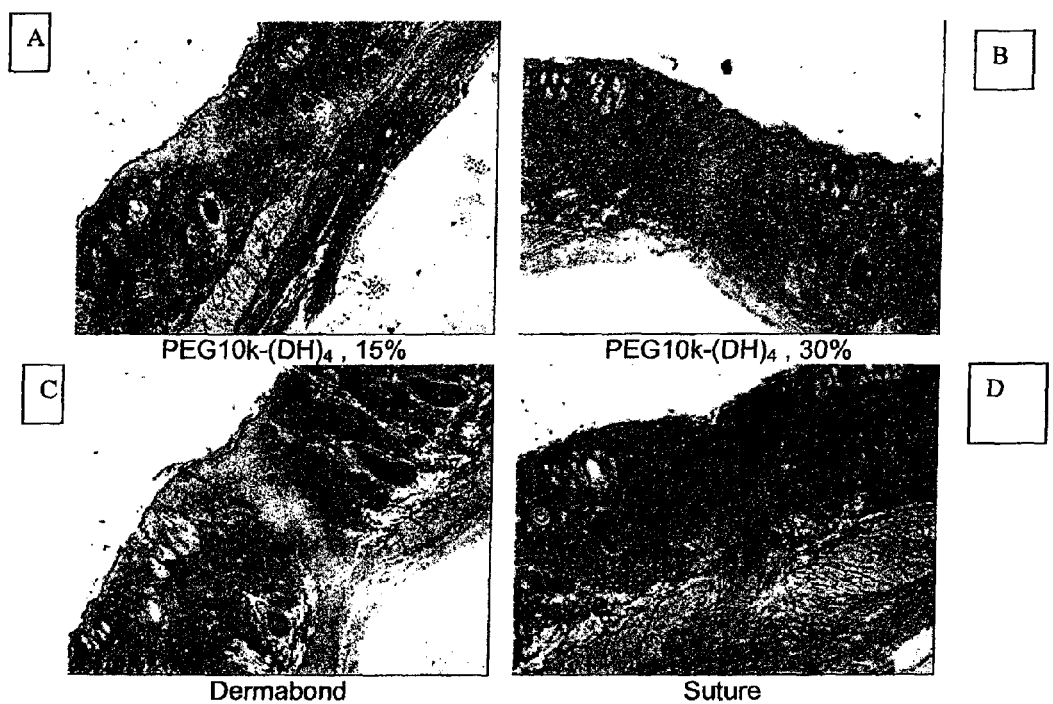
FIG. 21 (A-D) provides characteristic histological sections for various repair methods.

Descriptive histology was performed on one of the three 30 mm×10 mm test strips from the 6 animals at each of 4 time points for each of the 4 treatments, for a total of 96 sections for this histologic assessment. The harvested skin samples were immediately fixed in 10% formalin, processed and embedded in paraffin. Histologic specimens (5 μm thick) were sectioned perpendicular to the wound surface and stained with hematoxylin and eosin. Mean wound yield strength and mean wound ultimate strength for each repair method are shown in FIG. 19 and FIG. 20, respectively. Characteristic histological sections from each repair method are shown in FIG. 21.

Oral Sealant Degradation

A formulation of PEG10k-(DMe)$_4$ prepared according to Example# (15% solids) was applied to the oral cavity (cheek tissue) of 16 hamsters. Observations regarding the presence of the hydrogel were made 1, 3, 5, and 7 days after application. The results are listed below in Table 6.

TABLE 6

| Time point | # Sites with Hydrogel Remaining |
|---|---|
| Day 1 | 3 |
| Day 3 | 2 |
| Day 5 | 2 |
| Day 7 | 0 |

Dural Sealing in Canine Model

Twelve beagles (5-12 kg) were anesthetized with pentothal (14 mg/kg, IV to effect). The surgical site was prepared by clipping the fur and then cleansing the site with iodine scrub, alternating with 70% isopropyl alcohol three times, and painting with iodine solution. Each animal was placed in ventral recumbency with the head extended and slightly elevated to alleviate pressure on the jugular veins. A midline skin incision was made and the skin was retracted for a lateral rostrotentorial craniotomy. Dissection was continued through the subcutaneous tissues and muscle layers until the skull is encountered. The tissues were retracted, exposing the craniotomy site. A hand-held pneumatic drill with an appropriately-sized burr, in conjunction with copious amounts of sterile saline, was used to create an approximate 2 cm×3 cm craniotomy to the right of the midline. Bleeding from the craniotomy was controlled with bipolar electrocautery and bone wax. The excised bone flap was placed in a bowl of sterile saline to prevent drying of the tissues.

An incision just large enough to accommodate the blade of a periosteal elevator was made in the dura. The periosteal elevator was placed between the dura and the brain to protect the brain tissue while a 2 cm longitudinal incision was made in the dura. The pia-arachnoid was incised to demonstrate cerebral spinal fluid (CSF) leakage.

The dural incision was closed with four evenly spaced sutures of 6-0 Prolene. The durotomy site was blotted dry. The control (DuraSeal™) or test articles were mixed and then applied directly over the durotomy repair site. Following each application, intra-operative CSF leakage was assessed, via the Valsalva maneuver to 20 cm H$_2$O. The presence of CSF leakage prior to closure was recorded. Holes were drilled through the bone flap and adjacent skull. The bone flap was placed into the craniotomy site and sutured in place with non-absorbable suture. The muscle layer was repositioned over the craniotomy site and closed with absorbable suture. The subcutaneous tissues were closed with absorbable suture and the skin was closed with staples and/or glue. The intra-operative observations concerning sealing of the sutured durotomy are shown in Table 7.

TABLE 7

| Treatment | Numbers Sealed/Total |
|---|---|
| Suture-only | 0/3 (incomplete data) |
| DuraSeal | 3/3 (incomplete data) |
| PEG10k-(DH)$_4$ (15% solids) | 1/3 |
| PEG10k-(DH)$_4$ + 20 mM NaOH (15% solids) | 2/3 |

Adjunctive Hemostasis in Canine Model with PTFE Patch

Eight male mixed breed hounds (approximately 25-35 kg) were anesthetized with pentothal (14 mg/kg, IV to effect). The surgical site was prepared by clipping the fur and then cleansing the site with iodine scrub, alternating with 70% isopropyl alcohol three times, and painting with iodine solution. Each animal was placed in dorsal recumbency on the operating table, and then aseptically prepped and draped. Indirect blood pressure was monitored during the procedure. Pressures were recorded at the time of clamp release after sealant application. Bilateral femoral artery ePTFE patch implantations and test and control sealant hemostasis evaluations were performed simultaneously by two teams of surgeons and assistants.

An incision was made over both femoral arteries and the arteries were exposed by sharp and blunt dissection. Lidocaine was applied topically to the femoral arteries to prevent vasospasm during dissection. Once the femoral arteries were isolated heparin was given, as needed, to achieve and maintain an activated clotting time of approximately 300 seconds.

Atraumatic clamps were placed proximal and distal on the femoral arteries to occlude blood flow. An approximate 2.5 cm longitudinal arteriotomy was made into the ventral surface of each vessel. Elliptical ePTFE patches, approximately 2.5 cm long and 0.5 cm wide were cut to size, packaged two per package, and steam sterilized prior to surgery. The patches were sewn into place with 6-0 Prolene on a taper needle in a continuous suture pattern.

After the ePTFE patches were implanted the distal and proximal vessel clamps were released for 1-3 seconds to expand the vessel and to document suture line bleeding. Blood loss was scored as oozing or bleeding. The clamps were re-applied and the vessel blotted dry with sterile gauze. The gauze was discarded.

A uniform layer of test or control sealant was applied to the suture line and to the ePTFE patch surface. In some cases the site was rotated to facilitate exposure of all surfaces. The test and control sealants were allowed to gel for at least 60 seconds. Pre-weighed gauze sponges were placed around the treatment site to collect any blood loss after clamp release. The surgeons will first remove the distal clamp and then the proximal clamp from each artery. The time of clamp release was recorded.

Close observation of the treatment site determined oozing or bleeding, which was recorded. If hemostasis was not achieved digital pressure with sterile, pre-weighed gauze for five minutes. The gauze sponges were reweighed to calculate blood loss. If hemostasis was not achieved after digital pressure, topical hemostatic agents, as well as heparin reversal were used as treatment adjuncts to achieve hemostasis, at the surgeon's discretion.

After hemostasis was established, the defect was observed for at least 1 minute. If no bleeding was noted, the wounds were closed. Any recurrence of bleeding or oozing, re-bleeding, or sloughing of the sealant was recorded. Tin these cases hemostasis was re-established, followed by another observation period of at least 1 minute.

The muscle, subcutaneous, and subcuticular tissues were closed with 3-0 PDS and the skin was glued.

The intraoperative observations concerning sealing of the sutured durotomy are shown in Table 8.

TABLE 8

| Animal # | | Treatment Coseal (C) Fast Gel (FG) Slow Gel (SG) | Suture line bleeding prior to treatment? (Y/N) | Hemostasis after sealant application? (Y/N) | Hemostasis within 5 minutes of treatment? (Y/N) | Blood loss (g) |
|---|---|---|---|---|---|---|
| 101 | Right leg | SG | Y | N | N | 3.7 |
| | Left leg | C | Y | N | N | 2.9 |
| 102 | Right leg | FG | Y | N | Y | 3.7 |
| | Left leg | C | Y | N | N | 9.9 |
| 103 | Right leg | FG | Y | N | N (Note 1) | 2.9 |
| | Left leg | SG | Y | N | N | 1.5 |
| 104 | Right leg | SG | Y | N | Y | 2.1 |
| | Left leg | FG | Y | N | N | 2.0 |
| 105 | Right leg | C | Y | Y | Y | 0 |
| | Left leg | SG | Y | Y | Y | 0 |
| 106 | Right leg | C | Y | N | N | 3.5 |
| | Left leg | FG | Y | N | N | 4.5 |
| 107 | Right leg | SG | Y | N | N | 1.8 |
| | Left leg | FG | Y | Y | Y | 0 |
| 108 | Right leg | FG | Y | N | N (Note 2) | 16.5 |
| | Left leg | SG | Y | N | N | 1.8 |

(Note 1): Test article remained tacky at proximal end - the site of oozing.
(Note 2): Surgeon failed to completely cover suture line with sealant. Blood loss was from uncovered suture holes only. No leakage from holes that were covered with sealant.
Note 3:
The hematoma was most probably the result of re-bleeding at the suture line; however, seepage from blood vessels around the incision site cannot be ruled out.

REFERENCES

1. Fuller, W. D., M. S. Verlander, and M. Goodman, DOPA-containing polypeptides. I. Improved synthesis of high-molecular-weight poly(L-DOPA) and water-soluble copolypeptides. Biopolymers, 1978. 17(12): p. 2939-43.

2. Fuller, W. D., M. S. Verlander, and M. Goodman. *A Procedure for the Facile Synthesis of Amino-Acid N-Carboxyanhydride*. Biopolymers, 1976. 15: p. 1869-1871.

3. Bruce P. Lee, Chi-Yang Chao, F. Nelson Nunalee, Emre Motan, Kenneth R. Shull, and Phillip B. Messersmith, "Rapid Gel Formation and Adhesion in Photocurable and Biodegradable Block Copolymers with High DOPA Content", *Macromolecules*, 39, 1740-1748, (2006).

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention

What is claimed is:

1. A composition comprising the formula:

$$CA\text{-}[Z\text{-}PA\text{-}(L)_a\text{-}(DHPD)_b\text{-}(AA)_c\text{-}PG]_n \quad (II)$$

wherein
CA is carbon;
each Z, independently, is a C1 to a C6 linear or branched, substituted or unsubstituted alkyl group or a bond;
each PA, independently, is a substantially poly(alkylene oxide) polyether;
each L, independently, optionally, is a linker or is a linking group selected from amide, ester, urea, carbonate or urethane linking groups;
each DHPD, independently, is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value of 4.

2. The composition of claim 1, wherein each Z is a methylene.

3. The composition of claim 1, wherein each PA is a polyethylene glycol polyether.

4. The composition of claim 1, wherein the molecular weight of each of PA is between about 1,250 and about 12,500 daltons.

5. The composition of claim 1, wherein each DHPD is dopamine, 3,4-dihydroxyphenyl alanine, 2-phenyl ethanol or 3,4-dihydroxyhydrocinnamic acid.

6. The composition of claim 5, wherein "c" is zero.

7. The composition of claim 1, wherein PG is a hydrogen atom.

8. The composition of claim 1, wherein "a" is zero.

9. The composition of claim 1, wherein "b" is 1, 2, 3 or 4.

10. The composition of claim 1, wherein the li nking group is an amide, urea or urethane.

11. The composition of claim 5, wherein "c" is 1, 2, 3 or 4.

12. The composition of claim 11, wherein AA is lysine.

13. The composition of claim 11, wherein PG is a hydrogen atom.

14. The composition of claim 11, wherein "a" is zero.

15. The composition of claim 11, wherein "b" is 1, 2, 3 or 4.

16. The composition of claim 11, wherein the linking group is an amide, ester or urethane.

17. The composition of claim 5, wherein "a" is 1 and each L is an alkylene dicarboxylic acid moiety.

18. The composition of claim 17, wherein the alkylene dicarboxylic acid moiety is succinic acid.

19. The composition of claim 17, wherein PG is a hydrogen atom.

20. The composition of claim 17, wherein "b" is 1, 2, 3 or 4.

21. The composition of claim 1, wherein the DHPD has at least 2 hydroxyl groups.

22. The composition of claim 1, wherein the DHPD has 2 hydroxyl groups.

23. A method to adhere biological tissues together, comprising the step of administering to the tissue a sufficient amount of an adhesive material as claimed in claim 1, such that the biological tissues remain adhered to each other.

24. A method of crosslinking the material as recited in claim 1 by reacting said hydroxyphenyl groups with an oxidant to yield hydroxyphenyl free radical species, such that the free radical species react to yield a crosslinkage comprising multiple hydroxyphenyl species.

25. The method of claim 24, wherein the oxidant is a periodate.

26. The method of claim 24, wherein the oxidant is $NaIO_3$, $FeCl_3$, $H_2O_2$, oxygen, an inorganic base, an organic base or an oxidase.

27. A cross linked macromolecular hydrogel comprising the formula:

$$CA\text{-}[Z\text{-}PA\text{-}(L)_a\text{-}(DHPD)_b\text{-}(AA)_c\text{-}PG]_n \quad (II)$$

wherein
CA is a central atom that is carbon;
each Z, independently, is a C1 to a C6 linear or branched, substituted or unsubstituted alkyl group or a bond;
each PA, independently, is a substantially poly(alkylene oxide) polyether;
each L, independently, optionally, is a linker or is a linking group selected from amide, ester, urea, carbonate or urethane linking groups;
each DHPD, independently is a multihydroxy phenyl derivative;
each AA independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value of 4, wherein at least one linkage is formed between two DHPD groups attached respectively to adjacent molecules.

28. A composition comprising the formula:

$$CA\text{-}[Z\text{-}PA\text{-}(L)_a\text{-}(DHPD)_b\text{-}(AA)_c\text{-}PG]_n \quad (I)$$

wherein
CA is a central atom selected from carbon, oxygen, sulfur, nitrogen, or a secondary amine;
each Z, independently is a C1 to a C6 linear or branched, substituted or unsubstituted alkyl group or a bond;
each PA, independently, is a substantially poly(alkylene oxide) polyether;
each L, independently, optionally, is a linker or is a linking group selected from amide, ester, urea, carbonate or urethane linking groups;
each DHPD, independently, is a multihydroxy phenyl derivative;
each AA, independently, optionally, is an amino acid moiety,
each PG, independently, is an optional protecting group, and if the protecting group is absent, each PG is replaced by a hydrogen atom;
"a" has a value of 0 when L is a linking group or a value of 1 when L is a linker;
"b" has a value of one or more;
"c" has a value in the range of from 0 to about 20; and
"n" has a value from 3 to 15.

29. A cross linked macromolecular hydrogel comprising the formula:

$$CA\text{-}[Z\text{-}PA\text{-}(L)_a\text{-}(DHPD)_b\text{-}(AA)_c\text{-}PG]_n \quad (I)$$

wherein

CA is a central atom selected from carbon, oxygen, sulfur, nitrogen, or a secondary amine;

each Z, independently is a C1 to a C6 linear or branched, substituted or unsubstituted alkyl group or a bond;

each PA, independently, is a substantially poly(alkylene oxide) polyether;

each L, independently, optionally, is a linker or is a linking group selected from amide, ester, urea, carbonate or urethane linking groups;

each DHPD, independently, is a multihydroxy phenyl derivative;

each AA, independently, optionally, is an amino acid moiety, each PG, independently, is an optional protecting group, and if the protecting group is absent, each PG is replaced by a hydrogen atom;

"a" has a value of 0 when L is a linking group or a value of 1 when L is a linker;

"b" has a value of one or more;

"c" has a value in the range of from 0 to about 20; and

"n" has a value from 3 to 15, wherein at least one linkage is formed between two DHPD groups attached respectively to adjacent molecules.

* * * * *